US012667709B2

(12) United States Patent
Mayse et al.

(10) Patent No.: US 12,667,709 B2
(45) Date of Patent: Jun. 30, 2026

(54) FLUID-MANAGEMENT SYSTEM AND METHOD

(71) Applicant: Pleural Dynamics, Inc., Wayzata, MN (US)

(72) Inventors: Martin Mayse, Wayzata, MN (US); John Streeter, Colorado Springs, CO (US)

(73) Assignee: Pleural Dynamics, Inc., Wayzata, MN (US)

( * ) Notice: Subject to any disclaimer, the term of this patent is extended or adjusted under 35 U.S.C. 154(b) by 450 days.

(21) Appl. No.: 18/350,412

(22) Filed: Jul. 11, 2023

(65) Prior Publication Data

US 2023/0364409 A1 Nov. 16, 2023

Related U.S. Application Data

(63) Continuation of application No. 18/108,124, filed on Feb. 10, 2023, now Pat. No. 11,707,614, which is a continuation-in-part of application No. 17/733,138, filed on Apr. 29, 2022, now Pat. No. 11,577,065.

(51) Int. Cl.
*A61M 39/24* (2006.01)
*A61M 39/22* (2006.01)

(52) U.S. Cl.
CPC ..... *A61M 39/22* (2013.01); *A61M 2039/2433* (2013.01); *A61M 2205/3331* (2013.01)

(58) Field of Classification Search
CPC .............. A61M 39/0247; A61M 39/24; A61M 2039/242; A61M 2039/2426; A61M 2210/101
See application file for complete search history.

(56) References Cited

U.S. PATENT DOCUMENTS

| | | | |
|---|---|---|---|
| 3,233,610 A | 2/1966 | Charles | |
| 3,463,159 A | 8/1969 | Heimlich | |
| 3,683,929 A | 8/1972 | Holter | |
| 4,487,603 A | 12/1984 | Harris | |

(Continued)

FOREIGN PATENT DOCUMENTS

| | | |
|---|---|---|
| CN | 101720242 A | 6/2010 |
| EP | 0270205 A2 | 6/1988 |

(Continued)

OTHER PUBLICATIONS

"International Bureau, International Search Report and Written Opinion mailed on Aug. 7, 2023, issued in connection with International Application No. PCT/US2023/020231, filed Apr. 27, 2023", 11 pages.

(Continued)

*Primary Examiner* — Deanna K Hall
(74) *Attorney, Agent, or Firm* — Lee Sullivan Shea & Smith LLP

(57) ABSTRACT

An example valve assembly includes (i) an inlet, (ii) an outlet, (iii) a plurality of one-way valves positioned between the inlet and outlet, and (iv) an adjustable outlet lock positioned downstream of the plurality of one-way valves and configured to selectively prevent fluid movement through the outlet, wherein the valve assembly is configured to (a) be positioned external to a body of a person and (b) attach to a tube for carrying fluid from a body cavity of the person to the valve assembly.

25 Claims, 43 Drawing Sheets

(56) References Cited

U.S. PATENT DOCUMENTS

| | | | |
|---|---|---|---|
| 4,588,394 A | 5/1986 | Schulte et al. | |
| 4,725,207 A | 2/1988 | Buchwald et al. | |
| 4,850,955 A | 7/1989 | Newkirk | |
| 4,921,488 A | 5/1990 | Maitz et al. | |
| 5,009,635 A | 4/1991 | Scarberry | |
| 5,154,693 A | 10/1992 | East et al. | |
| 5,261,459 A | 11/1993 | Atkinson et al. | |
| 5,484,401 A * | 1/1996 | Rodriguez | A61M 39/0606 |
| | | | 604/28 |
| 5,738,656 A | 4/1998 | Wagner | |
| 5,830,172 A | 11/1998 | Leveen et al. | |
| 6,254,581 B1 | 7/2001 | Scott | |
| 7,135,010 B2 | 11/2006 | Buckman et al. | |
| 7,326,197 B2 | 2/2008 | Breznock et al. | |
| 7,766,886 B2 | 8/2010 | Garcia et al. | |
| 8,157,760 B2 | 4/2012 | Criado et al. | |
| 8,518,053 B2 | 8/2013 | Tanaka et al. | |
| 8,636,721 B2 | 1/2014 | Alam et al. | |
| 9,314,599 B2 | 4/2016 | Karwoski et al. | |
| 9,393,353 B2 | 7/2016 | Alam et al. | |
| 9,393,387 B1 | 7/2016 | Mayse et al. | |
| 9,421,348 B2 | 8/2016 | Lenihan et al. | |
| 9,662,478 B2 | 5/2017 | Browd et al. | |
| 9,907,887 B2 | 3/2018 | Alam et al. | |
| 10,213,532 B2 | 2/2019 | Alam et al. | |
| 10,252,037 B2 | 4/2019 | Degen et al. | |
| 10,265,442 B2 | 4/2019 | Luxon et al. | |
| 10,300,255 B1 | 5/2019 | Mayse et al. | |
| 10,517,538 B2 | 12/2019 | Burnett et al. | |
| 10,569,003 B2 | 2/2020 | Degen et al. | |
| 10,646,629 B2 | 5/2020 | Roe et al. | |
| 10,905,815 B2 | 2/2021 | Doshi et al. | |
| 11,571,555 B2 | 2/2023 | Mayse | |
| 11,577,065 B1 | 2/2023 | Mayse et al. | |
| 11,707,614 B1 | 7/2023 | Mayse et al. | |
| 11,779,741 B1 | 10/2023 | Mayse et al. | |
| 2007/0078442 A1 * | 4/2007 | Mayse | A61M 39/10 |
| | | | 604/533 |
| 2008/0125750 A1 | 5/2008 | Gaissert | |
| 2009/0024072 A1 | 1/2009 | Criado et al. | |
| 2011/0196194 A1 | 8/2011 | Forsell | |
| 2013/0197422 A1 | 8/2013 | Browd et al. | |
| 2015/0094644 A1 | 4/2015 | Lenihan et al. | |
| 2017/0143880 A1 | 5/2017 | Luxon et al. | |
| 2019/0105476 A1 | 4/2019 | Turtz | |
| 2019/0358438 A1 | 11/2019 | Fortune et al. | |
| 2021/0283330 A1 | 9/2021 | Mayse | |
| 2023/0044460 A1 | 2/2023 | Mayse | |

FOREIGN PATENT DOCUMENTS

| | | | |
|---|---|---|---|
| EP | 2714178 B1 | 12/2015 | |
| JP | S57112872 A | 7/1982 | |
| JP | 2002514096 A | 5/2002 | |
| JP | 2012030116 A | 2/2012 | |
| JP | 7676435 B2 | 5/2025 | |
| WO | 2007116387 A2 | 10/2007 | |
| WO | 2010026458 A1 | 3/2010 | |
| WO | 2016090378 A1 | 6/2016 | |
| WO | 20211088331 A1 | 9/2021 | |

OTHER PUBLICATIONS

"International Bureau, International Search Report and Written Opinion mailed on Jun. 22, 2021, issued in connection with International Application No. PCT/US2021/021643, filed on Mar. 10, 2021", 15 pages.

"International Bureau, International Preliminary Report on Patentability mailed Sep. 29, 2022, issued in connection with International Application No. PCT/US2021/021643, filed Mar. 10, 2021", 11 pages.

"U.S. Appl. No. 18/103,773, filed Jan. 31, 2023, with inventors Mayse, Martin et al., entitled "Fluid-Management System and Method,".", 68 pages.

Astoul, et al., "Novel Pleural-Bladder Pump in Malignant Pleural Effusions: from Animal Model to Man", Thorax, vol. 75, Mar. 12, 2020, 432-434.

Aspira Drainage System, "Aspira Drainage System Product Features," 2 pages. [retrieved on Apr. 25, 2022], Retrieved from the Internet: URL: <https://www.myaspira.com/clinicians/aspira-product-features/>.

Gogakos, Apostolos et al., "Heimlich valve and pneumothorax," Annals of Translational Medicine vol. 3(4), Mar. 2015, 7 pages. [retrieved on Apr. 25, 2022], Retrieved from the Internet: URL: <https://www.ncbi.nlm.nih.gov/pmc/articles/PMC4381465/>.

CareFusion Corporation, "Denver ascites shunts for patients with refractory ascites," 2012, 8 pages.

Bearpac Medical, "Passio Pump Drainage System," 2022, 2 pages. [retrieved on Apr. 25, 2022], Retrieved from the Internet: URL: <https://bearpac.com/passio-pump-drainage-system-2/>.

St. Joseph's Healthcare Hamilton, "A Heimlich Valve for Chest Drainage," Mar. 2005, 2 pages. [retrieved on Apr. 25, 2022], Retrieved from the Internet: URL: <https://bearpac.com/passio-pump-drainage-system-2/>.

Memorial Sloan Kettering Cancer Center, "About your PleurX Drainage Catheter," Jul. 12, 2021, 23 pages. [retrieved on Apr. 26, 2022], Retrieved from the Internet: URL: <https://www.mskcc.org/pdf/cancer-care/patient-education/about-your-pleurx-drainage-catheter>.

Potter, Perry, "Closed Chest Drainage Systems," 2014, Chapter 26, pp. 655-671, 17 pages. [retrieved on Apr. 26, 2022], Retrieved from the Internet: URL: <https://library.upei.ca/sites/library.upei.ca/files/Nurs2230X_PerryPotter_2014_655-671.pdf>.

Porcel, José M, "Chest Tube Drainage of the Pleural Space: A Concise Review for Pulmonologists," Tuberculosis and Respiratory Diseases vol. 81, Apr. 2, 2018, 12 pages. [retrieved on Apr. 26, 2022], Retrieved from the Internet: URL: <https://www.ncbi.nlm.nih.gov/pmc/articles/PMC5874139/#>.

European Patent Office, European Extended Search Report mailed on Mar. 3, 2026, issued in connection with European Application No. 23797295.5, 11 pages.

* cited by examiner

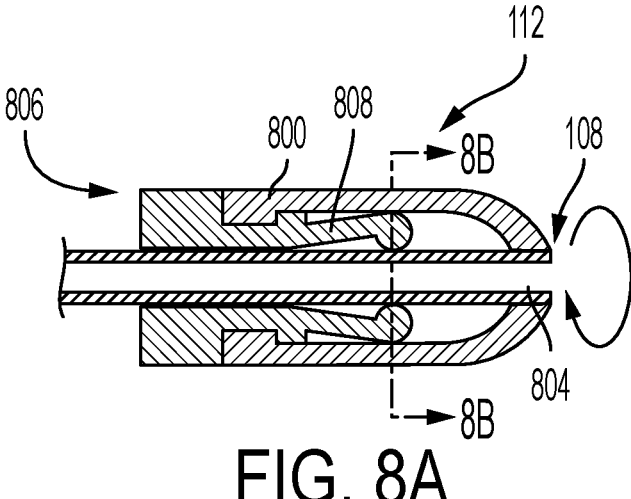
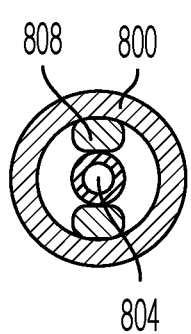
FIG. 8A                    FIG. 8B
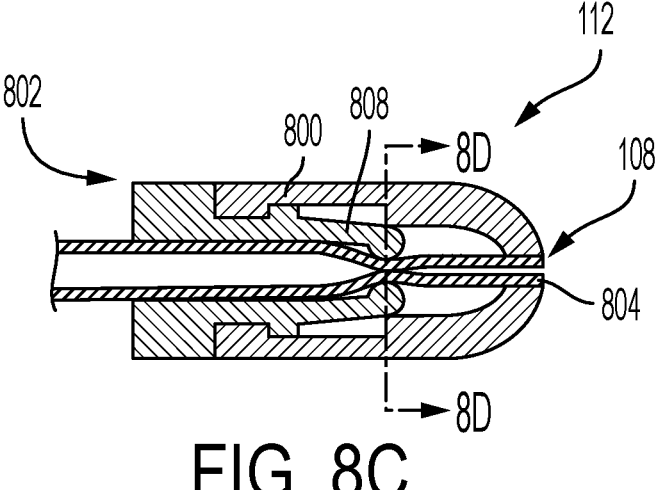
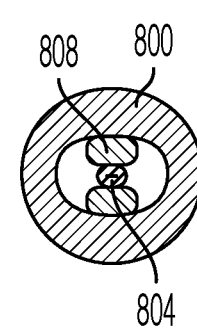
FIG. 8C                    FIG. 8D

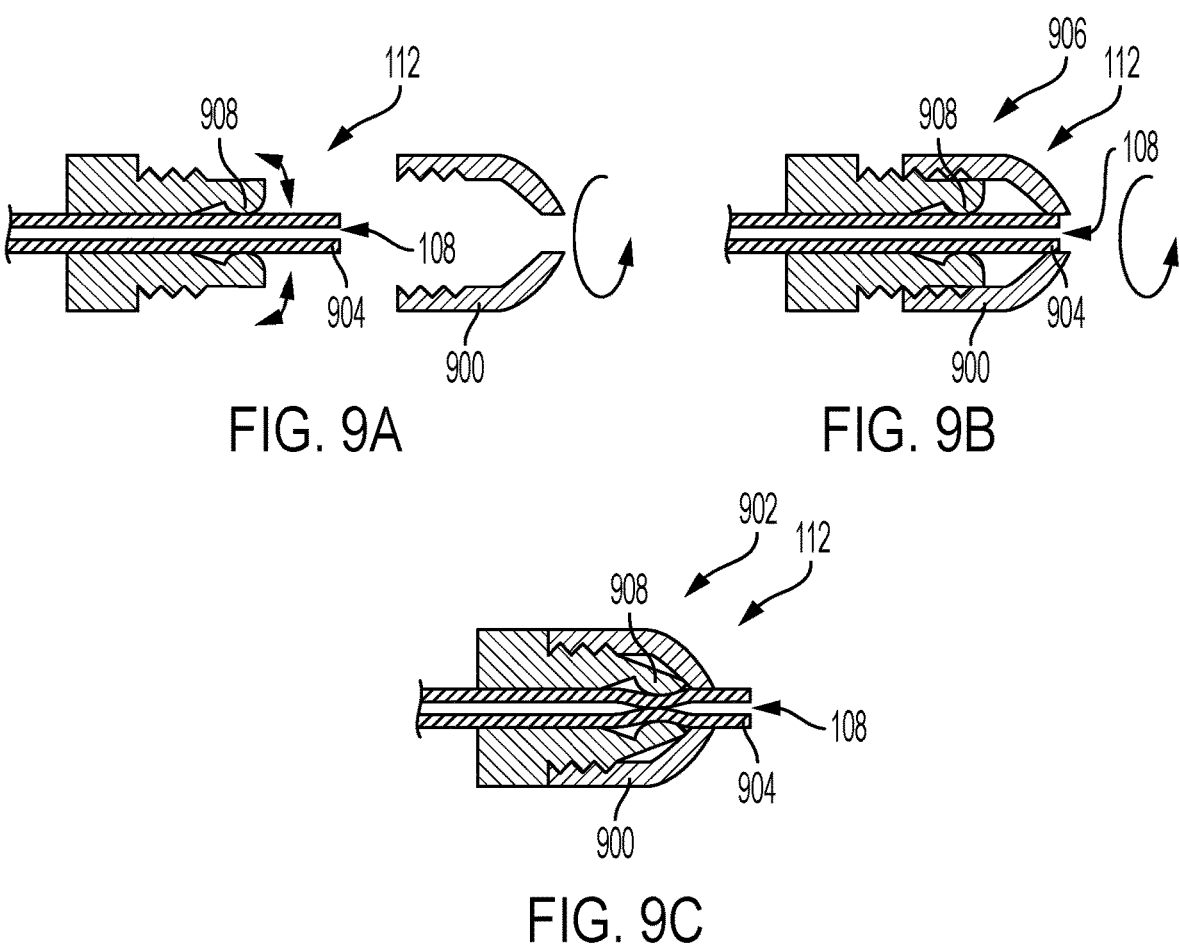
FIG. 9A
FIG. 9B
FIG. 9C
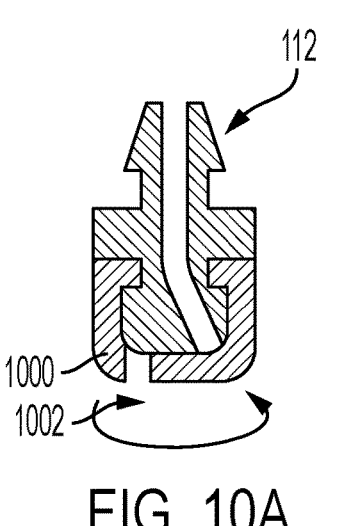
FIG. 10A
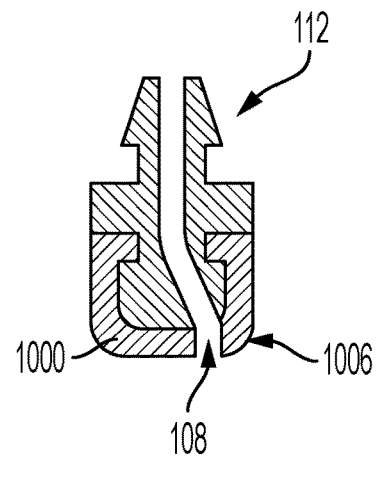
FIG. 10B

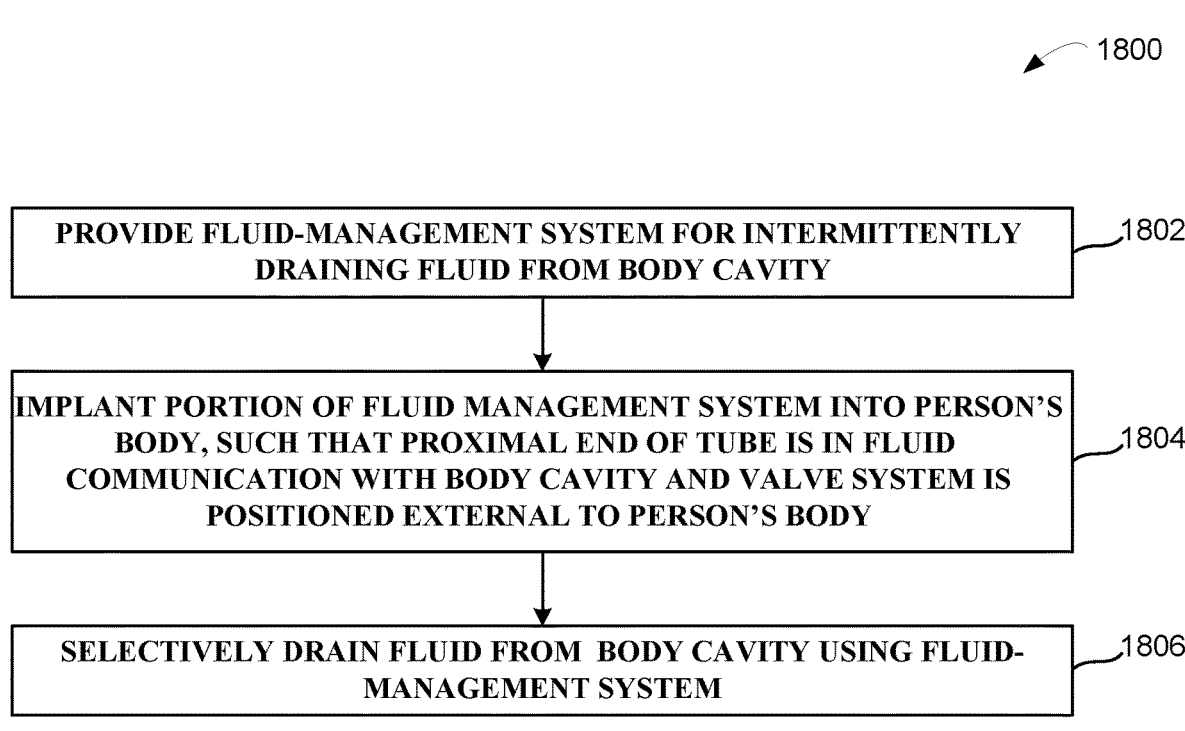

1800

PROVIDE FLUID-MANAGEMENT SYSTEM FOR INTERMITTENTLY DRAINING FLUID FROM BODY CAVITY — 1802

IMPLANT PORTION OF FLUID MANAGEMENT SYSTEM INTO PERSON'S BODY, SUCH THAT PROXIMAL END OF TUBE IS IN FLUID COMMUNICATION WITH BODY CAVITY AND VALVE SYSTEM IS POSITIONED EXTERNAL TO PERSON'S BODY — 1804

SELECTIVELY DRAIN FLUID FROM BODY CAVITY USING FLUID-MANAGEMENT SYSTEM — 1806

FIG. 18

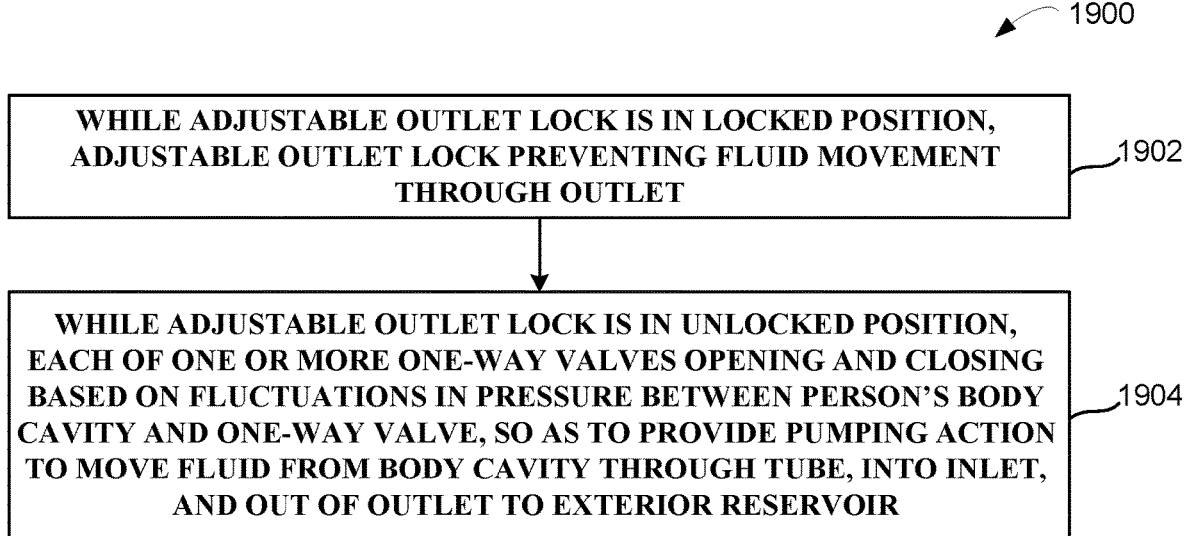

1900

WHILE ADJUSTABLE OUTLET LOCK IS IN LOCKED POSITION, ADJUSTABLE OUTLET LOCK PREVENTING FLUID MOVEMENT THROUGH OUTLET — 1902

WHILE ADJUSTABLE OUTLET LOCK IS IN UNLOCKED POSITION, EACH OF ONE OR MORE ONE-WAY VALVES OPENING AND CLOSING BASED ON FLUCTUATIONS IN PRESSURE BETWEEN PERSON'S BODY CAVITY AND ONE-WAY VALVE, SO AS TO PROVIDE PUMPING ACTION TO MOVE FLUID FROM BODY CAVITY THROUGH TUBE, INTO INLET, AND OUT OF OUTLET TO EXTERIOR RESERVOIR — 1904

FIG. 19

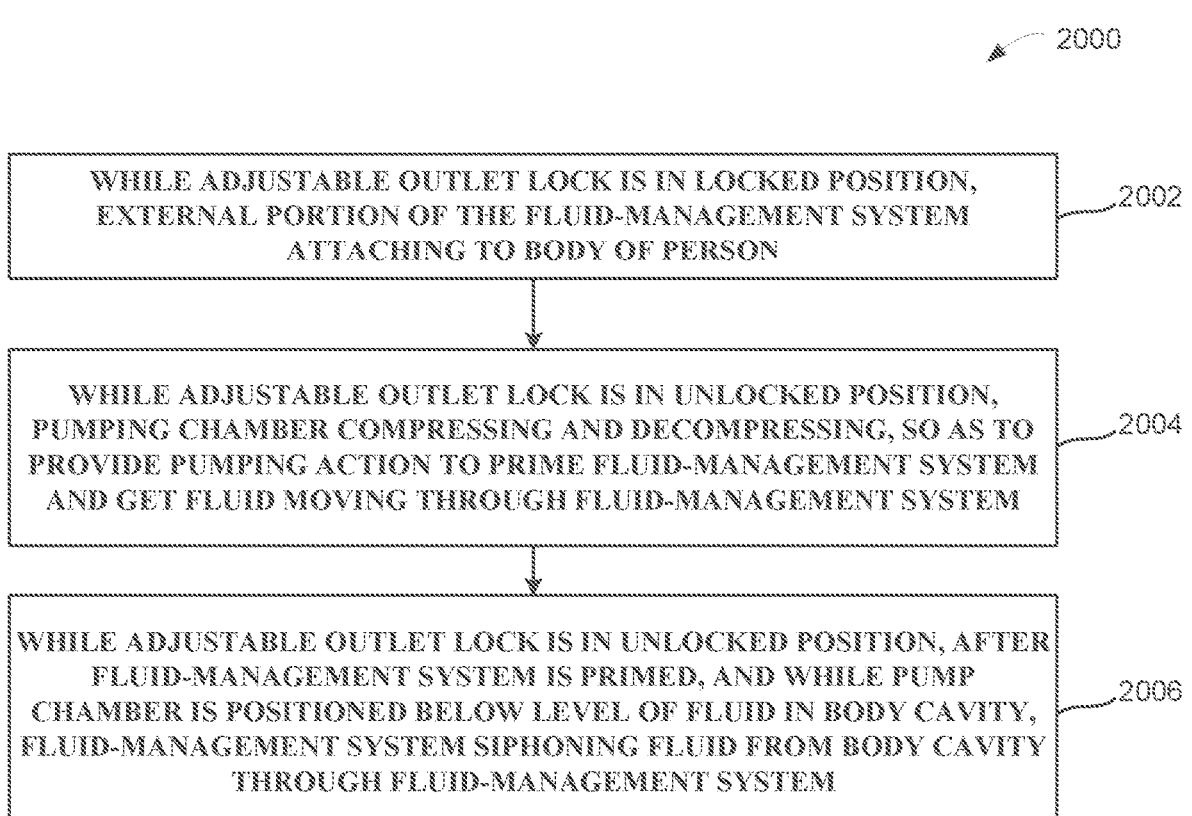

WHILE ADJUSTABLE OUTLET LOCK IS IN LOCKED POSITION, EXTERNAL PORTION OF THE FLUID-MANAGEMENT SYSTEM ATTACHING TO BODY OF PERSON — 2002

WHILE ADJUSTABLE OUTLET LOCK IS IN UNLOCKED POSITION, PUMPING CHAMBER COMPRESSING AND DECOMPRESSING, SO AS TO PROVIDE PUMPING ACTION TO PRIME FLUID-MANAGEMENT SYSTEM AND GET FLUID MOVING THROUGH FLUID-MANAGEMENT SYSTEM — 2004

WHILE ADJUSTABLE OUTLET LOCK IS IN UNLOCKED POSITION, AFTER FLUID-MANAGEMENT SYSTEM IS PRIMED, AND WHILE PUMP CHAMBER IS POSITIONED BELOW LEVEL OF FLUID IN BODY CAVITY, FLUID-MANAGEMENT SYSTEM SIPHONING FLUID FROM BODY CAVITY THROUGH FLUID-MANAGEMENT SYSTEM — 2006

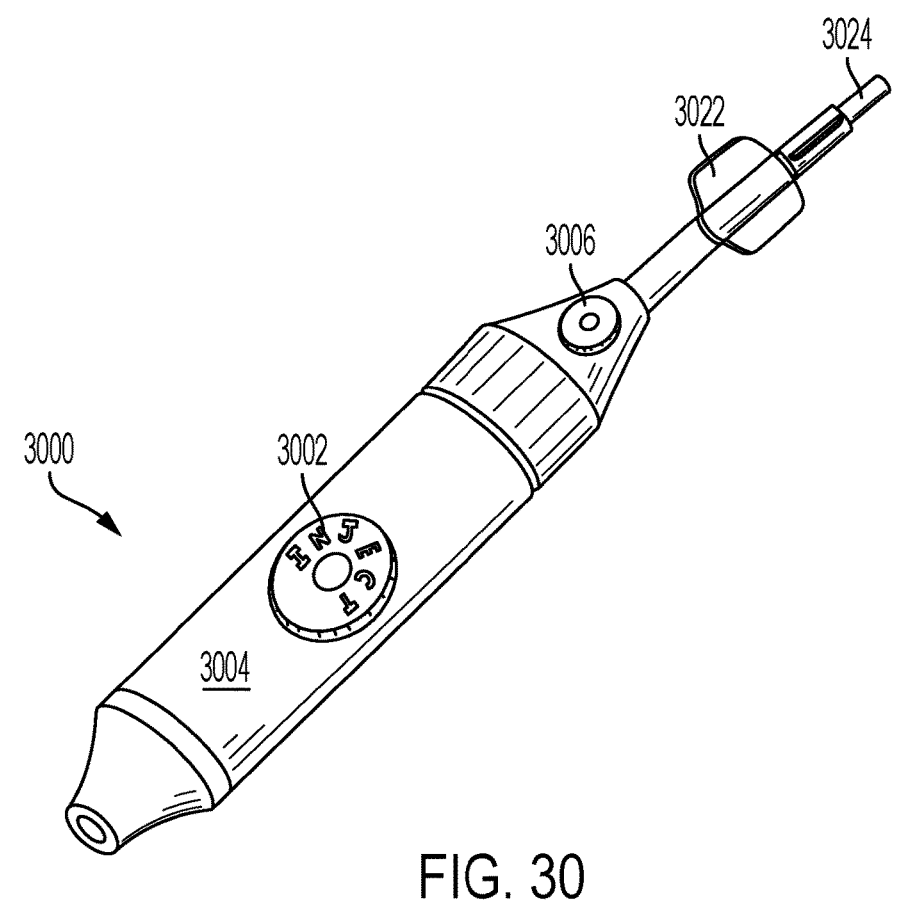
FIG. 30
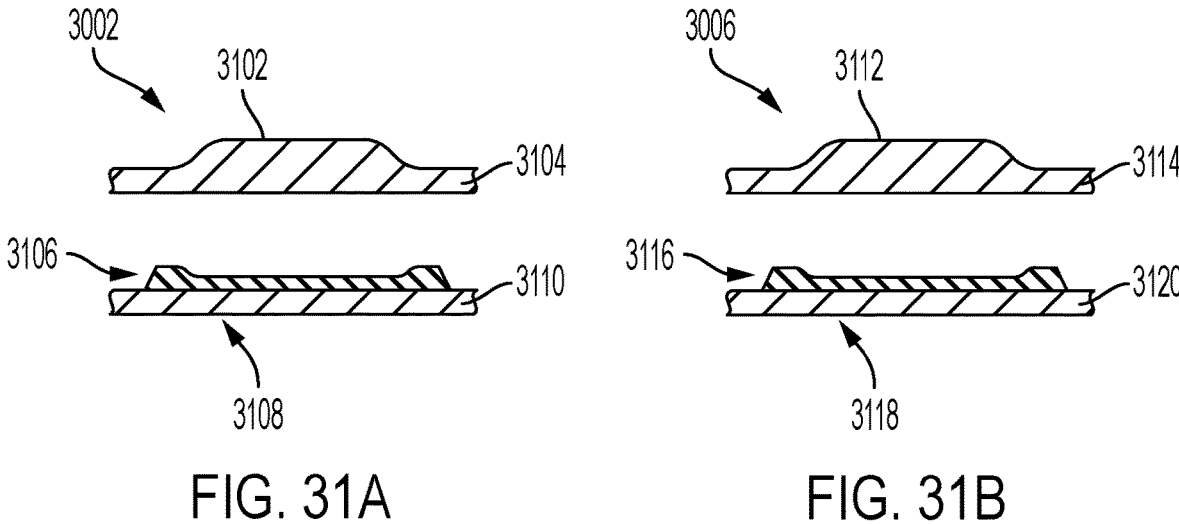
FIG. 31A                    FIG. 31B

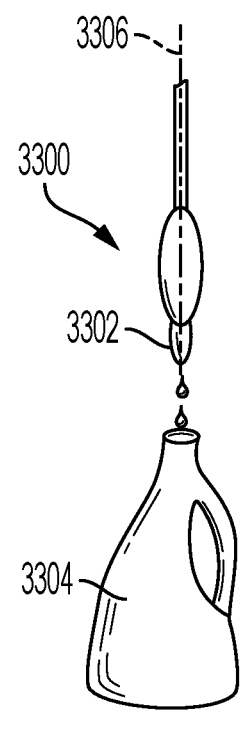
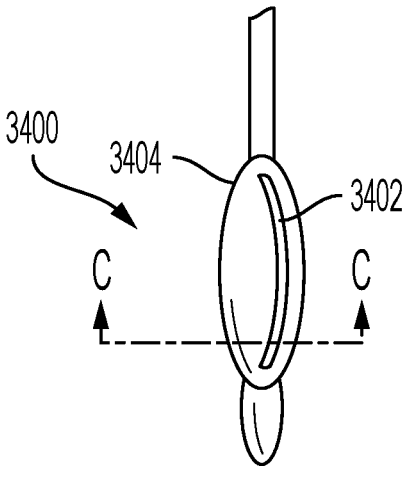
FIG. 33A
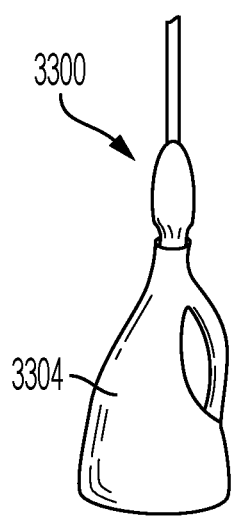
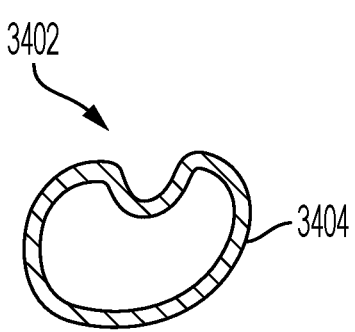
FIG. 33B
FIG. 34A
FIG. 34B

3500

3502

3504

3506

3508

3510

3500

3504

3510

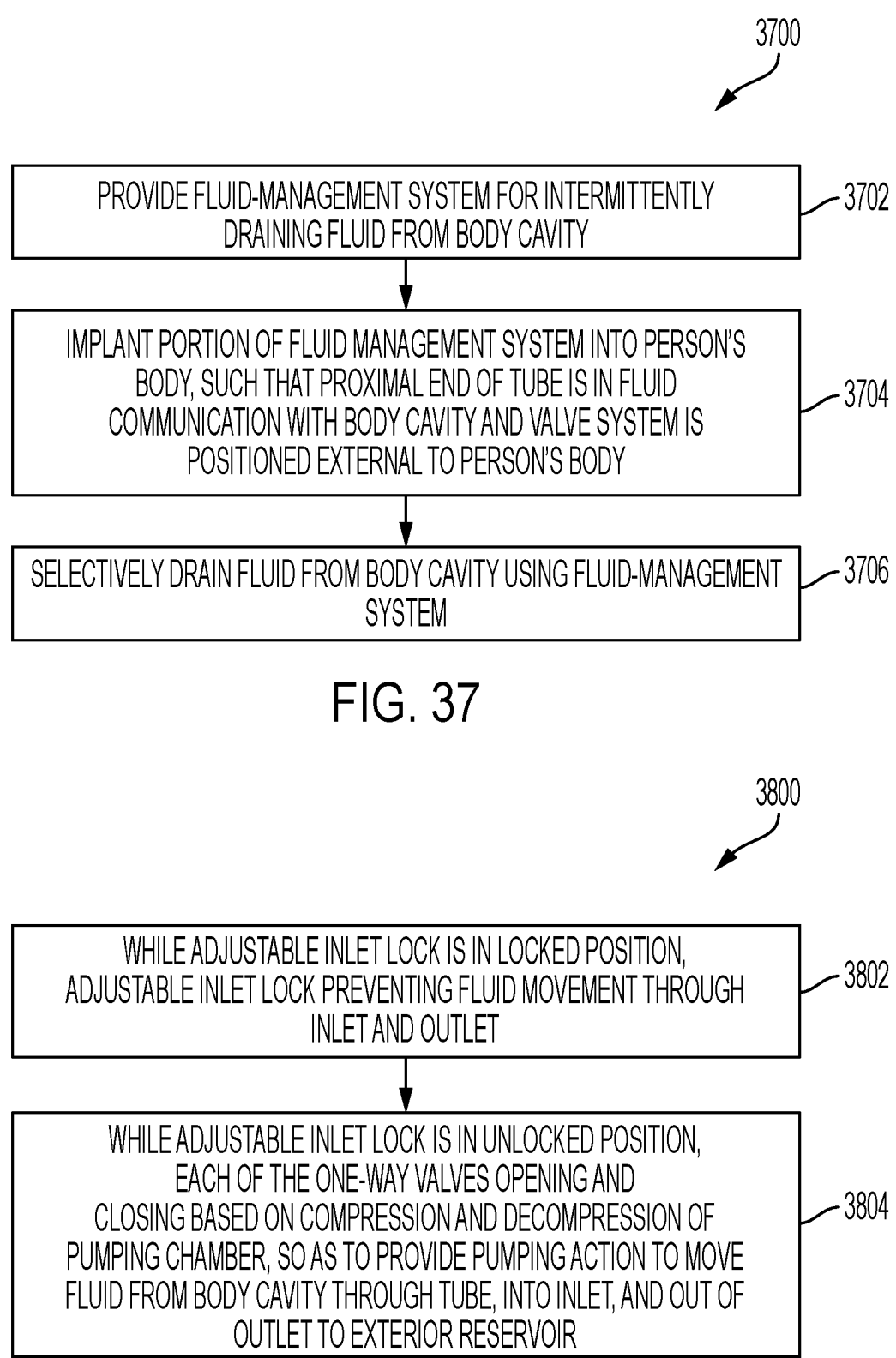

3700

PROVIDE FLUID-MANAGEMENT SYSTEM FOR INTERMITTENTLY DRAINING FLUID FROM BODY CAVITY — 3702

IMPLANT PORTION OF FLUID MANAGEMENT SYSTEM INTO PERSON'S BODY, SUCH THAT PROXIMAL END OF TUBE IS IN FLUID COMMUNICATION WITH BODY CAVITY AND VALVE SYSTEM IS POSITIONED EXTERNAL TO PERSON'S BODY — 3704

SELECTIVELY DRAIN FLUID FROM BODY CAVITY USING FLUID-MANAGEMENT SYSTEM — 3706

WHILE ADJUSTABLE INLET LOCK IS IN LOCKED POSITION, ADJUSTABLE INLET LOCK PREVENTING FLUID MOVEMENT THROUGH INLET AND OUTLET — 3802

WHILE ADJUSTABLE INLET LOCK IS IN UNLOCKED POSITION, EACH OF THE ONE-WAY VALVES OPENING AND CLOSING BASED ON COMPRESSION AND DECOMPRESSION OF PUMPING CHAMBER, SO AS TO PROVIDE PUMPING ACTION TO MOVE FLUID FROM BODY CAVITY THROUGH TUBE, INTO INLET, AND OUT OF OUTLET TO EXTERIOR RESERVOIR — 3804

FIG. 38

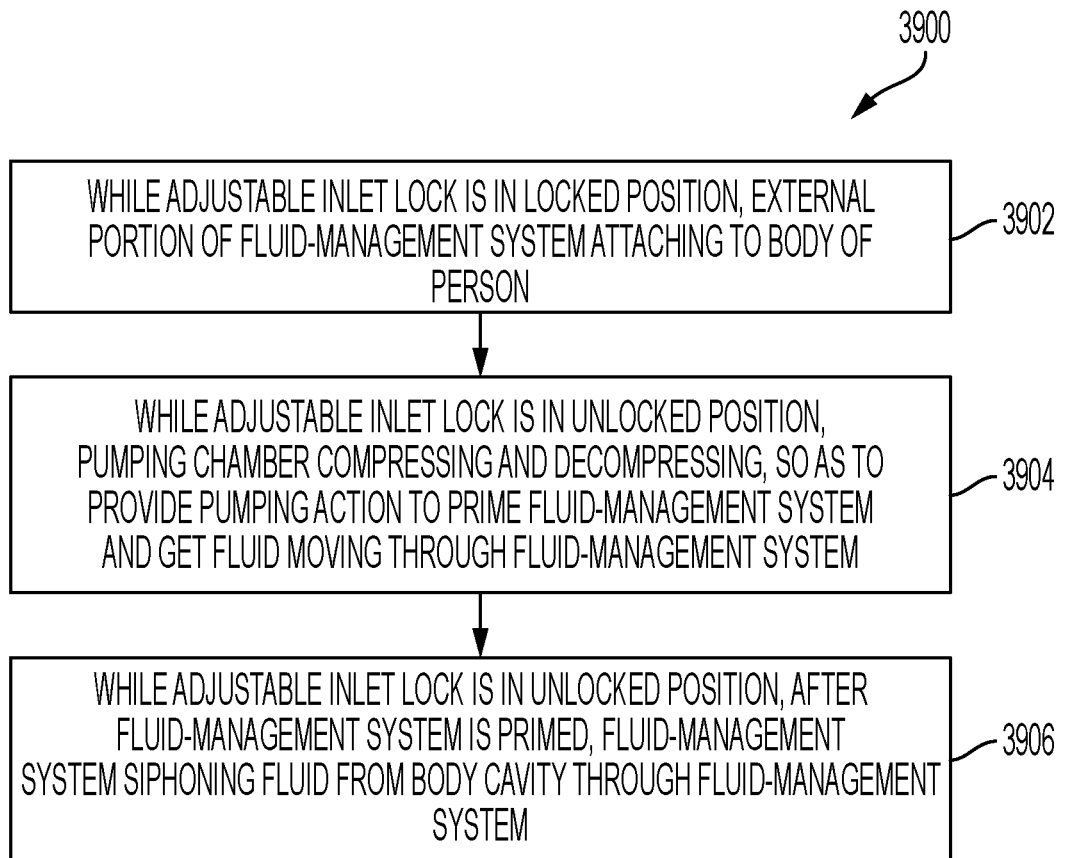

3900

WHILE ADJUSTABLE INLET LOCK IS IN LOCKED POSITION, EXTERNAL PORTION OF FLUID-MANAGEMENT SYSTEM ATTACHING TO BODY OF PERSON — 3902

WHILE ADJUSTABLE INLET LOCK IS IN UNLOCKED POSITION, PUMPING CHAMBER COMPRESSING AND DECOMPRESSING, SO AS TO PROVIDE PUMPING ACTION TO PRIME FLUID-MANAGEMENT SYSTEM AND GET FLUID MOVING THROUGH FLUID-MANAGEMENT SYSTEM — 3904

WHILE ADJUSTABLE INLET LOCK IS IN UNLOCKED POSITION, AFTER FLUID-MANAGEMENT SYSTEM IS PRIMED, FLUID-MANAGEMENT SYSTEM SIPHONING FLUID FROM BODY CAVITY THROUGH FLUID-MANAGEMENT SYSTEM — 3906

FLUID-MANAGEMENT SYSTEM AND METHOD

CROSS-REFERENCE TO RELATED APPLICATIONS

This application is a continuation of, and claims the benefit of priority under 35 U.S.C. § 120 to, U.S. Non-Provisional patent application Ser. No. 18/108,124, filed on Feb. 10, 2023 and titled "Fluid-Management System and Method," which is a continuation-in-part of, and claims the benefit of priority under 35 U.S.C. § 120 to, U.S. Non-Provisional patent application Ser. No. 17/733,138, filed on Apr. 29, 2022 and entitled "Fluid-Management System and Method," the contents of each of which are incorporated herein by reference in its entirety.

BACKGROUND

A number of techniques for draining bodily fluid involve utilizing a pump, in combination with a tube (e.g., a shunt or catheter), to drain fluid from one cavity within the human body to either another cavity within the body or to a reservoir outside of the body. Such techniques may be utilized for purposes including, for example, draining a person's blood, urine, saliva, cerebrospinal fluid, peritoneal fluid, pleural fluid, and/or cystic-lesion fluid, among other possibilities.

OVERVIEW

When fluid builds up in a cavity of a person's body, it is often necessary to drain the fluid to either another cavity within the body or to outside of the body. Fluid may build up for one reason or another in various body cavities such as a pleural cavity, a peritoneal cavity, a cerebrospinal cavity, a breast cavity, a cavity of a cystic lesion in the body (e.g., a cystic lesion in the breast, a cystic lesion in the abdomen, etc.), a cavity left following surgery, among other possibilities.

In some situations, it may be desirable to drain fluid by moving the fluid (i) from a body cavity, (ii) through an implanted tube in fluid communication with the body cavity, and (iii) into an external reservoir located outside the person's body. Further, in some situations, it may also be desirable for a person to not have a permanently-attached external drainage reservoir attached to the implanted tube that is in fluid communication with the body cavity, but rather have the ability to intermittently drain the body cavity into an external drainage reservoir when convenient for the person. Such selective draining of fluid from the body cavity may, for instance, help a person drain fluid build-up before the fluid build-up becomes uncomfortable while also avoiding the need for a permanently-attached external drainage reservoir. Allowing a person to control when to selectively drain fluid and avoiding the need for a permanently-attached external drainage reservoir may provide a person greater freedom and flexibility compared to a situation in which a person is unable to selectively control when to drain fluid and/or has a permanently-attached external drainage reservoir.

One example situation in which it may be desirable to selectively drain fluid from a person's body cavity into an external drainage reservoir that is not permanently attached to the person is drainage of pleural fluid for the treatment of pleural effusions. Pleural fluid is normally a low-protein liquid that can be found in relatively small amounts (normally 10-20 milliliters) in each of a person's pleural cavities. The pleural cavities are the spaces between the visceral pleura (i.e., the membrane located over the entire outer surface of each lung) and the parietal pleura (i.e., the membrane lining the inside of the chest wall of each hemithorax). The small amount of pleural fluid in each pleural space is spread out very thinly between the visceral and parietal pleura thereby providing for a large surface tension which mechanically couples the lung to the chest wall while simultaneously lubricating these surfaces allowing the lung to slide over the chest wall during the breathing process. In a normal, healthy person, pleural fluid is constantly being produced—largely from leakage of fluid from blood and lymphatic vessels in the visceral pleura that coats the outer surface of the lung—and reabsorbed at essentially the same rate by lymphatic channels located in the parietal pleural that lines the chest wall. This dynamic balance exchanges the fluid multiple times a day and typically maintains a low total volume in the 10-20 milliliter range. However, under certain abnormal conditions, such as infection, inflammation, malignancy, heart failure, liver failure, or kidney failure, among other possible conditions, the net flow of pleural fluid within the pleural cavity becomes unbalanced, with increased fluid production and/or decreased reabsorption, resulting in the excess accumulation (e.g., on the order several hundred milliliters to several liters) of fluid in the pleural space.

Excess accumulation of pleural fluid is known as pleural effusion and adds additional mass that must be moved with each breath and may cause the pathological compression of lung tissue. This compression results in considerable difficulty in or prevention of the breathing process. Pleural effusion may lead to various issues, such as dyspnea, shortness of breath, chest pain, and/or chronic cough, among other possibilities, and may greatly compromise a person's quality of life. Draining of the excess accumulation of pleural fluid may help to alleviate, reduce or eliminate such issues. Treatment of a pleural effusion may involve draining of pleural fluid into either another body cavity or outside of the body, and in some situations, it may be desirable to treat a pleural effusion by selectively draining fluid from the pleural cavity into an external reservoir.

While there are certain fluid-management systems existing that allow a person to selectively control when to drain excess fluid from a body cavity (e.g., a pleural cavity) via an implanted tube such that an external reservoir is not always attached to the implanted tube, these existing fluid-management systems typically utilize a dedicated pump-and-reservoir assembly that can be removably attached to the implanted tube. The dedicated pump-and-reservoir assembly includes an active pumping component for pumping fluid out of the body cavity and a drainage reservoir for collecting the pumped fluid. The active pumping component serves to force fluid to move through the implanted tube and into the drainage reservoir. In an example, the active pumping component is a vacuum-based component that is configured to provide vacuum pressure to facilitate draining from the body cavity. For instance, in an example, a dedicated pump-and-reservoir assembly includes a vacuum bottle that, upon attachment to the implanted tube and activation of the vacuum (e.g., via breaking of a vacuum seal of the vacuum bottle), provides vacuum pressure to move fluid from the person's body cavity, through the implanted tube, and into the vacuum bottle.

When a person desires to drain the fluid within the body cavity using a dedicated pump-and-reservoir assembly, the person needs to (i) access the dedicated pump-and-reservoir assembly, (ii) sterilize both the component(s) of the dedicated pump-and-reservoir assembly to be connected to the implanted tube and the attachment point of the implanted tube, (iii) attach the dedicated pump-and-reservoir assembly to the implanted tube, and (iv) activate the active pumping component to facilitate draining of the body cavity. Further, after completing draining of the body cavity, the person then needs to detach the dedicated pump-and-reservoir assembly from the implanted tube, as well as decontaminate and sterilize the attachment point of the implanted tube. However, the existing fluid-management systems such as this that allow a person to selectively control when to drain excess fluid from a body cavity by utilizing a dedicated pump-and-reservoir assembly have numerous drawbacks.

One such drawback of existing fluid-management systems is that a person cannot drain fluid from the body cavity with the implanted tube unless the person has access to the dedicated pump-and-reservoir assembly. However, in practice, it is often difficult and/or inconvenient for a person to always bring with them a dedicated pump-and-reservoir assembly or otherwise ensure that they always have access to the dedicated pump-and-reservoir assembly when needed. For instance, the dedicated pump-and-reservoir assemblies can be bulky and/or difficult transport. Further, people may often forget to bring a dedicated pump-and-reservoir assembly with them (e.g., when leaving the person's house for one reason or another, the person may forget the dedicated pump-and-reservoir assembly and instead leave it at home). Therefore, with the existing fluid-management systems, a person may be unable to drain fluid from the body at the desired or needed time.

Another drawback of existing fluid-management systems is that the dedicated pump-and-reservoir assemblies may be costly and/or difficult for a person to obtain. For instance, the dedicated pump-and-reservoir assemblies may be single-use assemblies that are disposed of after draining, and these may be costly for persons using the assemblies and/or insurance companies for persons using the assemblies. Further, in some examples, the dedicated pump-and-reservoir assembly includes a reusable pumping component (e.g., a reusable motorized peristaltic pump) and a single-use dedicated drainage line and reservoir, and these may be costly for persons using the assemblies and/or insurance companies for persons using the assemblies. Such cost issues may make it difficult for a person to obtain the dedicated pump-and-reservoir assemblies. Further, it may be difficult for a person to always have a dedicated pump-and-reservoir assembly on hand and/or obtain a dedicated pump-and-reservoir assembly when needed. Such issues may in turn reduce compliance with a person's treatment plan (e.g., a doctor-specified draining schedule for draining the body cavity).

Yet another example drawback of existing fluid-management systems is that the process of connecting the dedicated pump-and-reservoir assembly to the implanted tube can be a cumbersome process.

Still yet another example drawback of existing fluid-management systems is that the task of connecting the components(s) of the dedicated pump-and-reservoir assembly to the attachment point of the implanted tube may be associated with a risk of contamination (e.g., if one or more of the components being attached is not sterile). Further, contamination may be associated with a risk of infection, and existing fluid-management systems have a reported infection rate of approximately 5-10%. In existing fluid-management systems, the reservoir and attachment line are typically single-use and provided sterile. The implanted tube to which the reservoir and attachment line are attached is typically decontaminated, for example, with an alcohol swab or betadine swab. The sterile, disposable, attachment line is then connected to this decontaminated portion of the implanted tube. In some existing fluid-management systems, the sterile part is passed through the decontaminate part and into the interior of the implanted tube that is in direct fluid communication with the pleural space. Infection may occur during use of existing fluid-management systems for various reasons, such as bacterial colonization of the implanted tube entry point and/or the distal access of the implanted tube itself. Further, in existing fluid management systems, when the implanted tube is accessed, the systems do not actively prevent retrograde flow (also referred to herein as "backflow") during the draining process, and backflow may be associated with a risk on contamination and/or infection.

To help address the aforementioned and other problems, disclosed herein is new fluid-management system for selectively draining fluid from a body cavity. The disclosed fluid-management system includes a valve assembly and a tube for carrying fluid from a body cavity of a person to the valve assembly. The valve assembly is configured to be positioned external to the person's body and comprises (i) an inlet, (ii) an outlet, (iii) one or more one-way valves positioned between the inlet and outlet that are each configured to open and close based on fluctuations in pressure between the person's body cavity and the one-way valve, and (iv) an adjustable outlet lock configured to selectively prevent fluid movement through the outlet. In some implementations, the one or more one-way valves of the valve assembly may take the form of a single one-way valve, while in other implementations, the one or more one-way valves of the valve assembly may take the form of two one-way valves arranged in series, among other possibilities. In implementations where the one or more one-way valves of the valve assembly take the form of two one-way valves arranged in series, the two one-way valves of the valve assembly may be arranged in series within a pumping chamber that is configured to allow a person to prime the fluid-management system. The tube may be configured to extend from the inlet of the valve assembly to the person's body cavity and allow movement of fluid from the person's body cavity to the inlet of the valve assembly. In this way, the fluid-management system may be selectively used by the person to drain fluid into any appropriate external reservoir, such as a sink, a commode, and/or a container provided by the person, among other possibilities.

As noted, the one or more one-way valves are each configured to open and close based on fluctuations in pressure between the body cavity and the one-way valve, which allows fluid movement out of the outlet and also prevents retrograde flow (also referred to herein as "backflow") in the fluid-management system (e.g., flow of liquid and/or air back into the tube). In practice, retrograde flow may result in aspiration of air back into the body cavity (e.g., a pleural cavity) or flow of liquid back into the cavity, and such retrograde flow could cause various issues such as infection by allowing bacterial entry and/or collapse of the lung. Therefore, preventing retrograde may help to avoid such issues that may be associated with flow of liquid and/or air back into the tube.

Additionally, the opening and closing of the one or more one-way valves may also provide a pumping action that helps move fluid from the cavity through the tube and the valve assembly. In this regard, in some examples, fluctuations in pressure between the body cavity and the one or more one-way valves occur based on respiratory action of a breathing cycle of the person. As one possibility, when the body cavity is the pleural cavity, pressure between the body cavity and the one or more one-way valves swings from positive to negative during the breathing cycle. Based on these fluctuations in pressure between the body cavity and the one or more one-way valves, the one or more one-way valves will close during inspiration (when pressure is negative) and open during expiration (when pressure is positive). As such, in an example, the valve assembly can provide a pump action with energy provided by the respiratory action of the person draining fluid from the body cavity. Given this opening and closing due to respiratory action, the valve assembly can act as a pump to move fluid from the body cavity, through the tube, through the one or more one-way valves, and out the outlet.

In at least some implementations, the one or more one-way valves may each be configured to have a low "cracking pressure," such that the one-way valve is configured to transition from a closed state to an open state with relatively small differential pressures across the one-way valve. For instance, the cracking pressure of each one-way valve can range anywhere from about 25 $cmH_2O$ or less to about 5 $cmH_2O$ or less, and as specific examples, the cracking pressure of a given one-way valve could be less than about 25 $cmH_2O$, less than about 15 $cmH_2O$, less than about 10 $cmH_2O$, or less than about 5 $cmH_2O$. Further, in at least some implementations, the one or more one-way valves may also each be configured to have a low "resealing pressure," such that the one-way valve is configured to transition from an open state to a closed state with small differential pressures across the one-way valve. For instance, the resealing pressure of each one-way valve can range anywhere from about 15 $cmH_2O$ or less to about 2 $cmH_2O$ or less, and as specific examples, the cracking pressure of a given one-way valve could be less than about 15 $cmH_2O$, less than about 10 $cmH_2O$, less than about 5 $cmH_2O$, or less than about 2 $cmH_2O$.

Further yet, the cracking pressure and/or the resealing pressure for each of the one or more one-way valves may be selected based on any of various factors, an example of which may be the type of cavity from which the fluid-management system is intended to drain fluid, among other examples.

In operation, prior to draining the body cavity using the disclosed fluid-management system, a person may first select an external reservoir in which to drain the fluid from the body, such as a sink, a commode, and/or a container provided by the person, among other possibilities. Next, to initiate the draining process, the person may switch the adjustable outlet lock of the valve assembly to an unlocked position. When the adjustable outlet lock is in the unlocked position, fluid may begin moving through the fluid-management system due to the pressure of the body cavity and/or the pumping action provided by the valve assembly. This will move fluid from the cavity, through the tube extending from the cavity to the inlet of the system, through the one or more one-way valves of the system, and then out of the outlet of the system and into the external reservoir. After the draining process has begun, the person may drain the fluid from the cavity until the cavity is empty and/or a desired amount of fluid has been drained from the cavity. Finally, after draining is complete, the person may decontaminate the outlet and/or adjustable lock of the valve assembly and switch the adjustable lock into the locked position. Alternatively, the adjustable lock could be a locking cap that can be attached to the catheter assembly to seal the valve assembly and prevent fluid flow or removed to allow fluid flow. At the conclusion the cap can be decontaminated and reattached or a new cap can be attached.

The disclosed fluid-management system may also be designed such that, when a sufficient amount of fluid has moved through the fluid-management system, a siphon effect can be utilized to help to more quickly drain the fluid from the cavity. For instance, the disclosed fluid-management system may be designed such that the pressure of the body cavity and/or pumping action provided by the valve assembly may allow a column of fluid to form within the tube that in turn leads to a siphon effect. The height of this column of fluid can be increased by the patient sitting up or standing or by lowering the distal end of the tube. In other words, the disclosed fluid-management system may be designed such that, once the tube is primed by the valve assembly, fluid from the cavity can be siphoned out.

As mentioned above, in some implementations, the one or more one-way valves of the valve assembly may take the form of a single one-way valve, whereas in other implementations, the one or more one-way valves of the valve assembly may take the form of two one-way valves arranged in series. As also mentioned above, in either of these arrangements, the one or more one-way valves are each configured to open and close based on fluctuations in pressure between a cavity of a person's body and the one-way valve, or fluctuations in pressure between a cavity of a person's body and the first one-way valve and fluctuations in pressure between the first one-way valve and the second one-way valve. Furthermore, in implementations where the one or more one-way valves of the valve assembly take the form of two one-way valves arranged in series, the two one-way valves may allow for additional capabilities and/or benefits relative to a valve assembly having a single one-way valve, including but not limited to improving the flow of fluid movement in the fluid-management system (e.g., when used together with a pumping chamber) and/or providing an additional barrier to retrograde flow, among other possibilities.

For instance, in at least some implementations, the two one-way valves of the valve assembly may be arranged in series within a pumping chamber, where a first one-way valve may be positioned on a first side of the pumping chamber proximate to the inlet of the valve assembly and a second one-way valve may be positioned on a second side of the pumping chamber proximate to the outlet of the valve assembly. Such a pumping chamber may be formed from a resiliently flexible material that may be compressed and decompressed to provide a pumping action to prime the fluid-management system and get fluid moving through the fluid-management system. In this respect, cyclical compression and decompression of the resiliently flexible material may draw fluid (e.g., liquid and/or air) from the inlet, through the first one-way valve into an interior space of the pumping chamber, through the second one-way valve, and out the outlet of the valve assembly. Such a two-valve configuration may thus allow a person to prime the fluid-management system, which may help to speed up the draining process by getting fluid to move more quickly through the fluid-management system. Such a two-valve configuration may also allow for the generation of supra-physiologic positive and/or negative pressures, which may also be of benefit to clear debris from within the tubing, from within the one-way valves, and/or from within other regions of the valve assembly.

Further, in at least some implementations, the fluid-management system includes a valve assembly and a tube for carrying fluid from a body cavity of a person to the valve assembly, wherein the valve assembly is configured to be positioned external to the person's body and comprises (i) an inlet, (ii) an outlet, (iii) a pumping chamber between the inlet and outlet and configured to be compressed and decompressed to pump fluid, (iv) a first one-way valve positioned on a first side of the pumping chamber, (v) a second one-way valve positioned on a second side of the pumping chamber, and (vi) an adjustable inlet lock configured to selectively prevent fluid movement through the inlet, and wherein the tube is configured to extend from the inlet of the valve assembly to the person's body cavity.

Still further, in at least some implementations, the fluid-management system includes a valve assembly and a tube for carrying fluid from a body cavity of a person to the valve assembly, wherein the valve assembly is configured to be positioned external to the person's body and comprises (i) an inlet, (ii) an outlet, (iii) a pumping chamber between the inlet and outlet and configured to be compressed and decompressed to pump fluid, (iv) a first one-way valve positioned on a first side of the pumping chamber, (v) a second one-way valve positioned on a second side of the pumping chamber, (vi) an adjustable inlet lock configured to selectively prevent fluid movement through the inlet, and wherein the tube is configured to extend from the inlet of the valve assembly to the person's body cavity, and (vii) an adjustable outlet lock configured to selectively prevent fluid movement through the outlet, wherein the adjustable inlet lock is positioned upstream of the first one-way valve, and wherein the adjustable outlet lock is positioned downstream of the second one-way valve.

The fluid-management system (and method of operation) disclosed herein may provide various benefits over existing fluid-management systems that allow a person to selectively control when to drain excess fluid from a body cavity to an external reservoir, such as a fluid-management system that is based on a dedicated pump-and-reservoir assembly.

For instance, the valve assembly of the disclosed fluid-management system is configured to leverage pressure gradients produced with respect to the body cavity and the valve system to drain fluid from the body cavity rather than relying on an active, vacuum-based pumping component (which involves larger, heavier, and more expensive components). Further, the valve assembly of the disclosed fluid-management system is not integrated into a dedicated pump-and-reservoir assembly and can be used to drain fluid from the body cavity into any available reservoir at any time. As a result, the disclosed fluid-management system is smaller, lighter, and more portable than existing fluid-management systems. The fluid-management system can thus remain with the person at all times (e.g., the external portion of the fluid-management system can be coiled and taped to a person's body or tucked into clothing when not in use) and does not require that the person have access to a dedicated pumping-and-reservoir assembly.

Further, given that the fluid-management system does not rely of an active, vacuum-based component and is not integrated into a dedicated pump-and-reservoir assembly, the disclosed fluid-management system is less costly (e.g., for persons using the assemblies and/or insurance companies for persons using the assemblies) than existing fluid-management systems.

Still further, by avoiding the need to attach a dedicated pump-and-reservoir assembly to the implanted tube and also detach the dedicated pump-and-reservoir assembly from the implanted tube each time a person drains the body cavity, the draining process using the disclosed fluid-management system is less cumbersome compared to draining processes using the existing fluid-management systems.

Yet still further, as noted above, the existing draining processes involve connecting components(s) of the dedicated pump-and-reservoir assembly to the attachment point of the implanted tube, which may be associated with a risk of contamination (e.g., if one or more of the components being attached is not sterile). By avoiding the need to attach a dedicated pump-and-reservoir assembly to the implanted tube and also detach the dedicated pump-and-reservoir assembly from the implanted tube each time a person drains the body cavity, the disclosed fluid-management system also reduces a risk of contamination compared to the existing fluid-management systems. And yet still further, as noted above, in existing fluid management systems, when the implanted tube is accessed, the systems do not actively prevent backflow during the draining process. The disclosed fluid-management system includes one or more one-way valves configured to prevent backflow in the fluid-management system both during the draining process as well as when the adjustable outlet lock is closed. Actively preventing backflow reduces a risk of contamination and/or infection compared to the existing fluid-management systems.

Accordingly, in one aspect, disclosed herein is a fluid-management system comprising a valve assembly and a tube for carrying fluid from a body cavity of a person to the valve assembly. The valve assembly is configured to be positioned external to the person's body and comprises (i) an inlet, (ii) an outlet, (iii) one or more one-way valves positioned between the inlet and outlet that are each configured to open and close based on fluctuations in pressure between the person's body cavity and the one-way valve, and (iv) an adjustable outlet lock configured to selectively prevent fluid movement through the outlet.

In another aspect, disclosed herein is a fluid-management system comprising a valve assembly and a tube for carrying fluid from a body cavity of a person to the valve assembly. The valve assembly is configured to be positioned external to the person's body and comprises (i) an inlet, (ii) an outlet, (iii) a plurality of one-way valves positioned between the inlet and outlet that are each configured to open and close based on fluctuations in pressure between the person's body cavity and the one-way valve, and (iv) an adjustable outlet lock configured to selectively prevent fluid movement through the outlet. In at least some implementations, the plurality of one-way valves may be arranged in series. Further, the tube is configured to extend from the inlet of the valve assembly to the person's body cavity.

In yet another aspect, disclosed herein is a method of operation of a fluid-management system comprising a valve assembly and a tube for carrying fluid from a body cavity of a person to the valve assembly. The valve assembly is positioned external to the person's body and comprises (i) an inlet, (ii) an outlet, (iii) one or more one-way valves positioned between the inlet and outlet that are each configured to open and close based on fluctuations in pressure between the person's body cavity and the one-way valve, and (iv) an adjustable outlet lock configured to selectively prevent fluid movement through the outlet. The method includes while the adjustable outlet lock is in a locked position, the adjustable outlet lock preventing fluid movement through the outlet. The method further includes while the adjustable outlet lock is in an unlocked position, each of the one or more one-way valves opening and closing based on fluctuations in pressure between the person's body cavity and the one-way valve, so as to provide a pumping action to move fluid from the body cavity through the tube, into the inlet, and out of the outlet to an exterior reservoir. In at least some implementations, the fluctuations occur based on respiratory action of a breathing cycle of the person.

In still yet another aspect, disclosed herein is a method for fluid management that includes providing a fluid-management system comprising a valve assembly and a tube for carrying fluid from a body cavity of a person to the valve assembly, where the valve assembly is configured to be positioned external to the person's body and comprises (i) an inlet, (ii) an outlet, (iii) one or more one-way valves positioned between the inlet and outlet that are each configured to open and close based on fluctuations in pressure between a cavity of a person's body and the one-way valve, and (iv) an adjustable outlet lock configured to selectively prevent fluid movement through the outlet. The method further includes implanting a portion of the fluid-management system into the person's body, such that a proximal end of the tube is in fluid communication with the cavity and the valve assembly is positioned external to the person's body.

In still yet another aspect, disclosed herein is a fluid-management system comprising a valve assembly and a tube for carrying fluid from a body cavity of a person to the valve assembly. The valve assembly is configured to be positioned external to the person's body and comprises (i) an inlet, (ii) an outlet, (iii) a pumping chamber between the inlet and outlet and configured to be compressed and decompressed to pump fluid, (iv) a first one-way valve positioned on a first side of the pumping chamber, (v) a second one-way valve positioned on a second side of the pumping chamber, and (vi) an adjustable inlet lock configured to selectively prevent fluid movement through the inlet, and wherein the tube is configured to extend from the inlet of the valve assembly to the person's body cavity.

In still yet another aspect, disclosed herein is a fluid-management system comprising a valve assembly and a tube for carrying fluid from a body cavity of a person to the valve assembly. The valve assembly is configured to be positioned external to the person's body and comprises (i) an inlet, (ii) an outlet, (iii) a pumping chamber between the inlet and outlet and configured to be compressed and decompressed to pump fluid, (iv) a first one-way valve positioned on a first side of the pumping chamber, (v) a second one-way valve positioned on a second side of the pumping chamber, (vi) an adjustable inlet lock configured to selectively prevent fluid movement through the inlet, and wherein the tube is configured to extend from the inlet of the valve assembly to the person's body cavity, and (vii) an adjustable outlet lock configured to selectively prevent fluid movement through the outlet, wherein the adjustable inlet lock is positioned upstream of the first one-way valve, and wherein the adjustable outlet lock is positioned downstream of the second one-way valve.

In still yet another aspect, disclosed herein is a method of operation of a fluid-management system comprising a valve assembly and a tube for carrying fluid from a body cavity of a person to the valve assembly, wherein the valve assembly is positioned external to the person's body and comprises (i) an inlet, (ii) an outlet, (iii) a pumping chamber between the inlet and outlet and configured to be compressed and decompressed to pump fluid, (iv) a first one-way valve positioned on a first side of the pumping chamber, (v) a second one-way valve positioned on a second side of the pumping chamber, and (vi) an adjustable inlet lock configured to selectively prevent fluid movement through the inlet, and wherein the tube is configured to extend from the inlet of the valve assembly to the person's body cavity. The method includes, while the adjustable inlet lock is in a locked position, an external portion of the fluid-management system attaching to a body of the person. The method further includes, while the adjustable inlet lock is in an unlocked position, (i) the pumping chamber compressing and decompressing, so as to provide a pumping action to prime the fluid-management system and get fluid moving through the fluid-management system and (ii) after the fluid-management system is primed, the fluid-management system siphoning fluid from the body cavity through the fluid-management system.

One of ordinary skill in the art will appreciate these as well as numerous other aspects in reading the following disclosure.

BRIEF DESCRIPTION OF THE DRAWINGS

FIGS. 8A-D illustrate an example adjustable outlet lock, according to an example of the present disclosure.

FIGS. 9A-C illustrate an example adjustable outlet lock, according to an example of the present disclosure.

FIGS. 10A-B illustrate an example adjustable outlet lock, according to an example of the present disclosure.

FIG. 18 shows an example method fluid management, according to an example of the present disclosure.

FIG. 19 shows an example method of draining fluid from a body cavity of a person to a reservoir external to the person's body, according to an example of the present disclosure.

FIG. 20 shows an example method of draining fluid from a body cavity of a person to a reservoir external to the person's body, according to an example of the present disclosure.

FIG. 30 illustrates an example valve assembly, according to an example of the present disclosure.

FIG. 31A illustrates a cross sectional view of the pumping chamber access port of the example valve assembly of FIG. 30, according to an example of the present disclosure.

FIG. 31B illustrates a cross sectional view of the inlet access port of the example valve assembly of FIG. 30, according to an example of the present disclosure.

FIGS. 33A-B illustrate an example valve assembly draining into a bottle, according to an example of the present disclosure.

FIG. 34A illustrates an example valve assembly, according to an example of the present disclosure.

FIG. 34B illustrates a cross sectional view of a body of the pumping chamber of the example valve assembly of FIG. 34A, according to an example of the present disclosure.

FIG. 37 shows an example fluid-management method, according to an example of the present disclosure.

FIG. 38 shows an example method of draining fluid from a body cavity of a person to a reservoir external to the person's body, according to an example of the present disclosure.

FIG. 39 shows an example method of draining fluid from a body cavity of a person to a reservoir external to the person's body, according to an example of the present disclosure.

DETAILED DESCRIPTION

The following disclosure makes reference to the accompanying figures and several example embodiments. One of ordinary skill in the art should understand that such references are for the purpose of explanation only and are therefore not meant to be limiting. Part or all of the disclosed systems, devices, and methods may be rearranged, combined, added to, and/or removed in a variety of manners, each of which is contemplated herein.

As mentioned above, current fluid-management systems and methods that allow a person to selectively control when to drain excess fluid from a body cavity such that such that an external reservoir is not always attached to the implanted tube that is in fluid communication with the body cavity have numerous drawbacks. The fluid-management methods and systems in accordance with the present disclosure beneficially provide improved methods and systems for draining fluid from a body cavity to an external reservoir. In particular, the methods and systems in accordance with the present disclosure beneficially provide for avoiding a need to attach a dedicated pump-and-reservoir assembly that includes an active pumping component for pumping fluid out of the body cavity and a drainage reservoir for collecting the pumped fluid. Rather, in accordance with the present disclosure, the components to initiate draining safely and effectively are on the person at all times, such that the person can selectively drain the body cavity.

In one example, a fluid-management system for selectively draining fluid from a body cavity includes a valve assembly and a tube for carrying fluid from a body cavity of a person to the valve assembly. The valve assembly is configured to be positioned external to the person's body and comprises (i) an inlet, (ii) an outlet, (iii) one or more one-way valves positioned between the inlet and outlet that are each configured to open and close based on fluctuations in pressure between the person's body cavity and the one-way valve, and (iv) an adjustable outlet lock configured to selectively prevent fluid movement through the outlet. The fluid-management system may be used by a person to drain fluid into any appropriate external reservoir. Body fluid to be drained may comprise liquid, gas, or a combination of liquid and gas.

Figure 1B:
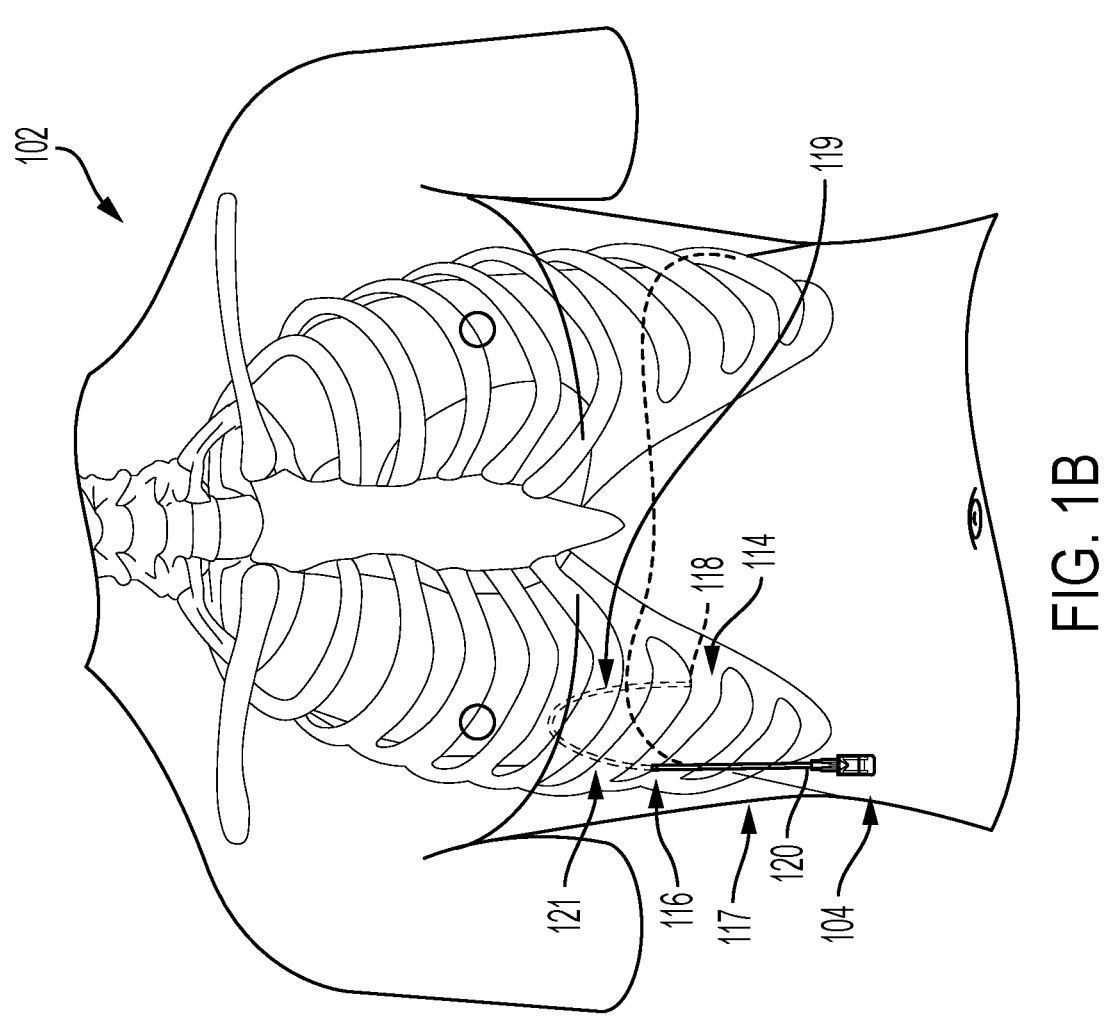
FIG. 1B illustrates the example fluid-management system of FIG. 1A implanted in a person.
Figure 1A:
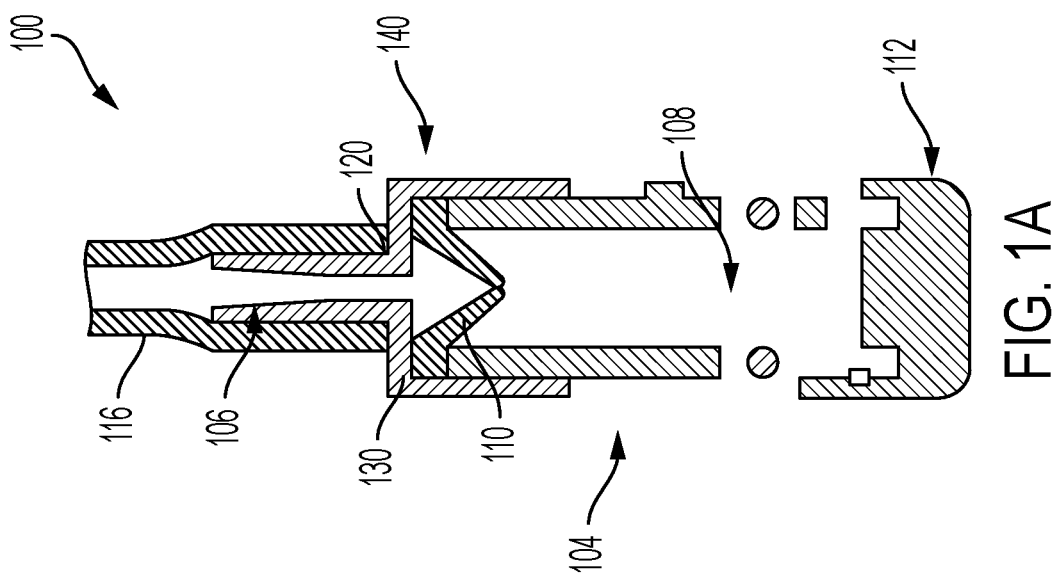
FIG. 1A illustrates an example fluid-management system, according to an example of the present disclosure.

Turning now to the figures, FIG. 1A depicts an example fluid-management system 100, and FIG. 1B depicts the fluid-management system 100 implanted in a person's body 102. Fluid-management system 100 includes a valve assembly 104 having an inlet 106, an outlet 108, a one-way valve 110, and an adjustable outlet lock 112. One-way valve 110 is positioned between inlet 106 and outlet 108 and is configured to open and close based on fluctuations in pressure between cavity 114 and one-way valve 110. Fluid-management system 100 also includes a fluid-management tube 116 for carrying fluid from cavity 114 to valve assembly 104. Tube 116 is configured to extend from inlet 106 to cavity 114 and allow movement of fluid from cavity 114 to inlet 106 of valve assembly 104. Tube 116 is implanted in person's body 102, such that a proximal end 118 of tube 116 is positioned within cavity 114 and a distal end 120 of tube

116 is positioned external to body 102. Further, valve assembly 104 is positioned external to the person's body 102. In particular, with reference to FIG. 1A, external portion 117 of fluid-management system 100 is positioned external to person's body 102. Further, in the example illustrated, the internal portion of fluid-management system 100 includes a first portion 119 of tube 116 positioned behind the ribs and within cavity 114, a second portion 121 of tube 116 positioned in front of the ribs within person's body 102. Other example arrangements of the inner and external portions of fluid-management system 100 are possible as well.

One-way valve 110 includes a one-way valve frame 130 enclosing and providing structure and support to one-way valve 110. Further, one-way valve frame 130 may also serve to connect to distal end 120 of tube 116. The size and shape of the one-way valve frame 130 can be designed to provide joining points or interconnectable joints to tube 116. In an example, valve assembly 104 is non-removably attached to tube 116. As used herein, the term "non-removably attached" means that a first component (e.g., the valve assembly) is intended not to be removed from a second component (e.g., the tube) during normal use and cannot be readily removed from the second component without the use of extraordinary force and/or tools.

Cavity 114 may be a cavity in person's body 102 that may build up fluid for which there is a desire or need to selectively drain out of the body. In the example of FIG. 1A, cavity 114 is a pleural cavity of person's body 102. However, other body cavities are possible, such as a peritoneal cavity, a cerebrospinal cavity, a pericardial cavity, a breast cavity, or a cavity of a cystic lesion, among other possibilities.

Adjustable outlet lock 112 is configured to selectively prevent fluid movement through outlet 108. In particular, adjustable outlet lock 112 is configured to move between a locked position in which adjustable outlet lock 112 seals outlet 108 and an unlocked position in which the adjustable outlet lock 112 allows fluid movement through outlet 108. Adjustable outlet lock 112 may be controlled by a person such that the person may keep adjustable outlet lock 112 in the locked position when not draining cavity 114. Further, the person may switch adjustable outlet lock 112 to the unlocked position when the person wishes to drain cavity 114.

In the example of FIG. 1A, adjustable outlet lock 112 is located at outlet 108 and is configured to cover outlet 108 when in the locked position. However, adjustable outlet lock 112 may be located in other positions, such as upstream of outlet 108. Further, in the example of FIG. 1A, adjustable outlet lock 112 takes the form of a cap and is locked by securely attaching the cap to outlet 108. In particular, the locked position of the cap corresponds to the cap being attached to outlet 108 (as seen in FIG. 1B), and the unlocked position corresponds to the cap being unattached from outlet 108 (as seen in FIG. 1A). Other adjustable outlet locks are possible, some examples of which are described in greater detail below.

As mentioned above, one-way valve 110 is configured to open and close based on fluctuations in pressure between cavity 114 of person's body 112 and one-way valve 110. By opening and closing based on fluctuations in pressure between cavity 114 and one-way valve 110, one-way valve 110 is able to allow fluid movement out of outlet 108 and also prevent retrograde flow (also referred to herein as "backflow") in fluid-management system 100 (e.g., flow of liquid and/or air back into tube 116). In practice, retrograde flow may result in aspiration of air back into cavity 114 (e.g., a pleural cavity) or flow of liquid back into the cavity 114, and such retrograde flow could cause various issues such as infection and/or collapse of the lung. Therefore, preventing backflow may help to avoid such issues that may be associated with flow of liquid and/or air back into tube 116. Further, in some examples, opening and closing of one-way valve 110 may also provide a pumping action that helps move fluid from cavity 114 and through tube 116 and valve assembly 104.

Figures 2A, 2B:
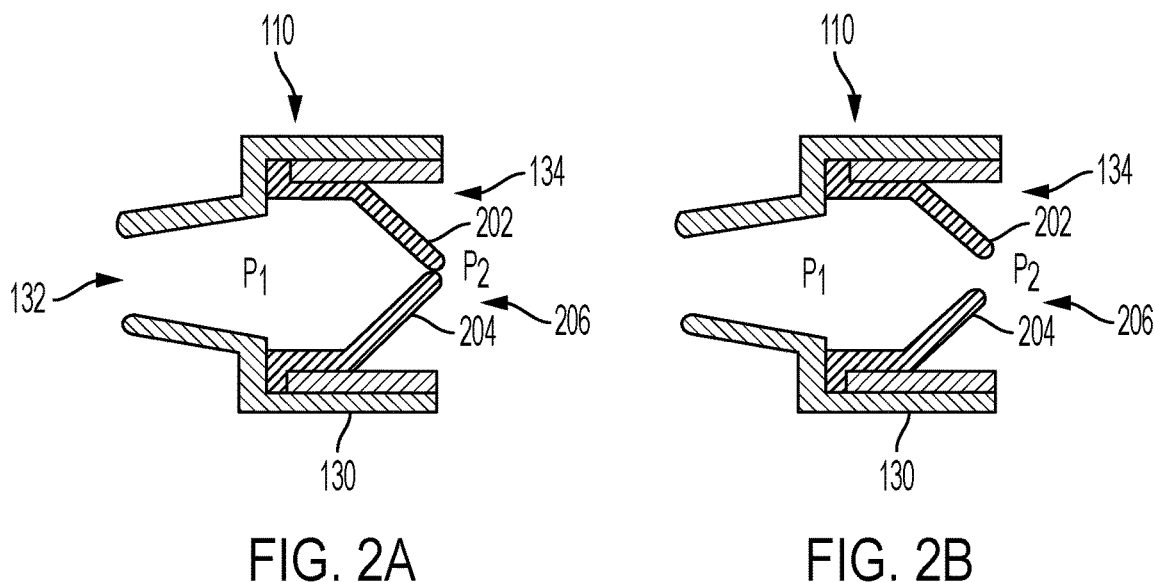
FIG. 2A illustrates a cross-sectional schematic view of a one-way valve in a closed state.
FIG. 2B illustrates a cross-sectional schematic view of a one-way valve in an open state.

Opening and closing of one-way valve 110 is generally described with respect to FIGS. 2a-b. FIG. 2a shows one-way valve 110 in a closed state, whereas FIG. 2b shows one-way valve 110 in an open state. When one-way valve 110 is in a closed position as shown in FIG. 2a, the pressure differential across valve 110 is such that $P_1 \leq P_2 + P_C$, where $P_1$ is the pressure on a first side 132 of one-way valve 110, $P_2$ is the pressure on a second side 134 of one-way valve 110, and $P_C$ is the cracking pressure of one-way valve 110. Similarly, when one-way valve 110 is in an open position as shown in FIG. 2b, the pressure differential across valve 110 is such that $P_1 > P_2 + P_C$, where $P_1$ is the pressure on first side 132 of one-way valve 110, $P_2$ is the pressure on second side 134 of one-way valve 110, and $P_C$ is the cracking pressure of one-way valve 110. In this instance, with $P_1 > P_2 + P_C$, fluid would flow from first side 132 through one-way valve 110 to second side 134.

In an example, one-way valve 110 may be configured to have a low cracking pressure, such that the one-way valve is configured to transition from a closed state to an open state with relatively small differential pressures across the one-way valve. For instance, the cracking pressure of one-way valve 110 can range anywhere from about 25 cmH$_2$O or less to about 5 cmH$_2$O or less, and as specific examples, the cracking pressure of a given one-way valve could be less than about 25 cmH$_2$O, less than about 15 cmH$_2$O, less than about 10 cmH$_2$O, or less than about 5 cmH$_2$O. Further, in an example, one-way valve 110 may be configured to have a low resealing pressure, such that the one-way valve is configured to transition from an open state to a closed state with small differential pressures across the one-way valve. For instance, the resealing pressure of one-way valve 110 can range anywhere from about 15 cmH$_2$O or less to about 2 cmH$_2$O or less, and as specific examples, the cracking pressure of a given one-way valve could be less than about 15 cmH$_2$O, less than about 10 cmH$_2$O, less than about 5 cmH$_2$O, or less than about 2 cmH$_2$O.

Further yet, the cracking pressure and/or the resealing pressure for one-way valve 110 may be selected based on any of various factors, an example of which may be the type of cavity from which the fluid-management system is intended to drain fluid, among other examples. For instance, as one possibility, in situations where pressures vary from low positive to low negative (e.g., pleural cavity), the cracking pressure and/or the resealing pressure may be kept lower than in situations in which pressures tend to remain positive (e.g., peritoneal cavity). As another possibility, in situations where pressures in a cavity tend to remain positive but it is desired to not let fluid volume drop to zero, the valve cracking pressure may be selected at a level configured to keep fluid in the cavity. For example, for the cerebospinal cavity, the cerebospinal cavity tends to remain positive pressure but it is desirable to not let cerebrospinal fluid (CSF) drop to zero. Thus, for the cerebospinal cavity, the valve cracking pressure may be set to a desirable level that will keep the fluid pressure in that space from dropping below the desired cracking pressure and would keep CSF in the cerebospinal cavity.

In an example, one-way valve 110 may include a plurality of lips that define a slit that can move from a closed position to an open position. For instance, with reference to FIGS. 2A-B, one-way valve 110 may include first lip 202 and second lip 204 that define slit 206. The lips 202 and 204 may be configured such that, when the lips are in the closed position, the surface area of interaction between the lips is relatively small. For instance, in an example, the surface area of interaction is below 60 mm$^2$ and preferably in a range 0.6 mm$^2$ to 6 mm$^2$. A surface area in this range may help ensure that the one-way valve works well both when wet and dry. As the surface area of interaction of valve lips becomes large (e.g., larger than 60 mm$^2$), significant cohesive and adhesive forces may develop between the liquid and the two surfaces when the lips are wetted, thereby making it more difficult for the valve to open. This force required to separate the two surfaces of the valve lips is given by the relationship, $$F = \frac{2 \cdot T \cdot A}{h},$$

where F=the force required to separate the lips, T is the surface tension of the wetting liquid (T=70 for water at 37° C.), A is the area of the interface between the lips and h is the thickness of the liquid layer between the lips.

In the example of FIGS. 2A-2B, one-way valve 110 is formed as a duckbill valve. However, other types and/or shapes of valves are possible as well, including, for instance, a flapper valve and a cross-slit valve, among other possibilities.

Further, in an example, one-way valve 110 is configured such that, when in the open state, the opening is larger than the lumen of tube 116. Such a configuration may help to ensure that any debris that can get into the tube can clear through the valve. In some examples, the opening at proximal end 118 of tube 116 is smaller than the lumen of tube 116, the lumen of tube 116 is smaller than the opening of one-way valve 110 when it is in the open state, and the opening of one-way valve 110 when it is in the open state in turn is smaller than the lumen of outlet 108. Other examples are possible as well.

Figure 3:
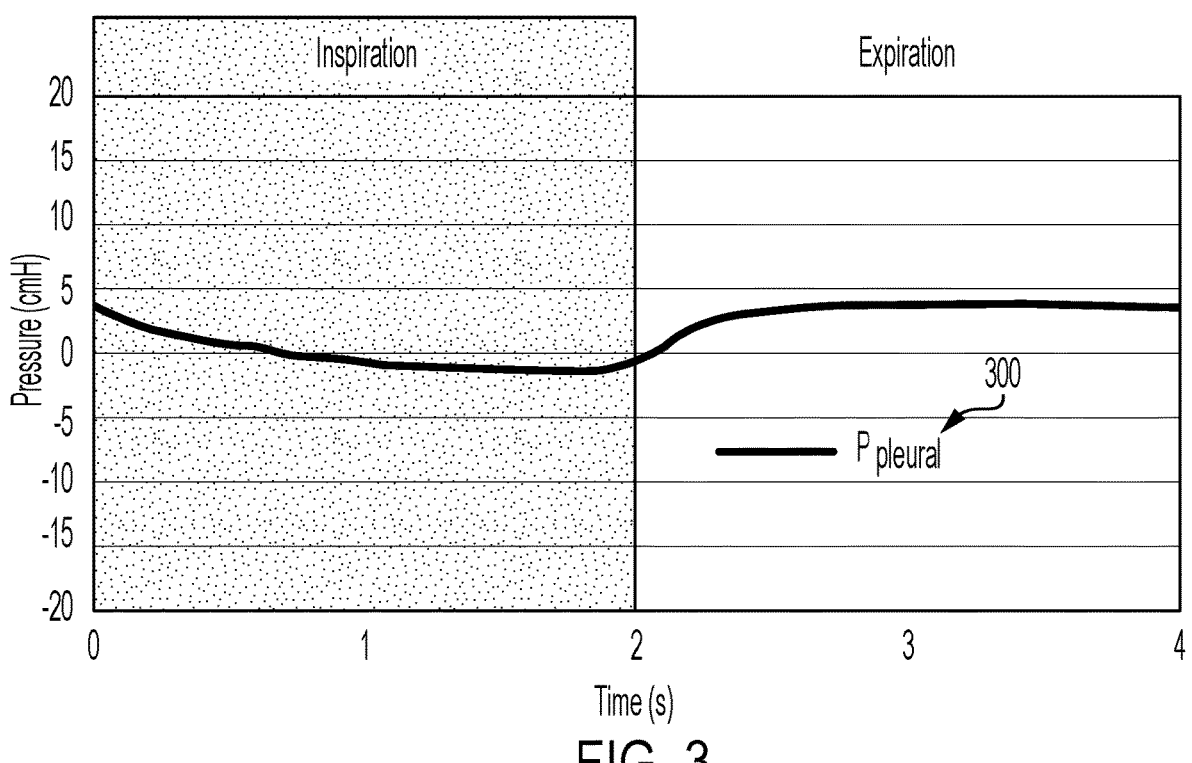
FIG. 3 shows representative pleural pressures as they change during inspiration and expiration.

In operation of fluid-management system 100, fluctuations in pressure between cavity 114 and one-way valve 110 may cause one-way valve 110 to open and close. In one example, the fluctuations in pressure between cavity 114 and one-way valve 110 occur based on respiratory action of a breathing cycle of the person. For instance, when cavity 114 is the pleural cavity, pressure between cavity 114 and one-way valve 110 swings from positive to negative during the breathing cycle. FIG. 3 illustrates an example pressure fluctuation that may occur between cavity 114 and one-way valve 110 during a breathing cycle. Pressures in the pleural cavity are not static and typically vary during normal breathing. As seen in FIG. 3, pleural pressure ($P_{pleural}$) 300 relative to atmospheric pressure swings from slightly negative during inspiration to slightly positive during expiration. During inspiration, external intercostal muscles contract leading to elevation of the ribs and sternum, and the diaphragm contracts, flattening out and pressing down on the abdominal contents. This combined action leads to an expansion of the thoracic cavity with a decrease in the pleural pressure that expands the elastic lung. Expiration during normal breathing is largely a passive process relying on elastic recoil. During expiration, the external intercostal muscles and the diaphragm simply relax. With relaxation of the external intercostals, the elasticity of the inflated lungs causes them to recoil back to their original position. This action leads to a decrease in size of the thoracic cavity with an increase in the pleural pressure.

The fluctuations in pleural pressure can be accentuated in some situations, such as situations where a person is breathing deeply and/or coughing. Based on these fluctuations in pressure between cavity 114 and one-way valve 110, one-way valve 110 will close during inspiration (when pressure is negative) and one-way valve 110 will open during expiration (when pressure is positive). As such, the valve assembly 104 provides a pump action with energy provided by the respiratory action of the person draining fluid from cavity 114 such that one-way valve 110 can allow flow of fluid from cavity 114 to outside during expiration and prevent backflow during inspiration. In particular, given this opening and closing due to respiratory action, valve assembly 104 can act as a pump to move fluid from cavity 114, through tube 116, through one-way valve 110, and out outlet 108. Further, since the pleural cavity is transiently moving positive to negative in pressure, one-way valve 110 also prevents backflow as valve assembly 104 provides the pumping action. When a person breathes in, one-way valve 110 closes and thus acts as check valve to prevent fluid and/or air from entering tube 116. On the other hand, when a person breathes out, the pleural pressure increases and forces fluid to move forward.

An example draining process for draining body cavity 114 is described below. Prior to draining body cavity 114 using fluid-management system 100, a person may first select an external reservoir in which to drain the fluid from cavity 114. In general, the person may drain the fluid into any appropriate reservoir such as a sink, a commode, and/or a container provided by the person, among other possibilities. Further, prior to initiating drainage, the valve assembly area may be cleaned with soap and water and/or decontaminated with alcohol, betadine, or chlorhexidine, among other possibilities. Next, to initiate the draining process, the person may switch adjustable outlet lock 112 to the unlocked position. When adjustable outlet lock 112 is in the unlocked position, fluid may begin moving through fluid-management system 100. As described above, one-way valve 110 may open and close based on fluctuations in the pressure between cavity 114 and one-way valve 110. In practice, when adjustable outlet lock 112 is in the locked position, the one-way valve 110 is typically closed since typically $P_1 \leq P_2 + P_C$.

Upon initially unlocking the adjustable outlet lock 112, fluid may begin moving through fluid-management system 100 due to the pressure of body cavity 114 and/or the pumping action provided by the opening and closing of one-way valve 110. This will move fluid from cavity 114, through tube 116, through one-way valve 110, and then out of outlet 108 and into the external reservoir selected by the person. After the draining process has begun, the person may drain the fluid from cavity 114 until cavity 114 is empty and/or a desired amount of fluid has been drained from cavity 114. Finally, after draining is complete, the person may clean or decontaminate outlet 108 and/or adjustable outlet lock 112 and switch adjustable outlet lock 112 into the locked position.

Fluid-management system 100 may also be designed such that, when a sufficient amount of fluid has moved through fluid-management system 100, a siphon effect can be utilized to help to more quickly drain the fluid from cavity 114.

For instance, fluid-management system 100 may be designed such that the pressure of cavity 114 and/or pumping action provided by valve assembly 104 may allow a column of fluid to form within the tube that in turn leads to a siphon effect. In other words, fluid-management system 100 may be designed such that, once tube 116 is primed by valve assembly 104 (e.g., based on the respiratory action), fluid from cavity 114 can be siphoned out.

Fluid-management system 100 may allow fluid from cavity 114 to be siphoned out when conditions suitable for siphoning occur. In general, siphoning may occur when (i) tube 116 has a sufficient column of fluid in tube 116 and (ii) the end of the column of fluid is lower than the fluid level in cavity 114, which provides a sufficient hydrostatic pressure gradient.

During draining, a person may control the level of outlet 108 in order to facilitate the end of the column of fluid being lower than the fluid level in cavity 114. Ensuring that the tube is held a sufficient amount below the fluid level may facilitate siphoning during the draining process.

The column of fluid needed to generate a siphon effect may vary. Within examples, a sufficient column of fluid may be a column of fluid having a length within the range of 10-100 centimeters (cm). Further, a longer tube may provide a longer column of fluid, which in turn may provide a stronger siphon effect and thus provide a quicker flow of fluid to more quickly drain fluid from cavity 114. In an example, after siphoning begins during a draining process, the person may continue draining fluid from cavity 114 until the cavity 114 is empty and/or a desired amount of fluid is removed from cavity 114. When siphoning is taking place, one-way valve 110 remains open. Finally, after draining is complete, the person may clean and/or decontaminate outlet 108 and/or adjustable outlet lock 112 of valve assembly 104 and move adjustable outlet lock 112 into the locked position. In some examples, the one-way valves, tubing diameter, and/or tubing length can be selected so as to ensure a desired minimum flow rate, such as 25 milliliters per minute (ml/min), 50 ml/min, 75 ml/min, 100 ml/min, 150 ml/min or greater, among other possibilities. Additionally or alternatively, the one-way valves (and associated cracking pressures), tubing length, and/or tubing diameter can be selected to prevent the pressure in the fluid cavity dropping below a desired level, such as $-10$ cmH$_2$O, $-20$ cmH$_2$O, $-30$ cmH$_2$O, or $-40$ cmH$_2$O or more negative, among other possibilities. In an example, for the pleural space, persons can have pain when the pressure is too low, have coughing fits, and there are reports of "reexpansion pulmonary edema" occurring when large volumes are drained and/or the pressure is too low. Preventing the pressure in the fluid cavity from dropping below a desired level may help to avoid or reduce such issues.

In some examples, the cavity pressure of the cavity being drained may tend to remain positive rather than fluctuate from positive to negative based on respiratory action of a person's breathing cycle. For instance, peritoneal cavity pressure relative to atmospheric pressure tends to remain positive throughout the breathing cycle. As such, in an example where the body cavity being drained is the peritoneal cavity, the pressure between cavity 114 and one-way valve 110 may tend to remain positive. In such a case, one-way valve 110 may not routinely open and close to provide a pump action to move fluid through the tube 116. Rather, in such a case, when adjustable outlet lock 112 is switched to the unlocked position, the positive peritoneal-cavity pressure may tend to cause fluid to move forward throughout the tube and to keep one-way valve 110 open.

However, in situations where the cavity pressure may tend to remain positive, fluctuations in pressure may still occur for various reasons that may cause one-way valve 110 to close. For instance, the cavity pressure may, for one reason or another, fluctuate to negative. As one possibility, if the body position and/or tip of tube 116 were positioned to be such that the abdomen was lower than the tube outlet, the pressure could drop to negative. As another possibility, if the space (e.g., peritoneal space) was diseased such that the bowel/abdominal wall could not expand/shift as fluid is drained, a negative pressure could generate. As yet another possibility, a large release of gas (volume shift) from the abdomen could transiently transition pressure to negative. Other examples are possible as well. In such a case where the cavity pressure may tend to remain positive but fluctuations in pressure may still occur for various reasons that may cause one-way valve 110 to close, rather than providing a pumping action during the draining process, one-way valve 110 may instead serve primarily as a backstop to ensure that, if pressure fluctuates during the draining process to a negative pressure for some reason, one-way valve 110 closes to prevent backflow.

In the examples discussed above, the valve assembly 104 includes a single one-way valve. In other examples, the valve assembly 104 includes two one-way valves arranged in series, and the two one-way valves may allow for additional capabilities and/or benefits relative to a valve assembly having a single one-way valve. An example fluid-management system including a valve assembly having two one-way valves is described further with reference to FIGS. 4A-B.

Figure 4B:
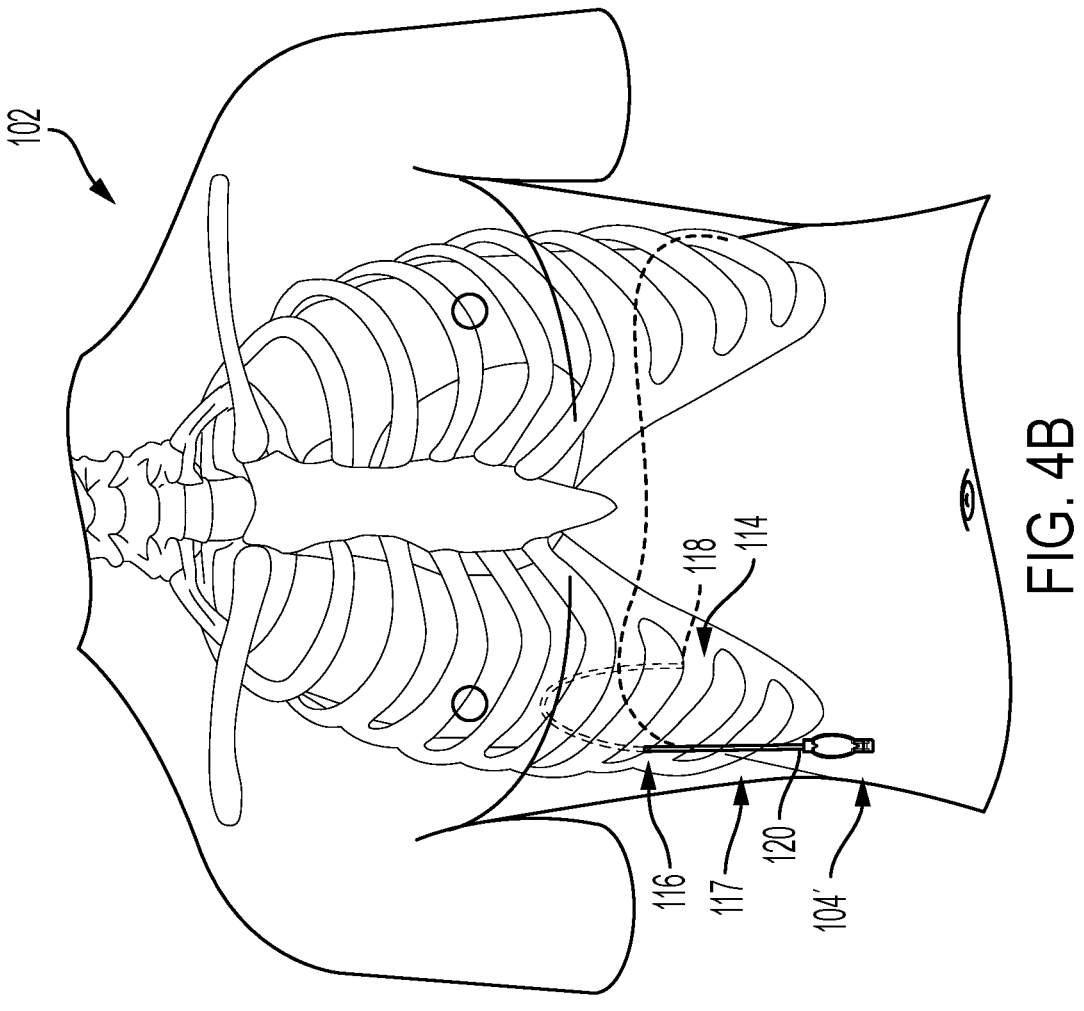
FIG. 4B illustrates the example fluid-management system of FIG. 4A implanted in a person.
Figure 4A:
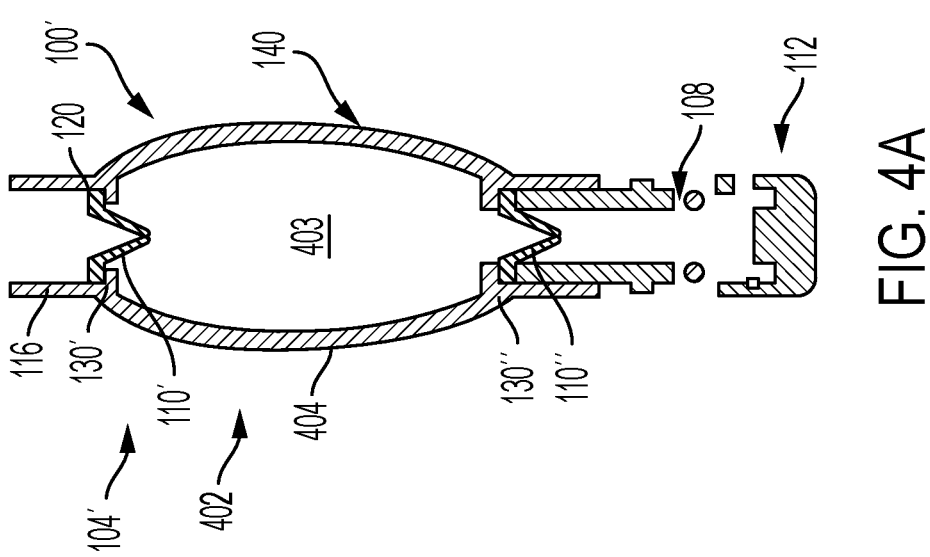
FIG. 4A illustrates an example fluid-management system, according to an example embodiment.

FIG. 4A depicts an example fluid-management system 100' and FIG. 4B depicts the fluid-management system 100' implanted in a person's body 102. Fluid-management system 100' includes a valve assembly 104' having an inlet 106, and outlet 108, one-way valves 110' and 110", and an adjustable outlet lock 112. One-way valves 110' and 110" are arranged in series and are housed in a pumping chamber 402 or on the proximal and distal ends of pumping chamber 402. One-way valves 110' and 110" are positioned between inlet 106 and outlet 108 and are each configured to open and close based on fluctuations in pressure between cavity 114 and the one-way valve. Further, one-way valve 110' is configured to open and close based on changes in cavity 114 pressure and pressure on an inside 403 of chamber 402, and one-way valve 110" is configured to open and close based on changes in pressure on inside 403 of chamber 402 (which may change based on cavity pressure and opening of one-way valve 110') and atmospheric pressure. Fluid-management system 100' also includes a fluid-management tube 116 for carrying fluid from cavity 114 to valve assembly 104'. Tube 116 is configured to extend from inlet 106 to cavity 114 and allow movement of fluid from cavity 114 to inlet 106 of valve assembly 104'. Tube 116 is implanted in person's body 102, such that a proximal end 118 of tube 116 is positioned within cavity 114 and a distal end 120 is positioned external to body 102. Further, valve assembly 104' is positioned external to the person's body 102.

As mentioned above, the one-way valves 110' and 110" are arranged in series and are housed in pumping chamber 402 or on the proximal and distal ends of pumping chamber 402. In an example, the main body 404 of pumping chamber may form and/or house one-way valve frames 130' and 130", which enclose and provide structure and support to one-way valves 110' and 110", respectively. In the example of FIG. 4A, the one-way valve frame 130' is integral with tube 116. In other examples, one-way valve frame 130' may serve to connect to distal end 120 of tube 116 (e.g., in a similar fashion as illustrated in FIG. 1A). The size and shape of the one-way valve frame 130' can be designed to provide joining points or interconnectable joints to tube 116. In an example, valve assembly 104' is non-removably attached to tube 116.

The valve assembly 104' may operate is a similar fashion as the valve assembly 104 described with respect to FIGS. 1-3. Furthermore, valve assembly 104' provides some additional capabilities for draining fluid from cavity 114. For instance, valve assembly 104' may provide additional capabilities and/or benefits relative to a valve assembly having a single one-way valve, including but not limited to improving the flow of fluid movement in the fluid-management system and/or providing an additional barrier to retrograde flow, among other possibilities.

Turning first to operating in a similar fashion as valve assembly 104, each of valves 110' and 110" may operate in the same fashion and have the same properties as one-way valve 110 of FIG. 1A. For instance, one-way valves 110' and 110" are each configured to open and close based on fluctuations in pressure between a cavity of a person's body and the one-way valve. As one example, fluctuations in pressure (e.g., fluctuations that occur based on respiratory action of a breathing cycle of the person) between cavity 114 and one-way valves 110' and 110" may cause one-way valves 110' and 110" to open and close, thereby providing a pumping action to move fluid. Given that one-way valves 110' and 110" are the same or similar in many respects to one-way-valve 110, one-way valves 110' and 110" thus are not described in as great of detail. It should be understood, however, that any of the possibilities and permutations described with respect to one-way valve 110 are also possible with respect to one-way valves 110' and 110".

Turning next to the additional capability of creating fluid movement in the fluid-management system 100', the pumping chamber 402 of valve assembly 104' can be used to prime the system and get fluid moving through fluid-management system 100'. Such a two-valve configuration may allow a person to prime the fluid-management system, which may help to speed up the draining process by getting fluid to move more quickly through the fluid-management system, which in turn may get the siphon effect to occur more quickly.

Such priming of fluid-management system 100' may be useful in various situations. For example, such priming of the system may be useful if the pumping action provided by the respiratory action is not sufficient to get fluid moving and/or does not get fluid moving as quickly as a person desires. As another example, such priming of the system may be useful if there is low positive pressure between cavity 114 and one-way valves 110', 110" that is insufficient to get fluid moving and/or does not get fluid moving as quickly as a person desires. As yet another example, such priming of the system may be useful if for some reason air is in the tube. In tubes common in catheter applications, a small amount of air can generate enough surface tension to air lock the tube. Priming of fluid-management system 100' may help overcome such generated airlocks. As still yet another example, such priming of fluid-management system 100' may be useful if there is not a sufficient hydrostatic pressure gradient to provide for a siphon effect. Other examples are possible as well.

Such a two-valve configuration may also allow for the generation of supraphysiologic pressures (both positive by compressing and negative by design of the resilience of the pump chamber 402) that may also be of benefit to clear potential obstructions and/or debris from the fluid-management system 100' (e.g., within the tubing, from within the one-way valves, or from within other regions of the valve assembly 104').

Figure 5A:
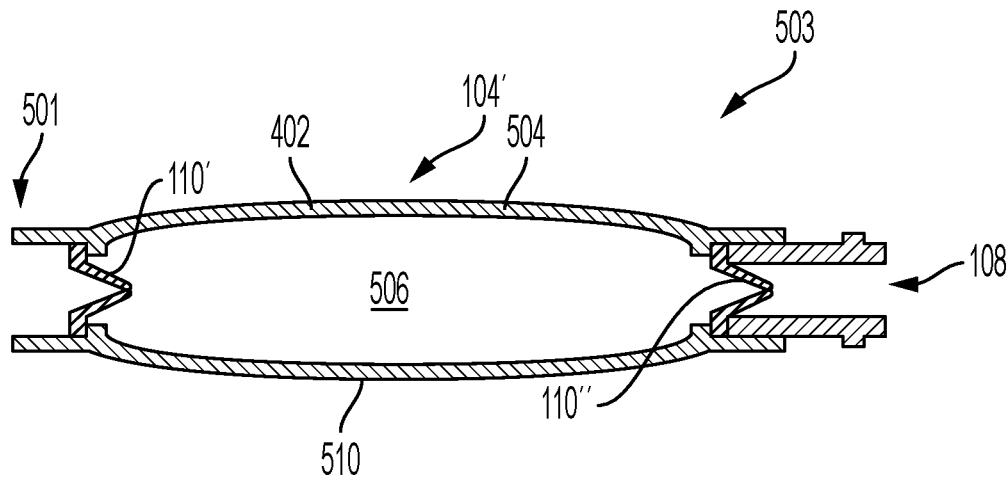
FIGS. 5A-D illustrates a pumping chamber of the fluid-management system of FIG. 4A at various stages of compression and decompression.

Priming of fluid-management system 100' using pumping chamber 402 is described further with respect to FIGS. 5A-D. FIG. 5A shows a cross-sectional schematic view of valve assembly 104' in a generally or substantially non-compressed state with both one-way valve 110' and one-way valve 110" closed. For clarity, one-way valve 110' is also referred to herein as an "inlet one-way valve," and one-way valve 110" is referred to as an "outlet one-way valve." Inlet one-way valve 110' is positioned on a first side 501 of pumping chamber 402 proximate to the inlet of valve assembly 104' and outlet one-way valve 110" is positioned on a second side 503 of pumping chamber 402 proximate to outlet 108 of valve assembly 104.

Figure 5B:
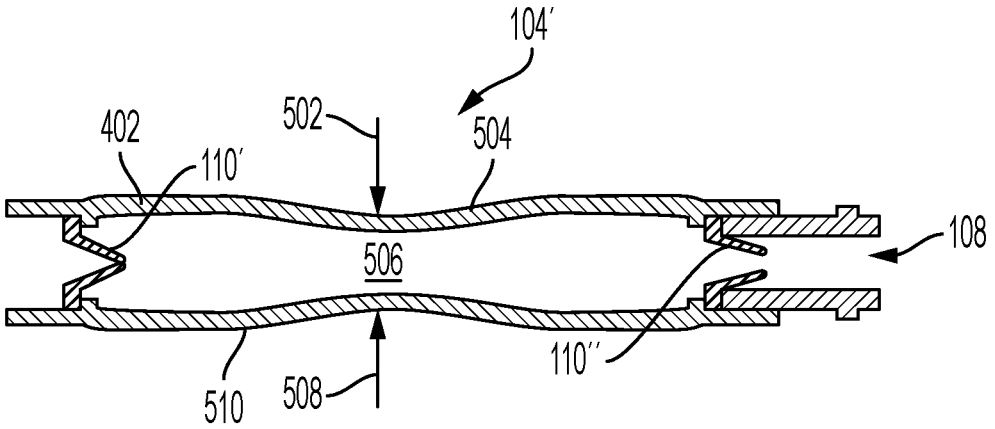

FIG. 5B shows a cross-sectional schematic view of valve assembly 104' in a generally or substantially compressed state. In an example, as shown, a first force 502 may act on a first wall 504 causing first wall 504 to collapse in towards interior space 506. Correspondingly, a second force 508 may additionally or alternatively act on a second wall 510 causing second wall 510 to collapse in towards interior space 506.

First force 502 and second force 508 may be applied to pumping chamber 402 in any suitable fashion. As one possibility, a person using fluid-management system 100' may supply the forces by manually compressing pumping chamber with their fingers. As another possibility, valve-system 104' may include an electromechanical actuator configured to apply forces 502 and 508. For instance, valve assembly 104' may include a piezoelectric diaphragm connected to the body of pumping chamber 402. The piezo-electric diaphragm may be activated and inactivated by a controller, and both the piezoelectric diaphragm 540 and the controller 530 may be powered, e.g., by a battery. As another example, valve assembly 104' may include a piston or cam configured to apply forces 502 and 508 to pumping chamber 402. Other example methods and systems for applying forces 502 and 508 are possible as well.

The collapse of the first wall 504 and/or second wall 510 serves to decrease the volume of interior space 506 and to increase the pressure in interior space 506. This increase in pressure causes inlet one-way valve 110' to remain closed and causes outlet one-way valve 110" to open, and fluid located in interior space 506 to flow from interior space 506 through outlet one-way valve 110" and out outlet 108. For incompressible fluids, the change of volume experienced by interior space 506 in response to the collapse of first wall 504 and/or second wall 510 will be approximately equal to the volume of fluid that moves from interior space 506 through outlet one-way valve 110". As the fluid moves from interior space 506 through outlet one-way valve 110", the pressure in interior space 506 will decrease. Once the interior pressure equals or substantially equals the pressure in outlet 108, flow will stop and outlet one-way valve 110" will close as shown in FIG. 5C.

Figure 5C:
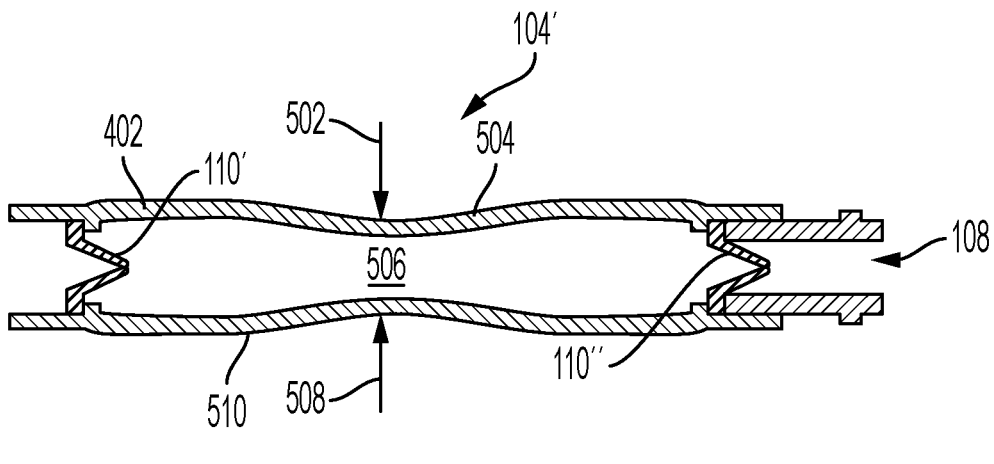
Figure 5D:
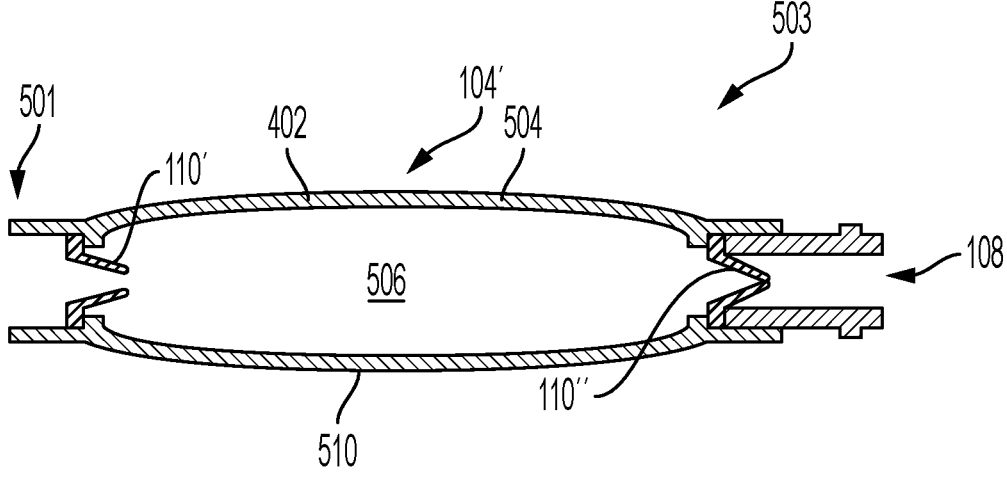

As described above, the body of pumping-chamber 402 may be substantially resiliently flexible and therefore, after being placed in a compressed state as shown in FIGS. 5B and 5C, valve assembly 104' will return to an uncompressed state as shown in FIG. 5D when at least one of the first force 502 and the second force 508 are removed. As the first wall 504 returns to its uncompressed state as the first force 502 is removed and/or the second wall 510 returns to its uncom-pressed state as the second force 508 is removed, the volume of the interior space 506 increases and the pressure in the interior space 506 decreases. The pressure inside the interior space 506 eventually drops below the pressure on the inlet 501 near inlet one-way valve 110' and causes inlet one-way valve 110' to open and fluid located in the inlet to flow into the interior space 506. In this way, valve assembly 104' operates as a pump that, generally, draws fluid from inlet 501 and passes it to outlet 108.

In some examples, pumping chamber 402 may be made of material that allows for pumping chamber 402 to be com-pressed and then freely returned to its original state. Pump-ing chamber 402 may be made of any suitable material. For example, pumping chamber 402 may be a resiliently flexible tube or cylinder made of polyurethane, silicone, polyvinyl chloride, or latex rubber. Alternatively, pumping chamber 402 may be made of a combination of two or more materials where at least one of the component materials provides resilience and at least one of the component materials provides fluid containment. For example, pumping chamber 402 may be composed of an elastic nitinol, steel, polyester, or other elastic component to provide for resiliency and a second fluid containment component such as polyurethane, silicone, polyvinyl chloride, latex rubber, polyethylene tere-phthalate, nylon, polytetrafluoroethylene, PEBAX, or the like to provide fluid containment within pumping chamber 402. In other examples, such as examples where valve assembly 104' includes an electromechanical actuator (e.g., a piezoelectric diaphragm, piston, or cam configured to apply forces 502 and 508 to pumping chamber 402), the material may be flexible but not resilient (or having limited resilience), as an electromechanical actuator may provide both active compression and active rarefication.

Turning next to the additional barrier to retrograde flow, the addition of the second one-way valve provides another barrier to retrograde flow. In the example a FIG. 1A, one-way valve 110 provides a barrier to retrograde flow, whereas in the example of FIG. 4a, each of one-way valves 110' and 110" provide a barrier to retrograde flow. This additional barrier to retrograde flow may provide increased protection against retrograde flow.

In order to prevent blocking or clogging of the disclosed fluid-management system, one or more components of the fluid-management system may be coated in anticoagulation factors or fibrinolytic factors. For example, the components or surfaces of valve assemblies 104, 104' and/or implanted tube 116 may be coated at least in part with anticoagulation factors or fibrinolytic factors. For instance, with reference to FIG. 1A, internal portions of a body 140 of valve assembly 104, one-way valve 110, and/or internal portions of tube 116 may be coated in anticoagulation factors or fibrinolytic factors. Further, with reference to FIG. 4A, internal portions of pumping chamber 402, one-way valves 110' and 110", and/or internal portions of tube 116 may be coated in anticoagulation factors or fibrinolytic factors. Other compo-nents may be coated with anticoagulation factors or fibrin-olytic factors as well.

The presence of the anticoagulation factors may reduce the amount of clotting that would otherwise occur if they were not present. Examples of anticoagulation factors include heparin, low molecular weight heparin, fonda-parinux, idraparinux, idrabiotaparinux, diabigatran, rivar-oxaban, apixan, betrixaban, edoxaban, darexaban, letaxa-ban, eribaxaban, hirudin, lepirudin, bivalirudin, argatroban, dabigatran, ximelagatran, hementin, vitamin E, coumarin, warfarin, acenocoumarol, phenprocoumon, atromentin, phenindione, brodifacoum, and difenacoum. Examples of fibrinolytic factors include plasmin, tissue plasminogen acti-vator, urokinase, streptokinase, plasminogen activator inhibitor-1 inhibitor, and plasminogen activator inhibitor-2 inhibitor. Other examples of anticoagulation factors or fibrinolytics may be used.

In at least some implementations of the valve assembly 104' with pumping chamber 402, one-way valves 110' and 110" may each be configured to have a low "cracking pressure," such that the one-way valve is configured to transition from a closed state to an open state with relatively small differential pressures across the one-way valve. For instance, the cracking pressure of each one-way valve can range anywhere from about 25 cmH$_2$O or less to about 5 cmH$_2$O or less, and as specific examples, the cracking pressure of a given one-way valve could be less than about 25 cmH$_2$O, less than about 15 cmH$_2$O, less than about 10 cmH$_2$O, or less than about 5 cmH$_2$O. Further, in at least some implementations, the one-way valves 110' and 110" may also each be configured to have a low "resealing pressure," such that the one-way valve is configured to transition from an open state to a closed state with small differential pressures across the one-way valve. For instance, the resealing pressure of each one-way valve can range anywhere from about 15 cmH$_2$O or less to about 2 cmH$_2$O or less, and as specific examples, the cracking pressure of a given one-way valve could be less than about 15 cmH$_2$O, less than about 10 cmH$_2$O, less than about 5 cmH$_2$O, or less than about 2 cmH$_2$O. In other implementations of valve assembly 104' with pumping chamber 402, the cracking and/or resealing pressures of one-way valves 110' and 110" may be higher.

Pumping chamber 402 is described with reference to examples where the one or more one-way valves take the form of two one-way valves arranged in series. In some examples where valve assembly 104 includes a single one-way valve, the valve assembly 104 may further include a compressible chamber positioned on the inlet or outlet side of the single one-way valve, such as positioned between the single one-way valve and a small narrowing in the lumen of the flow pathway which may provide hydrostatic resistance. Such a compressible chamber can be used to help initiate fluid flow and/or to enhance or allow a pumping action.

Figures 6A, 6B, 7A, 7B:
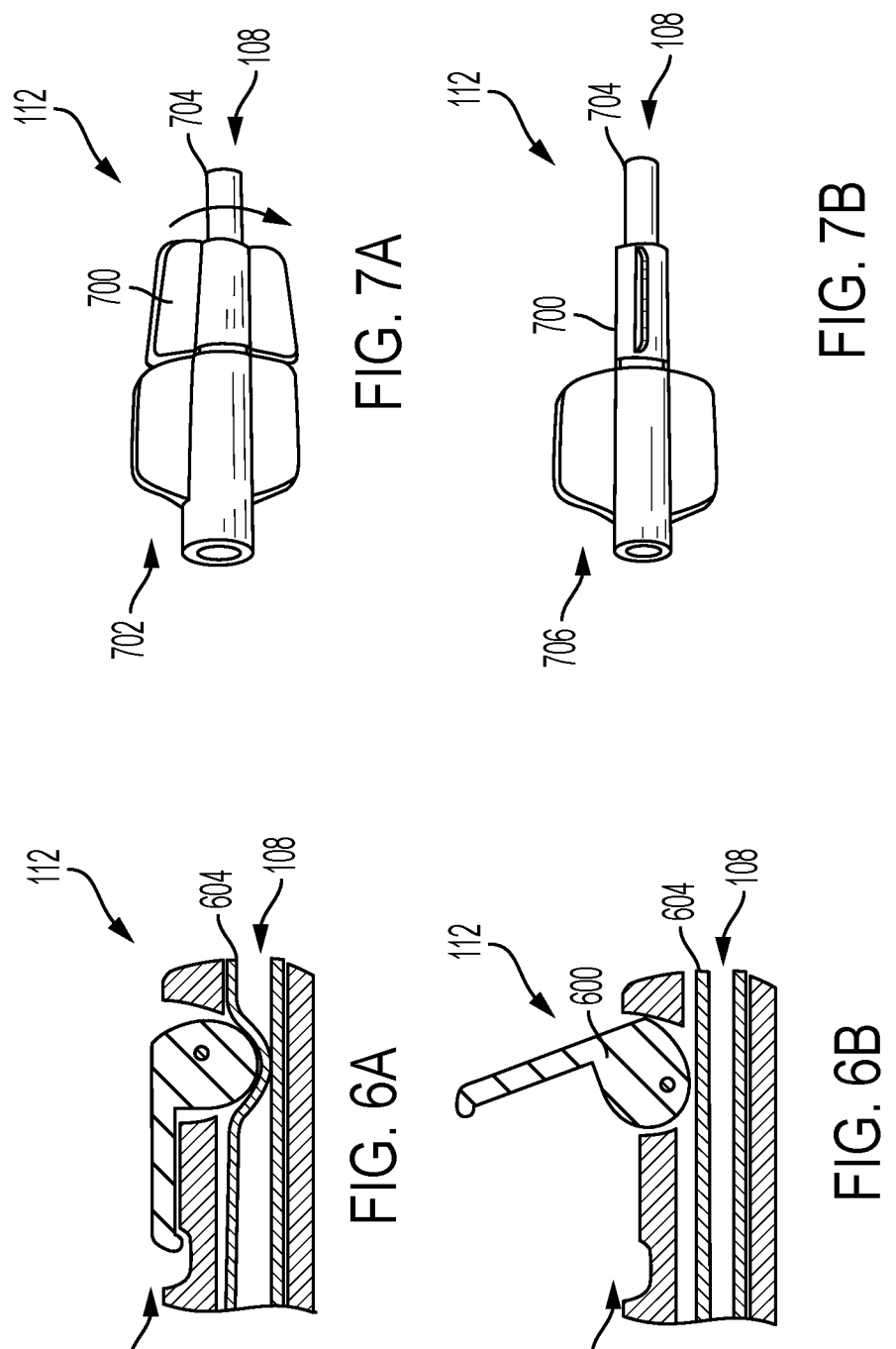
FIGS. 6A-B illustrate an example adjustable outlet lock, according to an example of the present disclosure.
FIGS. 7A-B illustrate an example adjustable outlet lock, according to an example of the present disclosure.

As mentioned above, in the example of FIG. 1A, adjustable outlet lock 112 takes the form of a cap, but various adjustable outlet locks 112 are possible. As one possibility, adjustable outlet lock 112 may take the form of a pinch lever. For instance, with reference to FIGS. 6A-B, adjustable outlet lock 112 may include a lever 600 positioned at outlet 108 that may be adjusted to move the lever 600 between (i) a locked position 602 (see FIG. 6A) in which lever 600 pinches a tube 604 of outlet 108 in order to seal outlet 108 and (ii) an unlocked position 606 (see FIG. 6B) in which lever 600 no longer pinches tube 604, thus allowing tube 604 to open and thereby allowing fluid movement through outlet 108.

As another possibility, adjustable outlet lock 112 may take the form of a twist pinch. For instance, with reference to FIGS. 7A-B, adjustable outlet lock 112 may include a twist pinch 700 positioned at outlet 108 that may be adjusted to move twist pinch 700 between (i) a locked position 702 (see FIG. 7A) in which twist pinch 700 pinches a tube 704 of outlet 108 in order to seal outlet 108 and (ii) an unlocked position 706 in which twist pinch 700 no longer pinches tube 704, thus allowing tube 704 to open and thereby allowing fluid movement through outlet 108.

As yet another possibility, adjustable outlet lock 112 may take the form of a twist cap that activates pinch arms. For instance, with reference to FIGS. 8A-D, adjustable outlet lock 112 may include a twist cap 800 positioned at outlet 108 that may be adjusted to move twist cap 800 between (i) a locked position 802 (see FIG. 8C and FIG. 8D, which is a cross-sectional view of adjustable outlet lock 112 taken along line 8D-8D in FIG. 8C) in which twist cap 800 forces pinch arms 808 to pinch a tube 804 of outlet 108 in order to seal outlet 108 and (ii) an unlocked position 806 (see FIG. 8A and FIG. 8B, which is a cross-sectional view of adjustable outlet lock 112 taken along line 8B-8B in FIG. 8A) in which twist cap 800 allows pinch arms 808 to flex outward, thus allowing tube 804 to open and thereby allowing fluid movement through outlet 108. Another example twist cap that activates pinch arms is illustrated in FIGS. 9A-C. As shown, adjustable outlet lock 112 may include a threaded twist cap 900 positioned at outlet 108 that may be adjusted to move threaded twist cap 900 between (i) a locked position 902 (see FIG. 9C) in which threaded twist cap 900 forces pinch arms 908 to pinch a tube 904 of outlet 108 in order to seal outlet 108 and (ii) an unlocked position 906 (see FIG. 9B) in which threaded twist cap 900 allows pinch arms 908 to flex outward, thus allowing tube 904 to open and thereby allowing fluid movement through outlet 108. As shown in FIG. 9C, there is a partial conical taper on the inside of twist cap 900 that engages the pinch arms 908 when twist cap 900 is screwed all the way on that closes the pinch arms 908. Further, when twist cap is partially unscrewed (see FIG. 9B), the partial conical taper on the inside of twist cap 900 disengages and releases the pinch arms 108. Additionally, as indicated in FIGS. 9A-B, tube 904 may be opened when the inside of twist cap 900 disengages and releases the pinch arms 108 (see FIG. 9B), and, with continued unscrewing, twist cap 900 can be completely disengaged from pinch arms 908 (see FIG. 9A).

As yet another possibility, adjustable outlet lock 112 may take the form of an offset device. For instance, with reference to FIGS. 10A-B, adjustable outlet lock 112 may include an offset device 1000 positioned at outlet 108 that may be adjusted to move offset device 1000 between (i) a locked position 1002 (see FIG. 10A) in which offset device 1000 blocks outlet 108 in order to seal outlet 108 and (ii) an unlocked position 1006 (see FIG. 10B) in which offset device 1000 no longer blocks outlet 108 thereby allowing fluid movement through outlet 108.

Figures 11A, 11B:
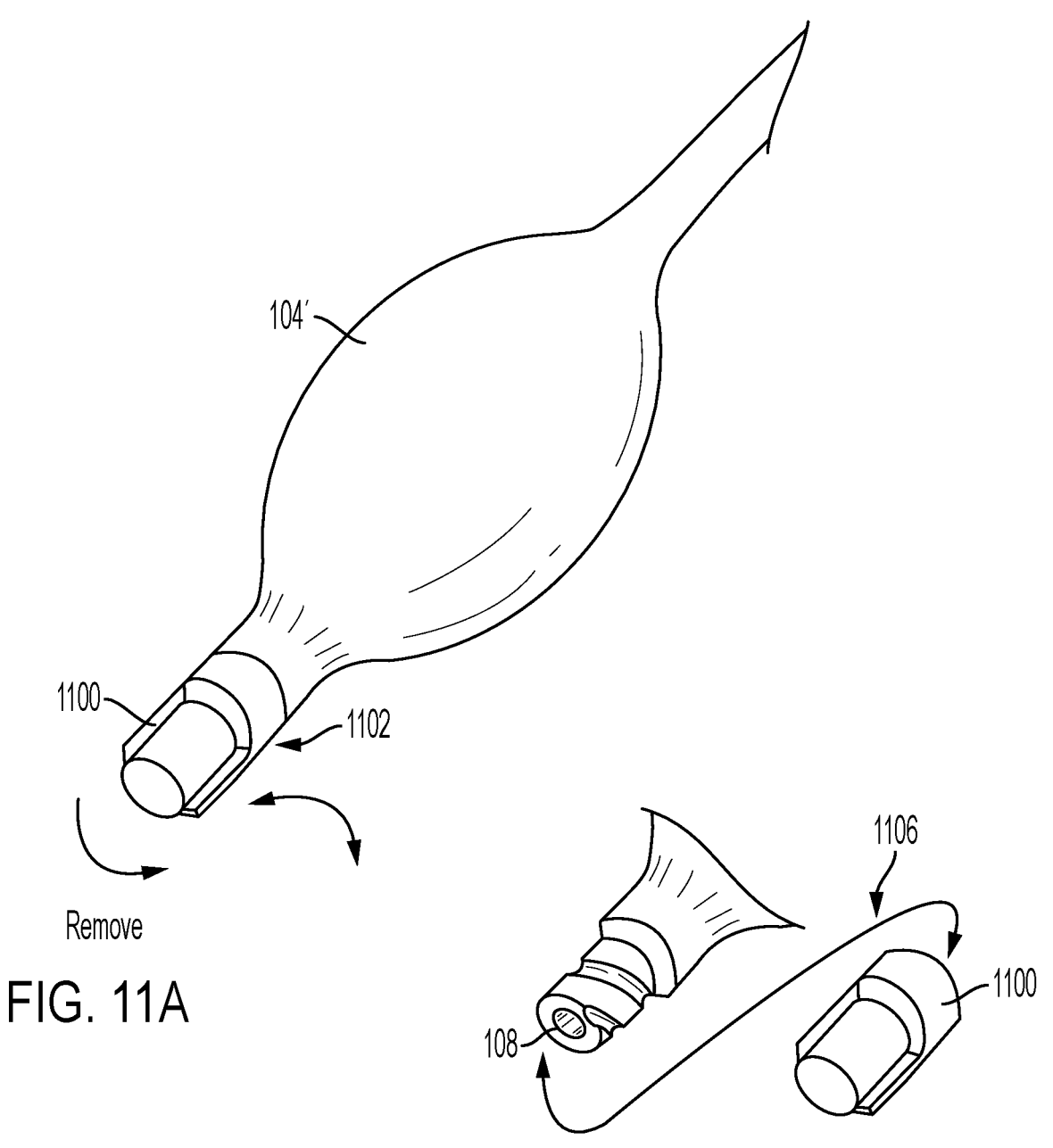
FIGS. 11A-B illustrate an example adjustable outlet lock, according to an example of the present disclosure.

FIGS. 11A-B illustrate yet another example adjustable outlet lock, which in this example is disposed on valve assembly 104'. In this example, adjustable outlet lock 112 takes the form of a removable locking cap 1100 positioned at outlet 108 that may be adjusted to move locking cap 1100 between (i) a locked position 1102 (see FIG. 11A) in which removable locking cap 1100 blocks outlet 108 in order to seal outlet 108 and (ii) an unlocked position 1106 in which removable locking cap 1100 no longer blocks outlet 108 thereby allowing fluid movement through outlet 108.

Figures 12A, 12B:
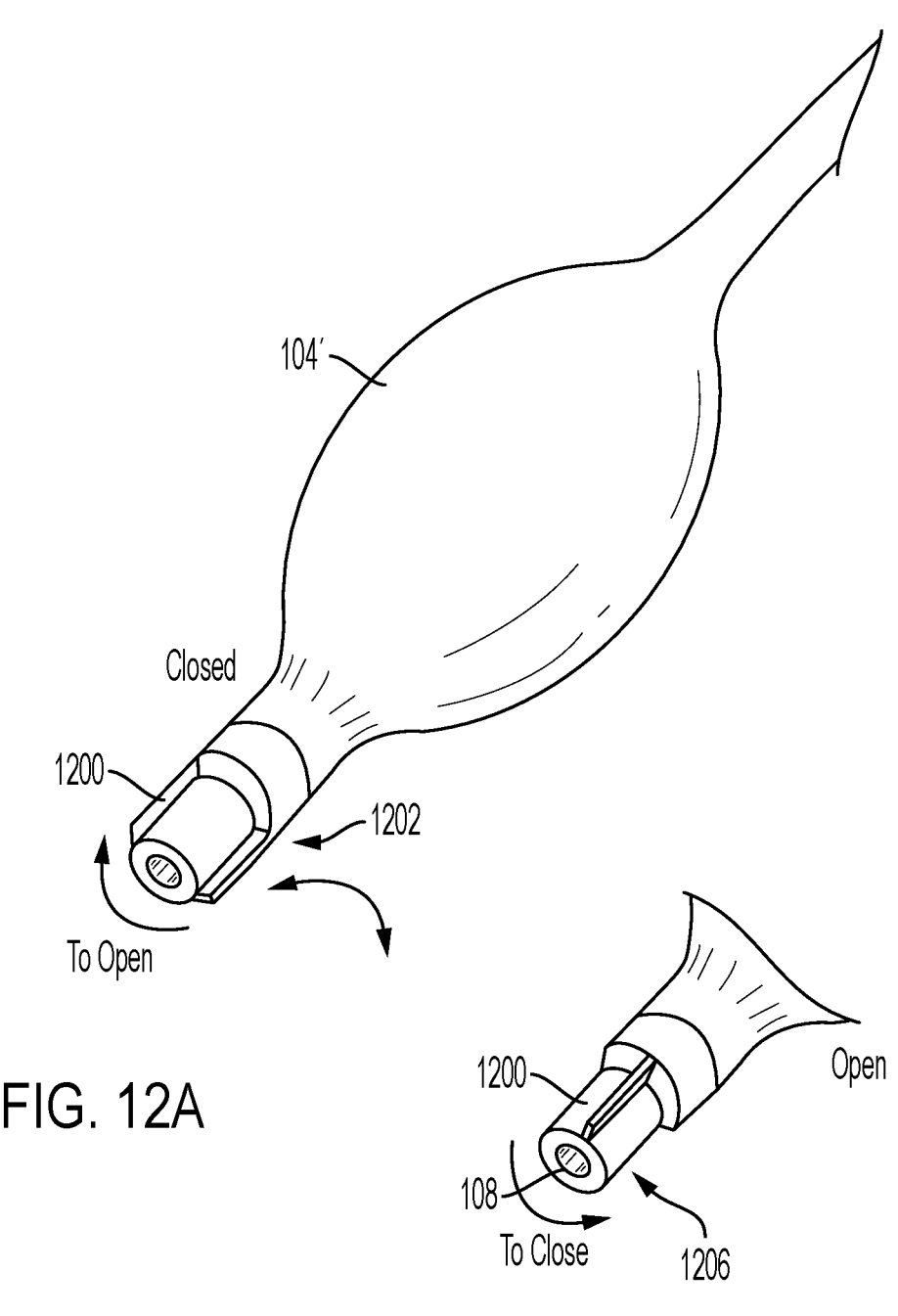
FIGS. 12A-B illustrate an example adjustable outlet lock, according to an example of the present disclosure.

FIGS. 12A-B illustrate yet another example adjustable outlet lock, which in this example is disposed on valve assembly 104'. In this example, adjustable outlet lock 112 takes the form of a rotatable locking valve 1200 positioned at outlet 108 that may be adjusted to move rotatable locking valve 1200 between (i) a locked position 1202 (see FIG. 12A) in which rotatable locking valve 1200 blocks outlet 108 in order to seal outlet 108 and (ii) an unlocked position 1206 in which rotatable locking valve 1200 no longer blocks outlet 108 thereby allowing fluid movement through outlet 108.

Other example adjustable outlet locks are possible as well, including, for instance, ball-valves, and stop-cocks, and external clamps, among other possibilities. Further, in examples where the adjustable outlet lock comprises a removable cap, valve assembly 104 may also include a tether for the removable cap, so the removable cap remains attached to valve assembly 104 when a person is draining fluid from cavity 114 and the removable cap is in the unlocked position.

As mentioned above, a person may drain the fluid from cavity 114 until cavity 114 is empty and/or a desired amount of fluid has been drained from the cavity. The amount of fluid drained using fluid-management system 100 may depend on various factors, such as the cavity being drained, the amount of fluid in the cavity being drained, an amount of time available for draining, a recommend amount of fluid to drain, among other possibilities. In an example, when draining a pleural cavity, a person may drain approximately 100 to 200 milliliters per day. In another example, when drain a peritoneal cavity, a person may drain approximately 0.75 to 1.25 liters a day. Other examples are possible as well.

Figures 13, 14:
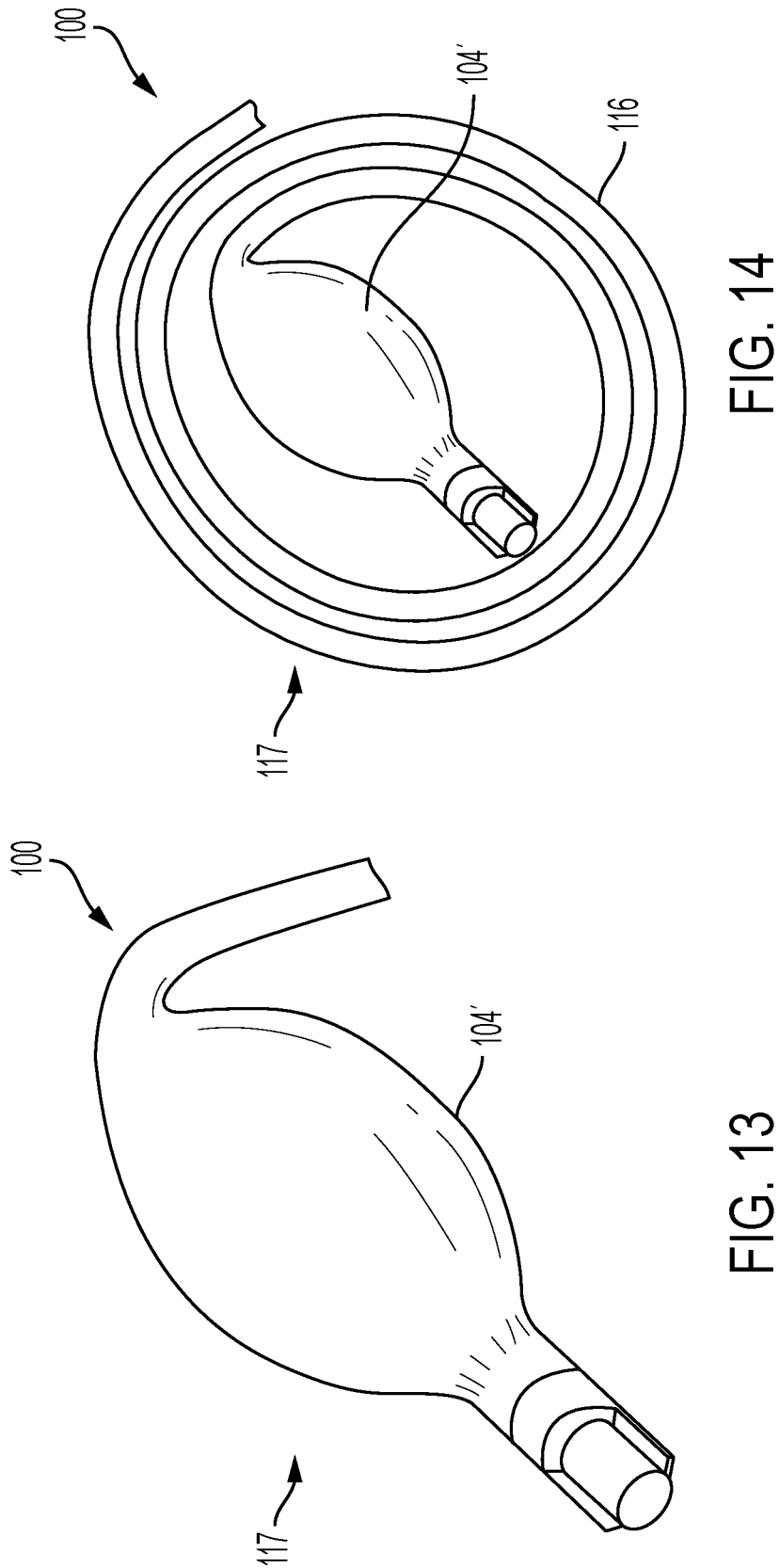
FIG. 13 illustrates an example arrangement of an external portion of a fluid-management system, according to an example of the present disclosure.
FIG. 14 illustrates an example arrangement of an external portion of a fluid-management system, according to an example of the present disclosure.

As mentioned above, the disclosed fluid-management system 100 can remain with the person at all times. When a person is not draining the body cavity, the person may secure the external portions of the fluid-management system to the person's body. For example, the external portion of the fluid-management system may be secured to the person (e.g., via an appropriate securing mechanism such as a gauze pad and/or medical tape, among other possibilities), such as external portion 117 of fluid-management system 100 shown in FIG. 13. In some examples, the person may coil the external portion of the implanted tube, so that the external portion of the fluid-management system may be secured to the person (e.g., via an appropriate securing mechanism such as a gauze pad and/or medical tape, among other possibilities). For instance, FIG. 14 depicts an example of such coiling. In particular, when a person is not draining the body cavity, the person may coil the external portion of implanted tube 116, so that the external portion 117 of fluid-management system 100 may be secured to the person. In cases where the external portion of the implanted tube may be coiled, the geometry of valve assembly 104 and/or pumping chamber 402 can be sized and shaped to facilitate positioning within the coiled implanted tube 116 and/or to minimize the profile of the secured fluid-management system.

Figure 15B:
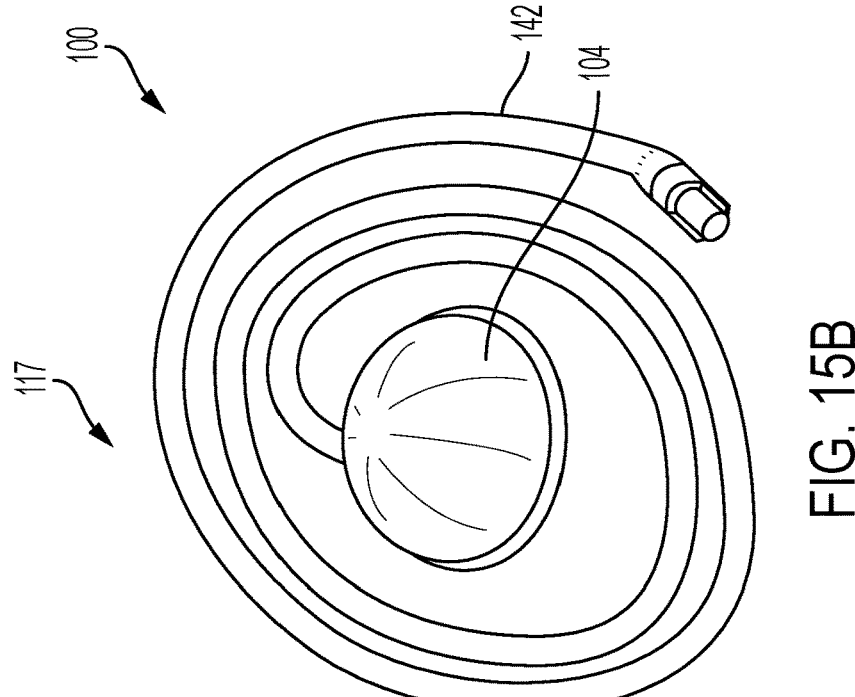
FIG. 15B illustrates an example arrangement of an external portion of the fluid-management system of FIG. 15A, according to an example of the present disclosure.
Figure 15A:
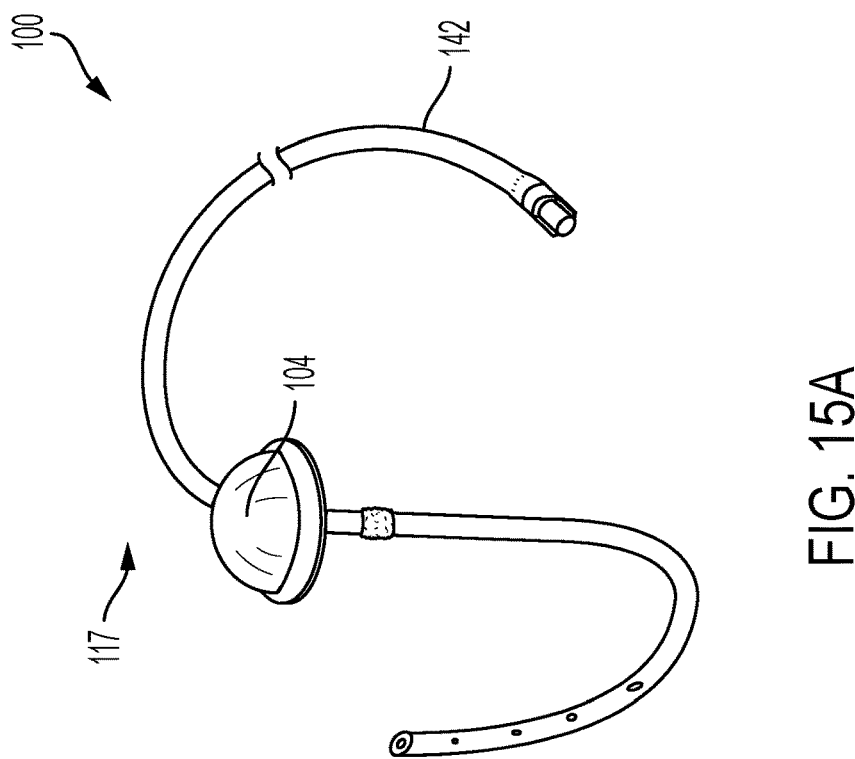
FIG. 15A illustrates an example fluid-management system, according to an example of the present disclosure.

Further, FIGS. 15A-B depict another example of coiling. In particular, FIG. 15A illustrates an example fluid-management system 100, and FIG. 15B illustrates an example arrangement of an external portion 117 of the fluid-management system. With reference to FIG. 15A, fluid management system 100 includes tube 116 for carrying fluid from a body cavity of a person to valve assembly 104 and external tube 142. In this example, tube 116 may be within or substantially within the person's body, while valve assembly 104 (including external tube 142) may be external to the person's body. In this situation, when a person is not draining the body cavity, the person may coil external tube 142, so that the external portion 117 of fluid-management system 100 may be secured to the person. In cases where the external tube may be coiled, the geometry of valve assembly 104 and/or pumping chamber 402 can be sized and shaped to facilitate positioning within coiled external tube 142 and/or to minimize the profile of the secured fluid-management system.

Figure 16:
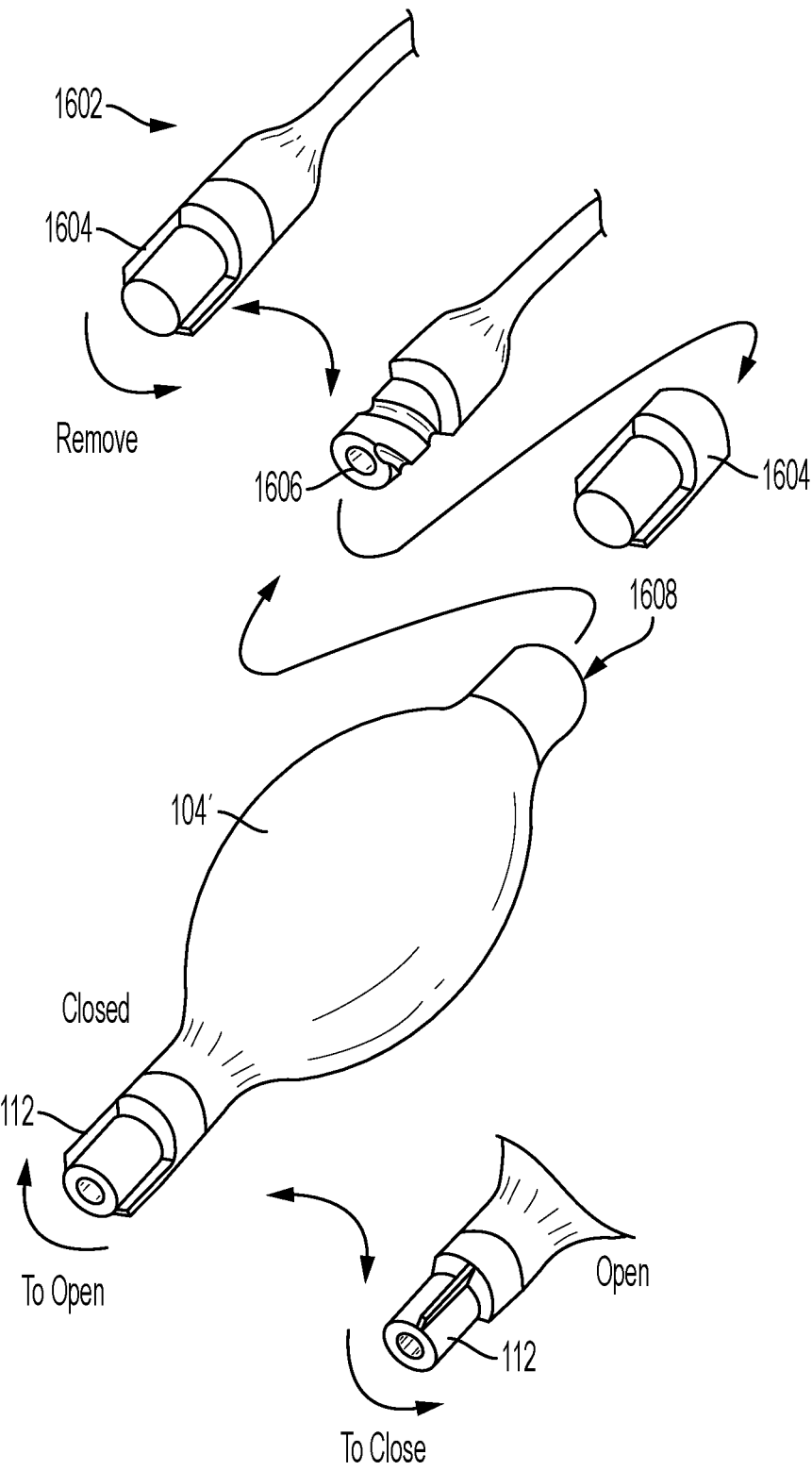
FIG. 16 illustrates an example process for connecting an example fluid-management system to an implanted tube, according to an example of the present disclosure.
Figure 17:
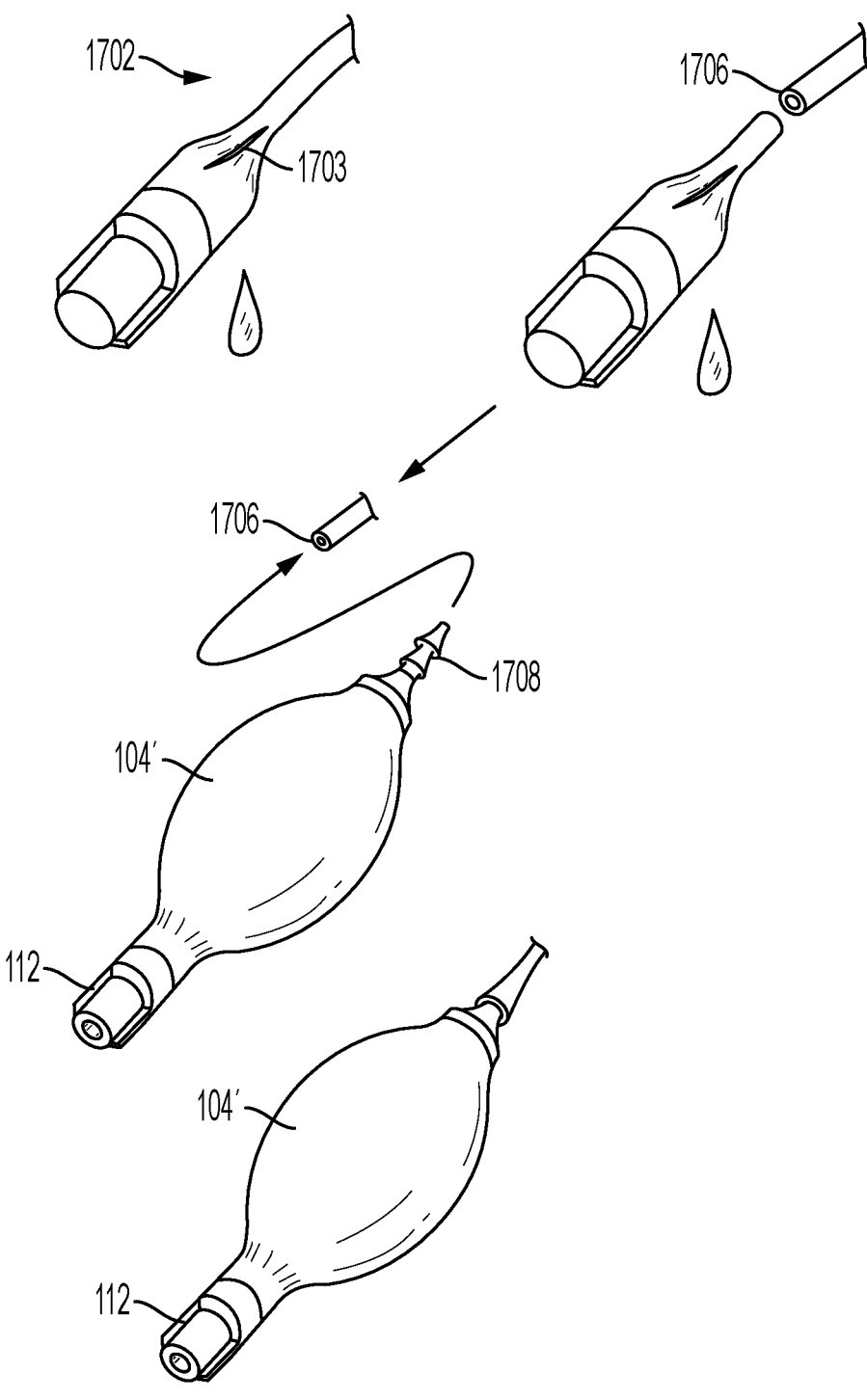
FIG. 17 illustrates an example process for connecting an example fluid-management system to an implanted tube, according to an example of the present disclosure.

In some examples, valve assembly 104 or valve assembly 104' may be connected to an indwelling catheter, such as an indwelling pleural catheter. In order to facilitate attachment to an indwelling catheter, valve assembly 104 or valve assembly 104' may include an attachment mechanism for attachment to the indwelling catheter. FIGS. 16 and 17 illustrate two examples of connecting an example fluid-management system including valve assembly 104' to an indwelling catheter.

Turning first to FIG. 16, FIG. 16 illustrates an example process for connecting valve assembly 104' to an indwelling catheter 1602. Indwelling catheter 1602 includes a locking cap 1604. Locking cap 1604 may be removed, thereby revealing distal end 1606 of indwelling catheter 1602. Valve assembly 104' may include (i) adjustable outlet lock 112 on a distal end of the valve assembly 104' and (ii) an attachment system 1608 on a proximal end of the valve assembly 104'. The attachment system 1608 is configured to attach to distal end 1606 of indwelling catheter. Any suitable attachment system for connecting to distal end 1606 is possible. In an example, a person may engage attachment system 1608 with distal end 1606 and twist the valve assembly 104' and/or attachment system 1608 so that attachment system 1608 connects to distal end 1606. After connecting valve assembly 104' to indwelling catheter 1602, a user may control adjustable outlet lock 112 (e.g., open and close adjustable outlet lock 112 as shown in FIG. 16) to drain fluid from the body cavity as desired.

Turning next to FIG. 17, FIG. 17 illustrates an example process for connecting valve assembly 104' to an indwelling catheter 1702. In this example, indwelling catheter 1702 may be damaged and leaking (e.g., through slit 1703 in indwelling catheter 1702). Indwelling catheter 1702 may be clamped of proximate to the person in which indwelling catheter 1702 is implanted, and indwelling catheter 1702 may then be cut cleanly, thereby removing the damaged section with slit 1703. Valve assembly 104' may include (i) adjustable outlet lock 112 on a distal end of the valve assembly 104' and (ii) an attachment system 1708 on a proximal end of the valve assembly 104'. The attachment system 1708 is configured to attach to distal end 1706 of the tubing of indwelling catheter 1702. Any suitable attachment system for connecting to distal end 1706 of the tubing is possible. In an example, attachment system 1708 may be configured to provide an interference fit with distal end 1706 of the tubing of indwelling catheter 1702. However, other attachment systems are possible as well. After connecting valve assembly 104' to indwelling catheter 1702, a user may control adjustable outlet lock 112 (e.g., open and close adjustable outlet lock 112) to drain fluid from the body cavity as desired.

Example methods for facilitating draining of fluid from a body cavity and for draining fluid from a body cavity are also provided. Such methods could, for example, be carried out by fluid-management systems 100 or 100' as described with reference to FIGS. 1-17 and/or utilizing fluid-management systems 100 or 100'.

FIG. 18 shows a flowchart of an example method 1800 of fluid management. It should be understood that for this and other processes and methods disclosed herein, flowcharts show functionality and operation of one possible implementation of present embodiments. Alternative implementations are included within the scope of the example embodiments of the present disclosure in which functions may be executed out of order from that shown or discussed, including substantially concurrent or in reverse order, depending on the functionality involved, as would be understood by those reasonably skilled in the art.

At block 1802, method 1800 involves providing a fluid-management system for selectively draining fluid from a body cavity. The fluid-management system comprises a valve assembly and a tube for carrying fluid from a body cavity of a person to the valve assembly, where the valve assembly is configured to be positioned external to the person's body and comprises (i) an inlet, (ii) an outlet, (iii) one or more one-way valves positioned between the inlet and outlet that are each configured to open and close based on fluctuations in pressure between a cavity of a person's body and the one-way valve, and (iv) an adjustable outlet lock configured to selectively prevent fluid movement through the outlet. At block 1804, method 1800 involves implanting a portion of the fluid-management system into the person's body, such that a proximal end of the tube is in fluid communication with the cavity and the valve assembly is positioned external to the person's body. At block 1806, after the fluid-management system is implanted into the person's body, the person may selectively drain fluid from the body cavity using the fluid-management system, as described above.

FIG. 19 shows a flowchart of an example method 1900 of draining fluid from a body cavity of a person to a reservoir external to the person's body. In particular, method 1900 is a method of operation of a fluid-management system comprising a valve assembly and a tube for carrying fluid from a body cavity of a person to the valve assembly, where the valve assembly is configured to be positioned external to the person's body and comprises (i) an inlet, (ii) an outlet, (iii) one or more one-way valves positioned between the inlet and outlet that are each configured to open and close based on fluctuations in pressure between a cavity of a person's body and the one-way valve, and (iv) an adjustable outlet lock configured to selectively prevent fluid movement through the outlet. At block 1902, method 1900 involves while the adjustable outlet lock is in a locked position, the adjustable outlet lock preventing fluid movement through the outlet. At block 1904, method 1900 involves while the adjustable outlet lock is in an unlocked position, each of the one or more one-way valves opening and closing based on fluctuations in pressure between the person's body cavity and the one-way valve, so as to provide a pumping action to move fluid from the body cavity through the tube, into the inlet, and out of the outlet to an exterior reservoir. The fluctuations may occur based on respiratory action of a breathing cycle of the person.

FIG. 20 shows a flowchart of an example method 2000 of draining fluid from a body cavity of a person to a reservoir external to the person's body. In particular, method 2000 is a method of operation of a fluid-management system comprising a valve assembly and a tube for carrying fluid from a body cavity of a person to the valve assembly, wherein the valve assembly is positioned external to the person's body and comprises (i) an inlet, (ii) an outlet, (iii) a plurality of one-way valves positioned between the inlet and outlet and that are each configured to open and close based on fluctuations in pressure between the person's body cavity and the one-way valve, wherein the plurality of one-way valves are housed in a pumping chamber, and (iv) an adjustable outlet lock configured to selectively prevent fluid movement through the outlet.

At block 2002, method 2000 involves, while the adjustable outlet lock is in a locked position, an external portion of the fluid-management system attaching to a body of the person. In an example, the fluid-management system attaches to a chest wall of the person. At block 2004, method 2000 involves, while the adjustable outlet lock is in an unlocked position, the pumping chamber compressing and decompressing, so as to provide a pumping action to prime the fluid-management system and get fluid moving through the fluid-management system. Further, at block 2006, method 2000 involves, while the adjustable outlet lock is in the unlocked position, after the fluid-management system is primed, and while the pump chamber is positioned below a level of fluid in the body cavity, the fluid-management system siphoning fluid from the body cavity through the fluid-management system. The fluid may be drained to a reservoir external to the person's body. In an example, the pump chamber 402 is shown positioned below a level of fluid in the body cavity in FIG. 4B. However, in other examples, the tube may be longer and may be positioned further below the level of fluid in the body cavity.

Figures 21A, 21B, 21C:
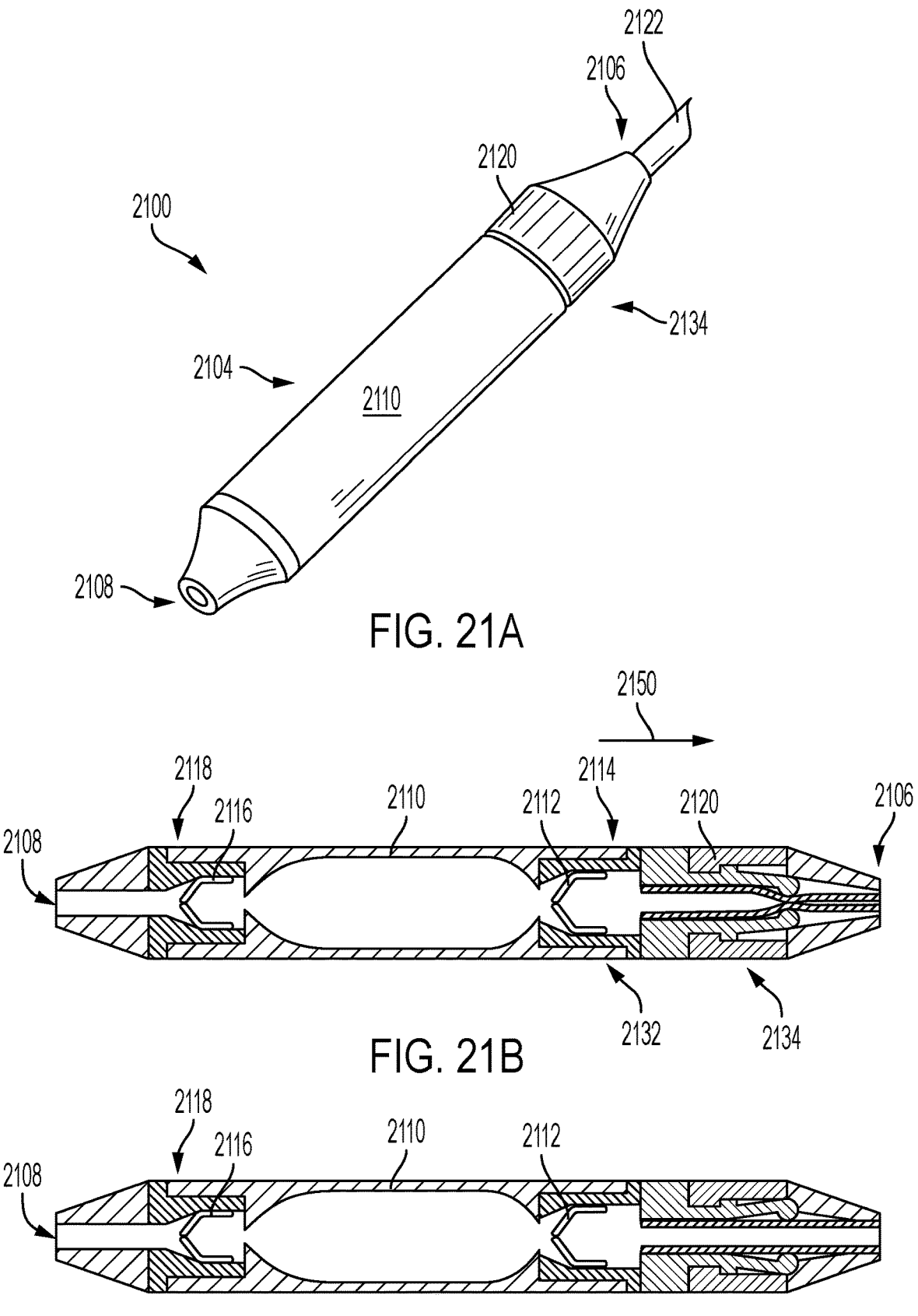
FIG. 21A illustrates an example fluid-management system, according to an example of the present disclosure.
FIG. 21B illustrates a cross-sectional view of a valve assembly of the example fluid-management system of FIG. 21A with an adjustable inlet lock in a locked position, according to an example of the present disclosure.
FIG. 21C illustrates a cross-sectional view of a valve assembly of the example fluid-management system of FIG. 21A with an adjustable inlet lock in an unlocked position, according to an example of the present disclosure.
Figure 21D:
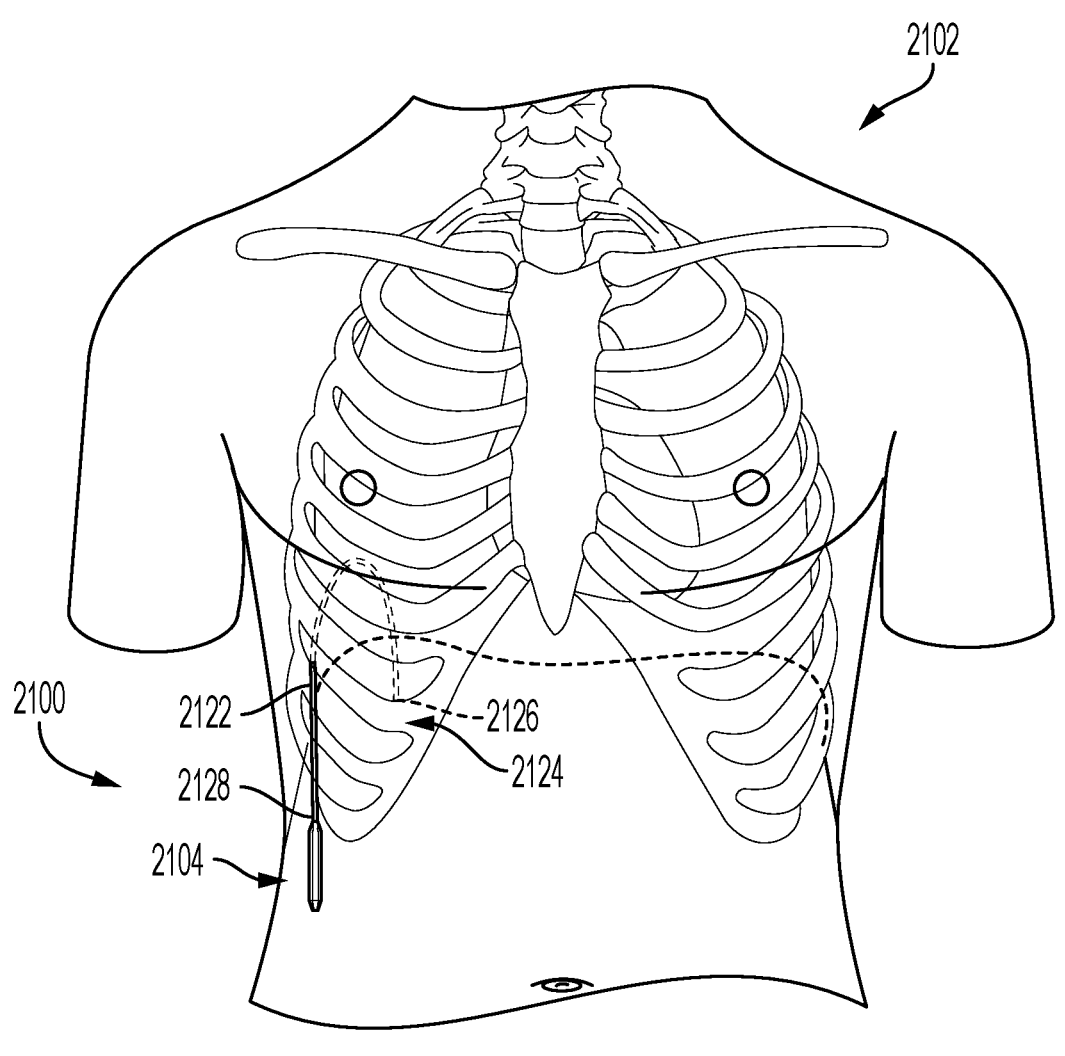
FIG. 21D illustrates the example fluid-management system of FIG. 21A implanted in a person.

FIGS. 21A-C depict an example fluid-management system 2100 and FIG. 21D depicts the fluid-management system 2100 implanted in a person's body 2102. Fluid-management system 2100 includes a valve assembly 2104 having an inlet 2106, an outlet 2108, a pumping chamber 2110 between inlet 2106 and outlet 2108 and configured to be compressed and decompressed to pump fluid, a first one-way valve 2112 (see FIGS. 21B-C) positioned on a first side 2114 of pumping chamber 2110 (e.g., the end of pumping chamber 2110 near inlet 2106), a second one-way valve 2116 (see FIGS. 21B-C) positioned on a second side 2118 of pumping chamber 2110 (e.g., the end of pumping chamber 2110 near outlet 2108), and an adjustable inlet lock 2120 configured to selectively prevent fluid movement through inlet 2106.

Fluid-management system 2100 also includes a fluid-management tube 2122 for carrying fluid from body cavity 2124 (see FIG. 21D) to valve assembly 2104. Tube 2122 is configured to extend from inlet 2106 to body cavity 2124 and allow movement of fluid from body cavity 2124 to inlet 2106 of valve assembly 2104. Tube 2122 is implanted in person's body 2102, such that a proximal end 2126 of tube 2122 is positioned within body cavity 2124 and a distal end 2128 is positioned external to body 2102. Further, valve assembly 2104 is positioned external to the person's body 2102.

In some examples, tube 2122 may have a cuff along its length that can be placed within the tissues of person's body 2102 near the exit of tube 2122 from person's body 2102. Such a cuff may, for example, be constructed from fibers made of a material that allows tissue ingrowth into the fibers of the cuff, forms a barrier to bacterial entry, and helps secure tube 2122 in place over time. For instance, such a cuff may be constructed from a material such as polyethylene terephthalate, among other possibilities. Further, in some examples, tube 2122 may have a feature along its length configured to allow securing of the tube using a suture material to person's body 2102.

Body cavity 2124 may be a cavity in person's body 2102 that may build up fluid for which there is a desire or need to selectively drain out of the body. In the example of FIG. 21A-D, body cavity 2124 is a pleural cavity of person's body 2102. However, other body cavities are possible, such as a peritoneal cavity, a cerebrospinal cavity, a pericardial cavity, a breast cavity, or a cavity of a cystic lesion, among other possibilities.

Figure 22A:
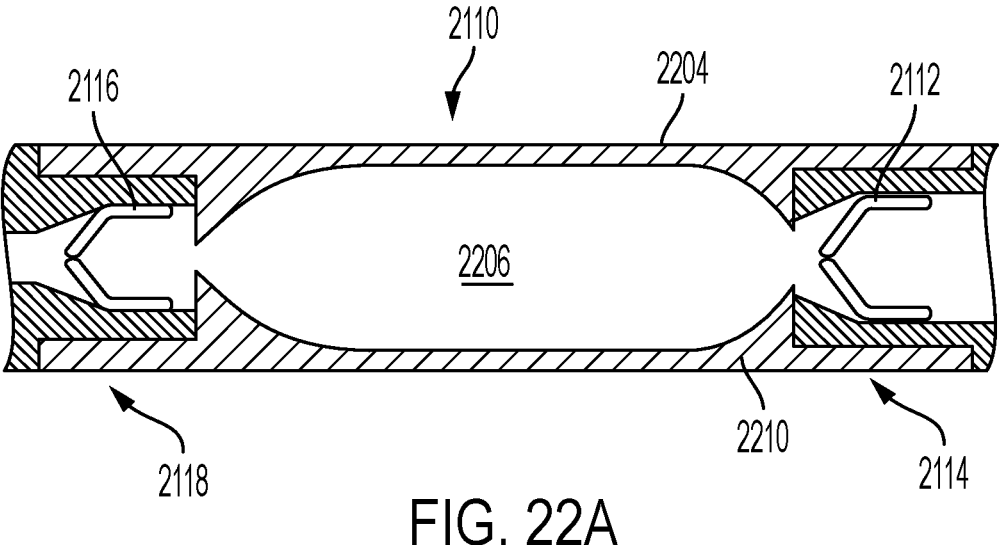
FIGS. 22A-D illustrates a pumping chamber of the fluid-management system of FIG. 21A at various stages of compression and decompression, according to an example of the present disclosure.

Each of first one-way valve 2112 and second one-way valve 2116 is configured to open and close based on compression and decompression of pumping chamber 2110. Compression and decompression of pumping chamber 2110 is described further with respect to FIGS. 22A-D. In particular, FIG. 22A shows a cross-sectional schematic view of pumping chamber 2110 of valve assembly 2104 in a generally or substantially non-compressed state with both first one-way valve 2112 and second one-way valve 2116 closed. For clarity, first one-way valve 2112 is also referred to herein as an "inlet one-way valve," and second one-way valve 2116 is referred to as an "outlet one-way valve." Inlet one-way valve 2112 is positioned on first side 2114 of pumping chamber 2110 proximate to the inlet of valve assembly 2104 and outlet one-way valve 2116 is positioned on second side 2118 of pumping chamber 2110 proximate to outlet 2108 of valve assembly 2104.

Figure 22B:
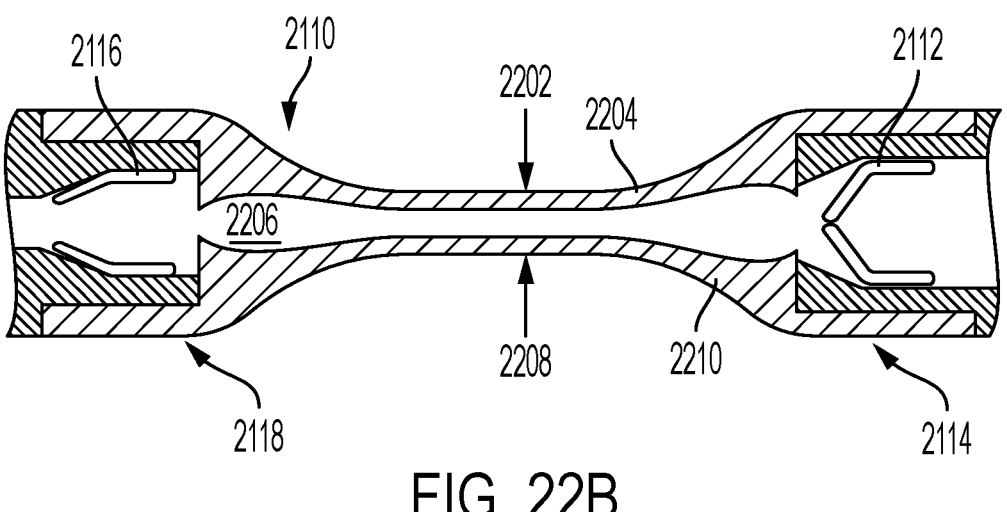

FIG. 22B shows a cross-sectional schematic view of valve assembly 2104 in a generally or substantially compressed state. In an example, as shown, a first force 2202 may act on a first wall 2204 causing first wall 2204 to collapse in towards interior space 2206. Correspondingly, a second force 2208 may additionally or alternatively act on a second wall 2210 causing second wall 2210 to collapse in towards interior space 2206.

First force 2202 and second force 2208 may be applied to pumping chamber 2110 in any suitable fashion. As one possibility, a person using fluid-management system 2100 may supply the forces by manually compressing pumping chamber with their fingers. As another possibility, valve assembly 2104 may include an electromechanical actuator configured to apply forces 2202 and 2208. For instance, valve assembly 2104 may include a piezoelectric diaphragm connected to the body of pumping chamber 2110. The piezoelectric diaphragm may be activated and inactivated by a controller, and both the piezoelectric diaphragm and the controller may be powered, e.g., by a battery. As another example, valve assembly 2104 may include a piston or cam configured to apply forces 2202 and 2208 to pumping chamber 2110. Other example methods and systems for applying forces 2202 and 2208 are possible as well.

The collapse of the first wall 2204 and/or second wall 2210 serves to decrease the volume of interior space 2206 and to increase the pressure in interior space 2206. This increase in pressure causes inlet one-way valve 2112 to remain closed and causes outlet one-way valve 2116 to open, and fluid located in interior space 2206 to flow from interior space 2206 through outlet one-way valve 2116 and out outlet 2108 (see FIG. 21B-C). For incompressible fluids, the change of volume experienced by interior space 2206 in response to the collapse of first wall 2204 and/or second wall 2210 will be approximately equal to the volume of fluid that moves from interior space 2206 through outlet one-way valve 2116. As the fluid moves from interior space 2206 through outlet one-way valve 2116, the pressure in interior space 2206 will decrease. Once the interior pressure equals or substantially equals the pressure in outlet 2108, flow will stop and outlet one-way valve 2116 will close as shown in FIG. 22C.

In some examples, the cracking pressure and resealing pressure of each of inlet one-way valve 2112 and outlet one-way valve 2116 may be the same as or similar to the cracking pressure and resealing pressure of one-way valve 110, one-way valve 110', and/or one-way valve 110" (and thus the cracking pressure and resealing pressure of each of inlet one-way valve 2112 and outlet one-way valve 2116 are not described in as great of detail). It should be understood, however, that any of the possibilities and permutations described with respect to the cracking pressure and resealing pressure of one-way valve 110, one-way valve 110', and/or one-way valve 110" are also possible with respect to the cracking pressure and resealing pressure of each of inlet one-way valve 2112 and outlet one-way valve 2116.

Figure 22C:
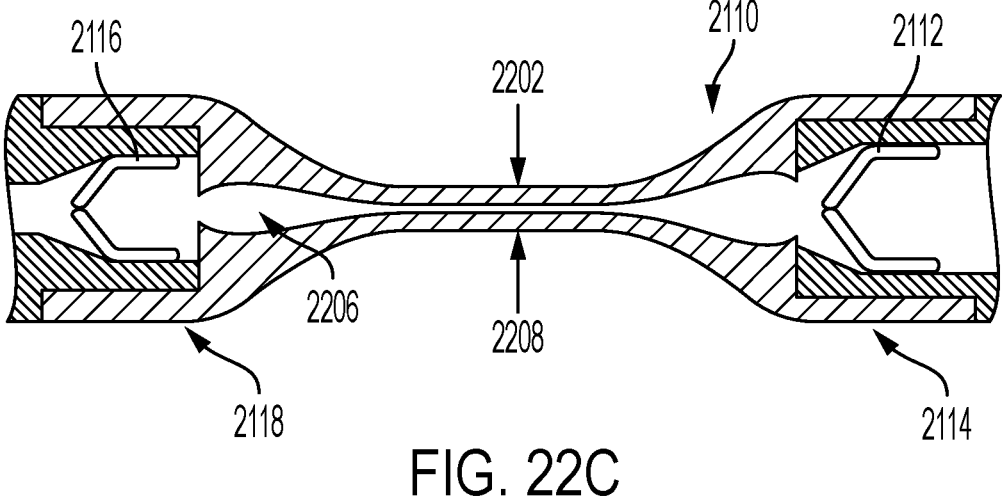
Figure 22D:
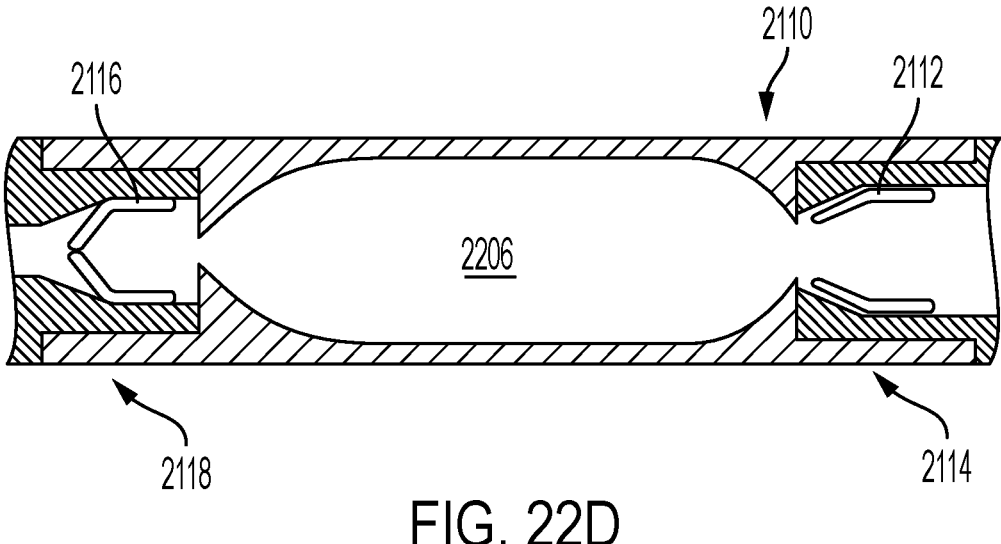

As described above, the body of pumping chamber 2110 may be substantially resiliently flexible and therefore, after being placed in a compressed state as shown in FIGS. 22B and 22C, valve assembly 2104 will return to an uncompressed state as shown in FIGS. 22A and 22D when at least one of the first force 2202 and the second force 2208 are removed. As the first wall 2204 returns to its uncompressed state as the first force 2202 is removed and/or the second wall 2210 returns to its uncompressed state as the second force 2208 is removed, the volume of the interior space 2206 increases and the pressure in the interior space 2206 decreases. The pressure inside the interior space 2206 eventually drops sufficiently below the pressure on the inlet 2106 near inlet one-way valve 2112 and causes inlet one-way valve 2112 to open and fluid located in the inlet to flow into the interior space 2206. In this way, valve assembly 2104 operates as a pump that, generally, draws fluid from inlet 2106 and passes it to outlet 2108.

In some examples, pumping chamber 2110 may be made of material that allows for pumping chamber 2110 to be compressed and then freely returned to its original state. Pumping chamber 2110 may be made of any suitable material. For example, pumping chamber 2110 may be a resiliently flexible tube, cylinder, or other appropriate shape made of polyurethane, silicone, polyvinyl chloride, or latex rubber. Alternatively, pumping chamber 2110 may be made of a combination of two or more materials where at least one of the component materials provides resilience and at least one of the component materials provides fluid containment. For example, pumping chamber 2110 may be composed of an elastic nitinol, steel, polyester, or other elastic component to provide for resiliency and a second fluid containment component such as polyurethane, silicone, polyvinyl chloride, latex rubber, polyethylene terephthalate, nylon, polytetrafluoroethylene, polyether block amide such as PEBAX®, or the like to provide fluid containment within pumping chamber 2110. In other examples, such as examples where valve assembly 2104 includes an electromechanical actuator (e.g., a piezoelectric diaphragm, piston, or cam configured to apply forces 2202 and 2208 to pumping chamber 2110), the material may be flexible but not resilient (or having limited resilience), as an electromechanical actuator may provide both active compression and active rarefication.

In some examples, first one-way valve 2112 and second one-way valve 2116 each have the capacity to open an amount such that the cross-sectional area of the passage through the one-way valve in the open position is larger than the cross-sectional area of the lumen of inlet 2106, such that any debris that may be able to enter into inlet 2106 and/or tube 2122 can pass through the one-way valve.

In an example, adjustable inlet lock 2120 is positioned upstream (in the direction of arrow 2150 (see FIG. 21B)) of first one-way valve 2112. For instance, with reference to FIG. 21B, the first one-way valve 2112 may be positioned within pumping chamber 2110 at position 2132, and adjustable inlet lock 2120 is upstream (in the direction of arrow 2150) of the first-one way valve 2112 at position 2134.

Figure 23A:
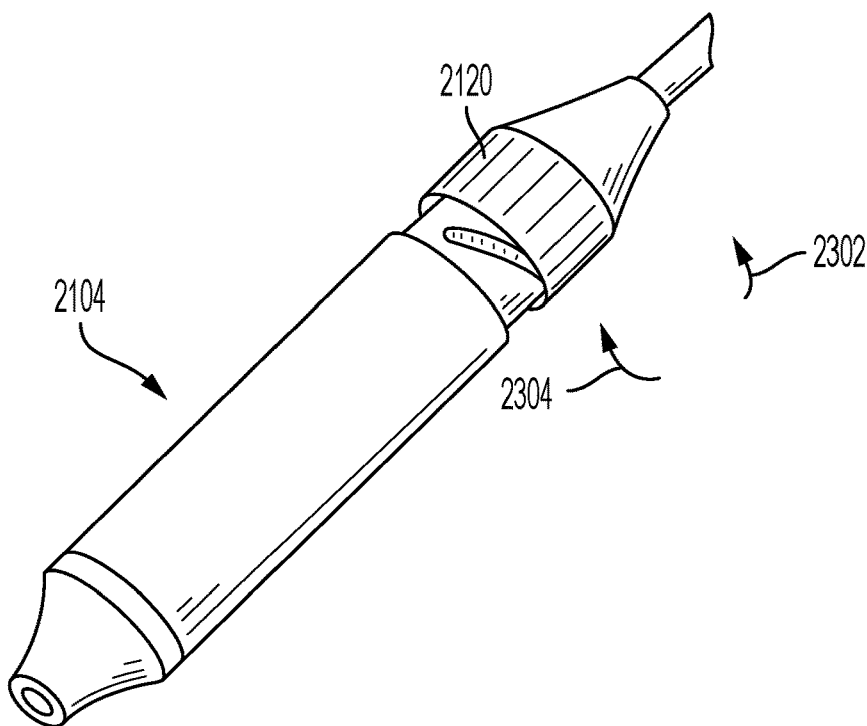
FIGS. 23A-B illustrates the fluid-management system of FIG. 21A at various stages of compression and decompression of the pumping chamber, according to an example of the present disclosure.
Figure 23B:
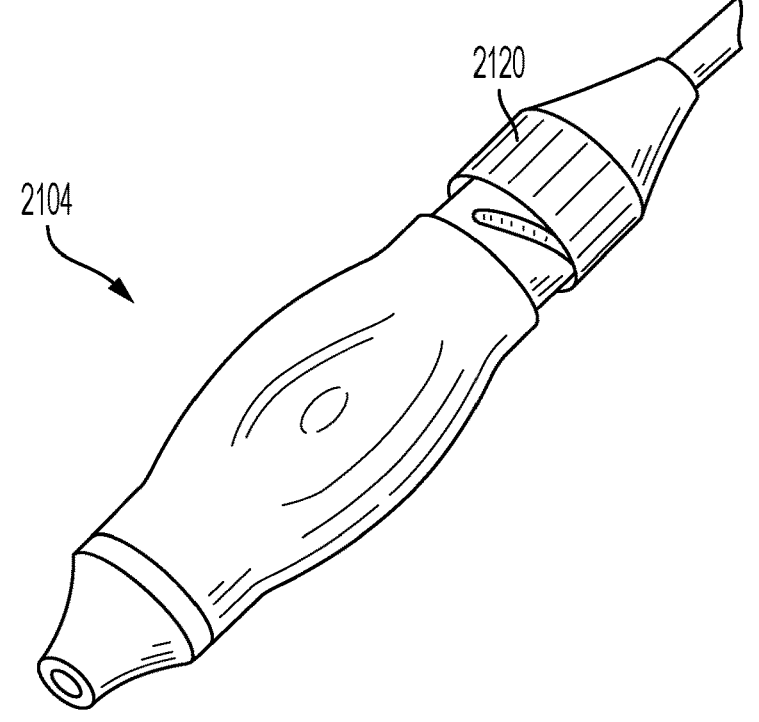

In the example of FIGS. 21A-D, adjustable inlet lock 2120 is illustrated as a twist lock configured to pinch tube 2122 and/or inlet 2106. For instance, FIGS. 21A-B illustrate adjustable inlet lock 2120 in the closed positioned (e.g., in which the twist lock pinches tube 2122 positioned at inlet 2106), and FIGS. 21C and 23A-B illustrate adjustable inlet lock 2120 after adjustable inlet lock 2120 has been rotated in direction 2302 to be in the open position (e.g., in which the twist lock no longer pinches tube 2122 at inlet 2106). The rotation may cause the twist lock to move from the closed position to the open position. Further, rotation in the opposite direction 2304 moves adjustable inlet lock 2120 from the open position to the closed position. The twist lock of FIGS. 21A-D functions in a manner similar to the twist cap described with reference to FIGS. 8A-D (e.g., twist lock configured to activate pinch arms to pinch tube 2122 at inlet 2106) and thus is not described in as great of detail.

Although in the example of FIGS. 21A-D, adjustable inlet lock 2120 takes the form of a twist lock, various adjustable inlet locks 2120 are possible. For instance, adjustable inlet lock 2120 may take the form of a twist pinch, a pinch level, and an offset device (e.g., forms similar to the forms of the outlet locks illustrated in FIGS. 6A-B, 7A-B, 9A-C, and 10A-B), among other possibilities.

Operation of the fluid-management system 2100 is described with reference to FIGS. 21D and 24A-D. In order to initiate the draining process, a person may first select an external reservoir 2402 (see FIG. 24C) in which to drain the fluid from body cavity 2124. In general, the person may drain the fluid into any appropriate reservoir such as a sink, a commode, and/or a container provided by the person, among other possibilities. Further, prior to initiating drainage, the valve assembly area may be cleaned with soap and water and/or decontaminated with alcohol, betadine, or chlorhexidine, among other possibilities. In some examples, when the valve assembly is closed (and/or when open as well), there is clearance so that if alcohol or soap and water were poured over the locking portion and/or the outlet portion of the fluid management system (or if this portion were dunked into such fluid), the alcohol or soap and water can easily flow between the locking mechanism and outlet tubing to provide a more thorough decontamination. Next, to initiate the draining process, the person may point outlet 2108 upward and switch adjustable inlet lock 2120 to the unlocked position (see FIG. 24A).

Figure 24A:
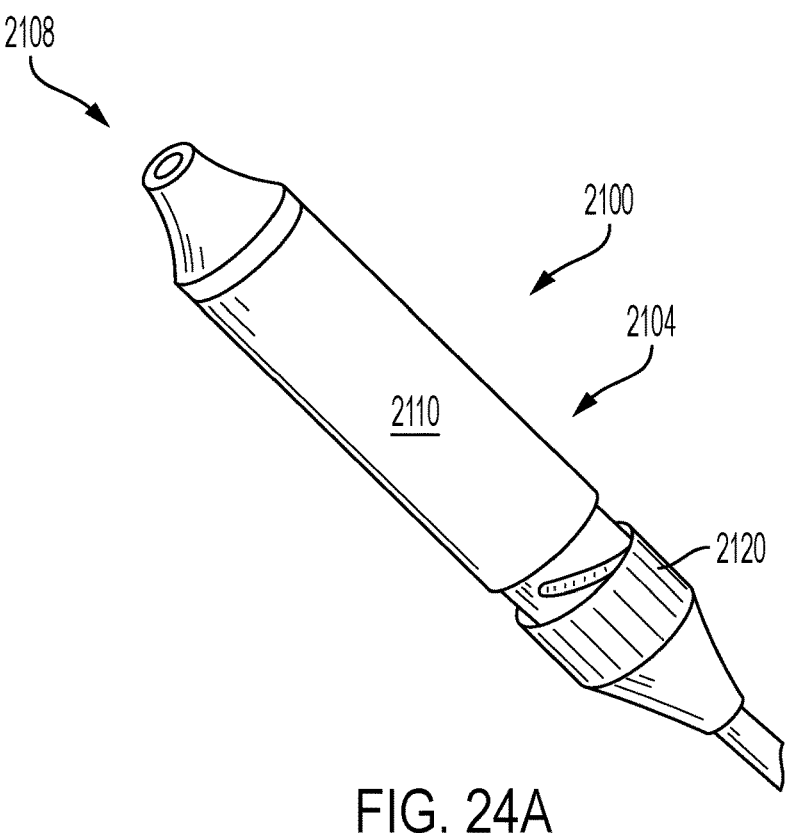
FIGS. 24A-D illustrate various stages of operation of the example fluid-management system of FIG. 21A, according to an example of the present disclosure.
Figure 24B:
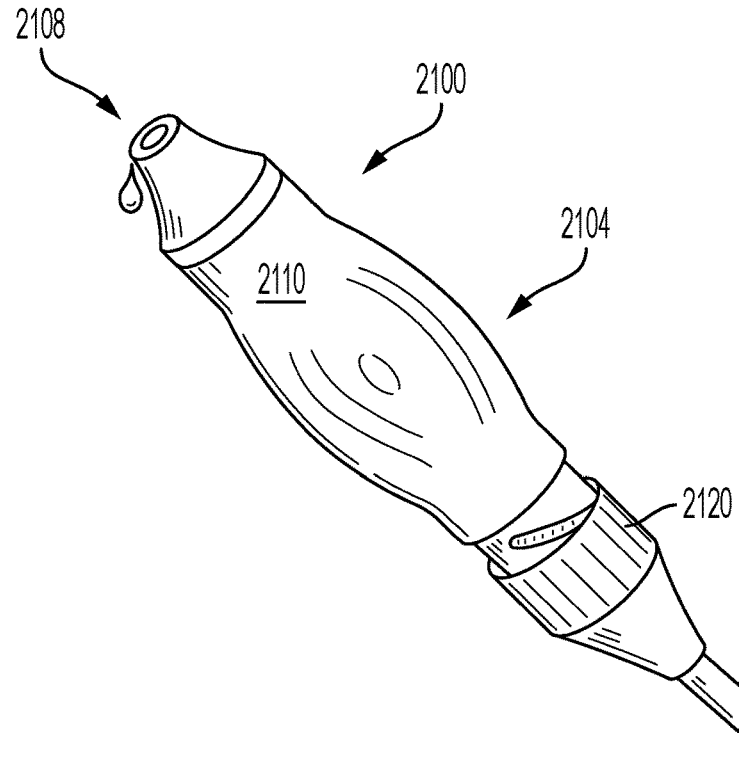
Figure 24C:
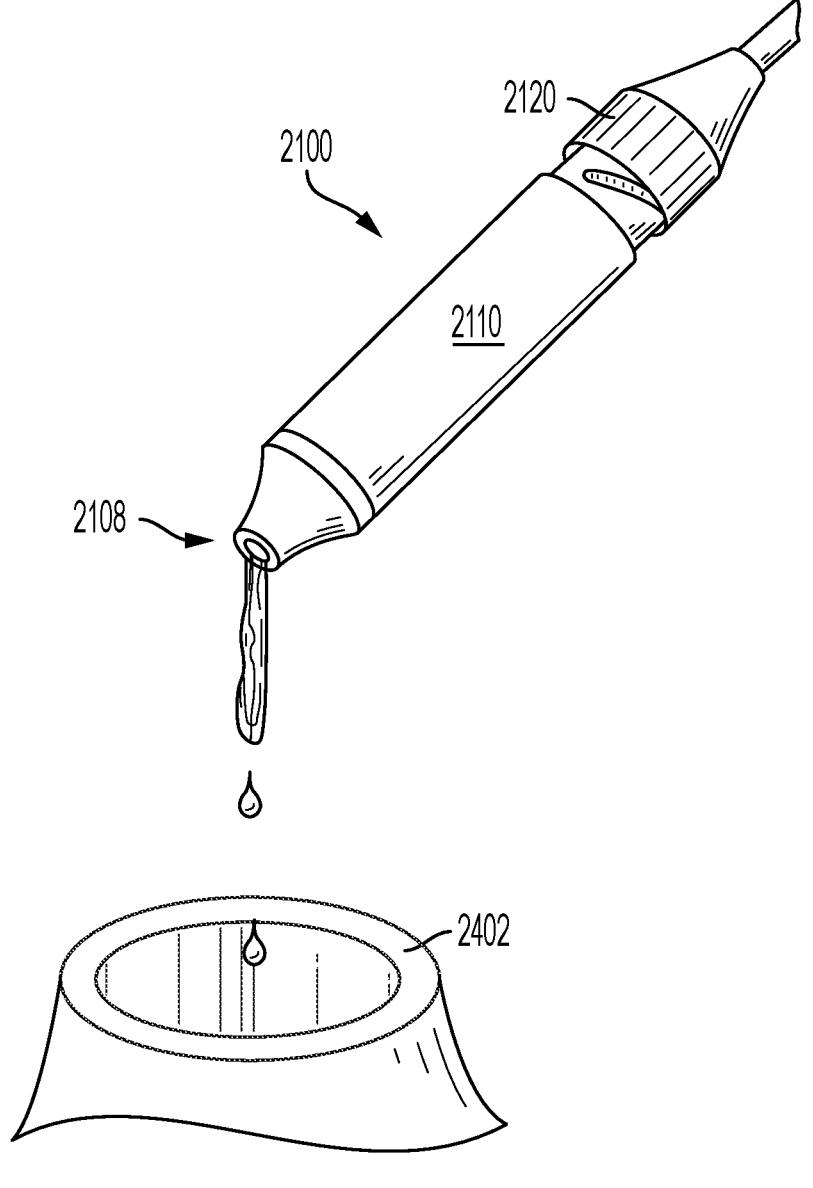
Figure 24D:
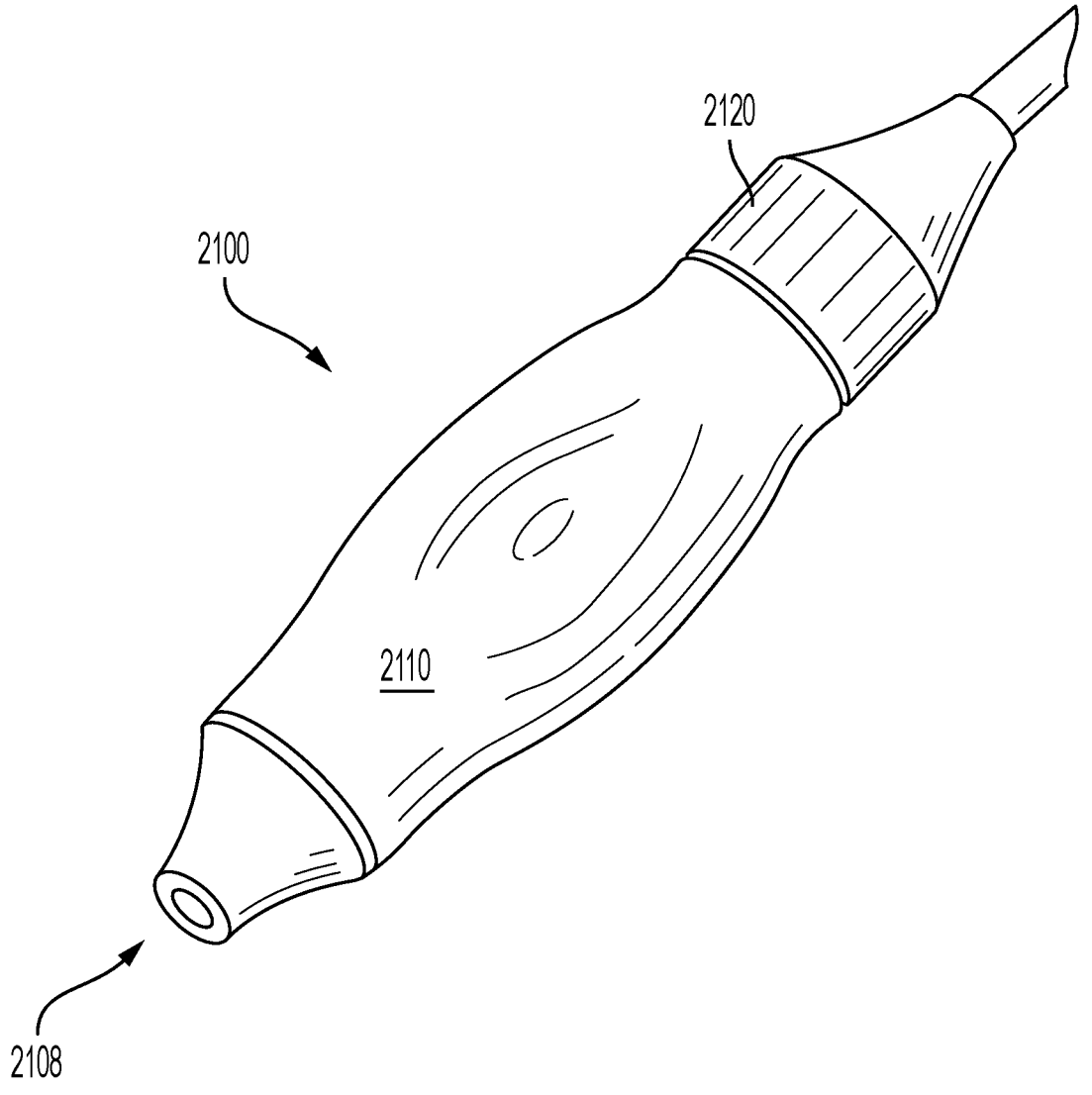

With outlet 2108 pointed upward and adjustable inlet lock 2120 in the unlocked position, the person may alternately compress and decompress pumping chamber 2110 until pumping chamber 2110 is full or substantially full of fluid (see FIG. 24B compared to FIG. 24A). When pumping chamber 2110 is full or substantially full of fluid, the person may then point outlet 2108 downward and move outlet 2108 below the level of insertion (see FIG. 24C) and/or to a position that is sufficiently low so as to allow a siphoning action to be initiated and fluid to begin to flow. At this level, siphoning flow begins and fluid may be drained into external reservoir 2402. The flow rate may be controlled by adjusting the height of the outlet relative to insertion site and flow may be augmented by manually compressing the pump chamber. Once drainage has stopped, the person may once again alternately compress and decompress pumping chamber 2110 to drain additional fluid from body cavity 2124, if desired. In an example, the length of tube 2122 (and, more particularly, the length of the portion of tube 2122 that is external to the body) may be set to control a vacuum level and/or a maximum vacuum that the siphon produces and/or may produce. Further, in some examples, the one-way valves, tubing diameter, and/or tubing length can be selected so as to ensure a desired minimum flow rate, such as 25 milliliters per minute (ml/min) or greater, 50 ml/min or greater, 75 ml/min or greater, 100 ml/min, 125 ml/min or greater, 150 ml/min or greater, 175 ml/min or greater, among other possibilities.

Once desired drainage is complete, the person may move adjustable inlet lock 2120 to the locked position (see FIG. 24D), thereby isolating tube 2122 and body cavity 2124. Pumping chamber 2110 may then be compressed, thereby emptying pumping chamber 2110 and placing it under vacuum as the resilient pumping chamber 2110 attempts to recoil (see FIG. 24D). Finally, the person may clean or decontaminate outlet 2108 (clean with soap and water and/or decontaminate with alcohol, betadine, or chlorhexidine, among other possibilities).

Closing adjustable inlet lock 2120 fully isolates pumping chamber 2110 from the tube 2122 and body cavity 2124. This isolation may prevent entry of additional fluid from tube 2122 and/or body cavity 2124 into pumping chamber 2110. In a situation where there is not an inlet lock between the tube 2122 and the inlet of the valve assembly, over time (e.g., between drainage sessions when the user is not actively draining fluid from the body cavity) fluid from the body cavity will flow into the pumping chamber via the inlet and the inlet one-way valve. In such a situation where there is not an inlet lock between the tube 2122 and the inlet of the valve assembly, while the one-way valve prevents backflow (and thus fluid from the pump chamber is isolated from moving back towards the body cavity), fluid from the body cavity may still enter the pump chamber via the inlet one-way valve. On the other hand, beneficially, the adjustable inlet lock 2120 can isolate pumping chamber 2110 from body cavity 2124, such that fluid from the body cavity is unable to flow into pumping chamber 2110 when adjustable inlet lock 2120 is in the locked position.

This isolation provides redundant protection against backflow of fluid from pumping chamber 2110 into tube 2122 and/or body cavity 2124, as well as protection against ingress of bacteria into tube 2122 and/or body cavity 2124. In particular, not only does one-way valve 2112 provide protection against both (i) backflow of fluid from pumping chamber 2110 into tube 2122 and/or body cavity 2124 and (ii) ingress of bacteria into tube 2122 and/or body cavity 2124, but the isolation provided by adjustable inlet lock 2120 also provides protection against both (i) backflow of fluid from pumping chamber 2110 into tube 2122 and/or body cavity 2124 and (ii) ingress of bacteria into tube 2122 and/or body cavity 2124.

Further, with second one-way valve 2116 and adjustable inlet lock 2120 closed, compression of the resilient pumping chamber 2110 will evacuate the contents of pumping chamber 2110 and place pumping chamber 2110 under a vacuum. The evacuation of fluid and/or the vacuum at this stage have multiple advantages. For instance, as one example, beneficially, lack of fluid in pumping chamber 2110 means that accidental compression of pumping chamber 2110 between uses (e.g., such as accidental compression caused by the person laying on pumping chamber 2110 between uses) means that pumping chamber 2110 will not be over pressurized. In some situations, if the pumping chamber was over pressurized and compressed with a high force (e.g., inadvertent compression such as being laid on or sat on), there may be a risk of damage to one or more components of the valve assembly (e.g., damage to one or more of the one-way valves, the joints between a one-way valve and the pumping chamber body, and/or the body of the pumping chamber, among other possibilities). Ensuring that pumping chamber 2110 will not be over pressurized may help to reduce or limit a potential for risk of damage to one or more components of the valve assembly due to over pressurization of pumping chamber 2110.

As another example, lack of fluid in pumping chamber 2110 helps to prevent clotting within pumping chamber 2110. If biological materials are sitting static in pumping chamber 2110 and these biological materials can clot, there may be a risk that the material may clot. The biological material may include proteins that act as clotting factors, and leaving such material in pumping chamber 2110 for a threshold period of time (e.g., 6 hours or more, 12 hours or more, 24 hours or more, and/or 48 hours or more) may lead to larger strand fiber formation and/or larger clot formation. Clotting may act to clog valve assembly 2104 and make valve assembly 2104 non-functional. Additionally or alternatively, clotting may increase risk of damage to one or more components of the valve assembly (e.g., damage to one or more of the one-way valves and/or the joints between a one-way valve and the pumping chamber body, among other possibilities), so preventing or limiting clotting may beneficially prevent or reduce risk of damage to one or more components of the valve assembly.

As another example, lack of fluid in pumping chamber 2110 also means that there is less biological material within fluid-management system 2100, such that if bacteria were to ingress into pumping chamber 2110 during use of fluid-management system 2100, there is less material within which that bacteria may grow. Bacteria may lead to an infection and thus it may be desirable to prevent or limit bacteria growth within the fluid-management system. Biological material may include proteins and/or solute that may act as a bacterial medium in which bacteria may grow. Lack of fluid in pumping chamber 2110 may prevent or limit bacterial medium in the pumping chamber.

Further, the placement of valve assembly 2104 of fluid-management system outside of the person's body may also help to prevent or limit bacterial growth/activity. In this regard, given the placement of valve assembly 2104 outside the person's body, temperature in pumping chamber 2110 would also be lower than temperature within the person's body, which serves to limit or decrease rate of bacterial growth/activity and also limit or decrease rate of clot formation.

As yet another example, the maintained vacuum within pumping chamber 2110 also provides a biasing pressure gradient to limit or prevent bacterial ingress from pumping chamber 2110 into tube 2122 and subsequently into body cavity 2124. In this regard, while first one-way valve 2112 and adjustable inlet lock 2120 both provide an impediment to fluid moving from pumping chamber 2110 into tube 2122, in some situations, the valve assembly may have micropores or micro passageways between pumping chamber 2110 and tube 2122, and it may be possible for a small amount of fluid to move upstream from pumping chamber 2110 to tube 2122 via micropores or micro passageways into tube 2122. Therefore, in a scenario where bacteria were to get into valve assembly 2104, it may be possible for bacteria to move upstream from pumping chamber 2110 to tube 2122 via micropores or micro passageways into tube 2122.

However, a biasing pressure gradient provided by a maintained vacuum within pumping chamber may make it more difficult for fluid to move upstream from pumping chamber 2110 to tube 2122 via micropores or micro passageways into tube 2122 (compared to a situation in which there is no maintained vacuum in the pumping chamber). Since the pressure gradient may make it difficult for fluid to move upstream, the fluid will remain in pumping chamber 2110 and be unable to move moving upstream from pumping chamber 2110 to tube 2122 via micropores or micro-passageways in the valve assembly.

As an illustrative example, in a situation where the pumping chamber is at a $-10$ cmH$_2$O pressure and tube 2122 is at atmospheric pressure, fluid may have more difficulty moving upstream from pumping chamber 2110 to tube 2122 via micropores or micro-passageways in valve assembly 2104 compared to a situation where a pumping chamber is at atmospheric pressure and a tube is at atmospheric pressure. Therefore, the biasing pressure gradient provided by a maintained vacuum provides an additional impediment to bacterial ingress from pumping chamber 2110 into tube 2122. In particular, not only do one-way valve 2112 and adjustable inlet lock 2120 provide an impediment to bacterial ingress from pumping chamber 2110 into tube 2122, but the biasing pressure gradient provided by the maintained vacuum within pumping chamber 2110 provides an additional impediment to bacterial ingress from pumping chamber 2110 into tube 2122.

In some examples, valve assembly 2104 is non-removably attached to tube 2122. Further, in some examples, adjustable inlet lock 2120 of valve assembly 2104 is non-removably attached to valve assembly 2104.

As mentioned above, each of first one-way valve 2112 and second one-way valve 2116 is configured to open and close based on compression and decompression of pumping chamber 2110. In some examples, each of first one-way valve 2112 and second one-way valve 2116 is further configured to open and close based on fluctuations in pressure between the person's body cavity 2124 and the one-way valve that occur based on respiratory action of a breathing cycle of the person. For instance, in some examples, first one-way valve 2112 and second one-way valve 2116 are configured in the manner described above with respect to one-way valves 110, 110' and 110". It should be understood that any of the possibilities and permutations described with respect to one-way valves 110, 110' and 110" are also possible with respect to first one-way valve 2112 and second one-way valve 2116.

Figures 25A, 25B, 25C:
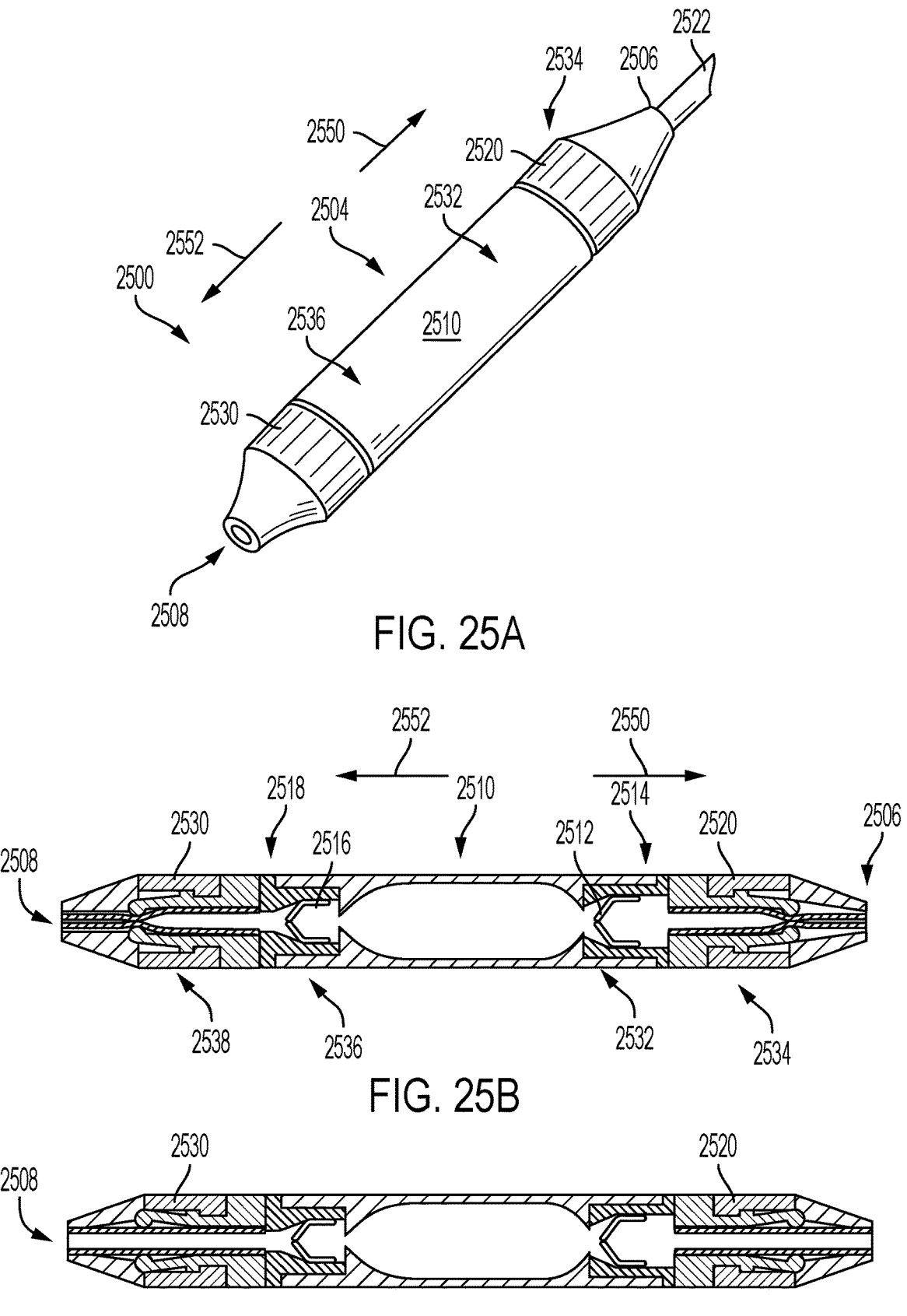
FIG. 25A illustrates an example fluid-management system, according to an example of the present disclosure.
FIG. 25B illustrates a cross-sectional view of a valve assembly of the example fluid-management system of FIG. 25A with an adjustable inlet lock in a locked position and an adjustable outlet lock in a locked position, according to an example of the present disclosure.
FIG. 25C illustrates a cross-sectional view of a valve assembly of the example fluid-management system of FIG. 25A with an adjustable inlet lock in an unlocked position and an adjustable outlet lock in an unlocked position, according to an example of the present disclosure.
Figure 25D:
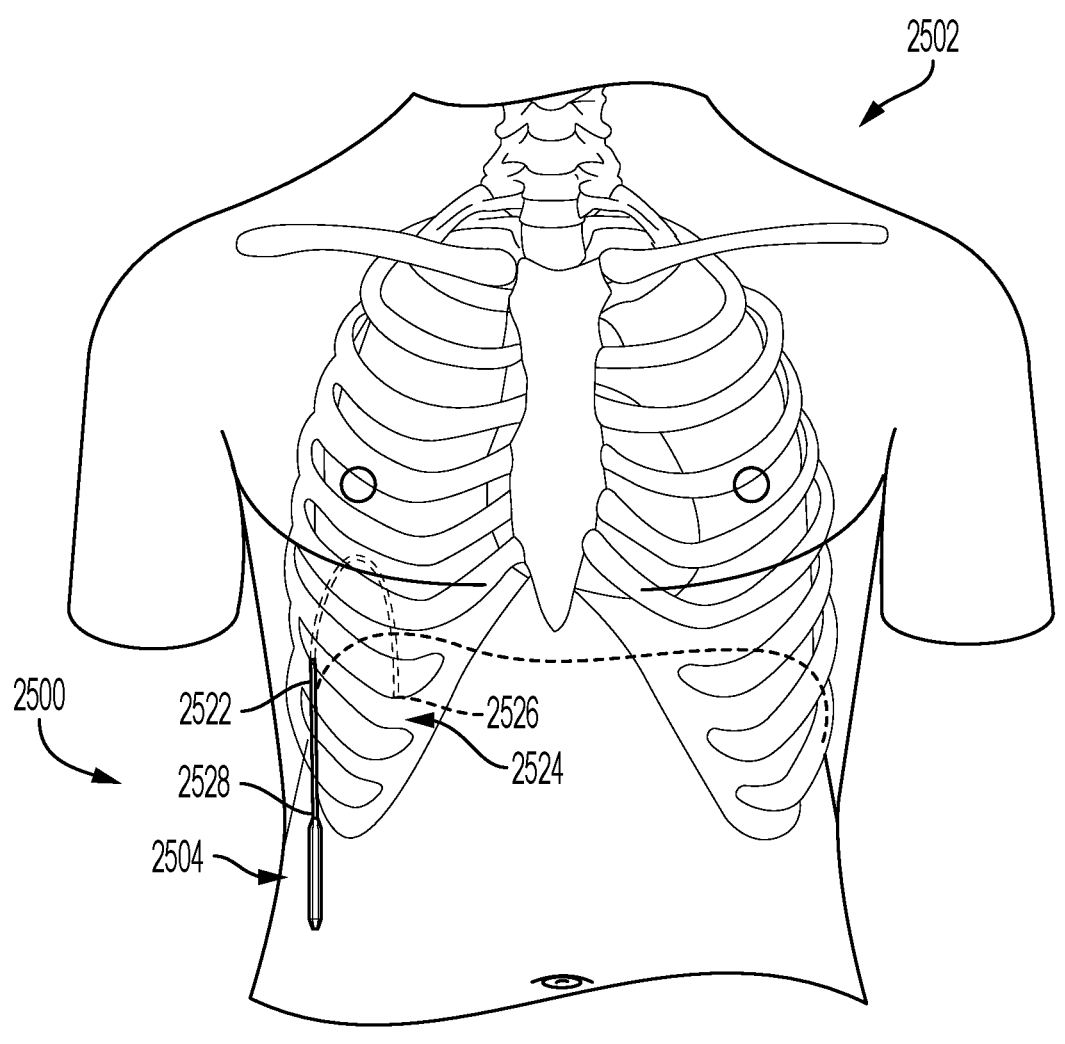
FIG. 25D illustrates the example fluid-management system of FIG. 25A implanted in a person.

In addition to or alternative to including an adjustable inlet lock such as adjustable inlet lock 2120, the fluid management system may include an adjustable outlet lock. For instance, FIGS. 25A-C depict an example fluid-management system 2500 and FIG. 25D depicts the fluid-management system 2500 implanted in a person's body 2502. Fluid-management system 2500 includes a valve assembly 2504 having an inlet 2506, an outlet 2508, a pumping chamber 2510 between the inlet and outlet and configured to be compressed and decompressed to pump fluid, a first one-way valve 2512 (see FIGS. 25B-C) positioned on a first side 2514 of pumping chamber 2510 (e.g., the end of pumping chamber near inlet 2506), a second one-way valve 2516 (see FIGS. 25B-C) positioned on a second side 2518 of pumping chamber 2510 (e.g., the end of pumping chamber 2510 near outlet 2508), an adjustable inlet lock 2520 configured to selectively prevent fluid movement through inlet 2506, and an adjustable outlet lock 2530 configured to selectively prevent fluid movement through outlet 2508.

Fluid-management system 2500 also includes a fluid-management tube 2522 for carrying fluid from body cavity 2524 to valve assembly 2504. Tube 2522 is configured to extend from inlet 2506 to body cavity 2524 and allow movement of fluid from cavity 2524 to inlet 2506 of valve assembly 2504. Tube 2522 is implanted in person's body 2502, such that a proximal end 2526 of tube 2522 is positioned within cavity 2524 and a distal end 2528 is positioned external to body 2502. Further, valve assembly 2504 is positioned external to the person's body 2502.

In some examples, tube 2522 may have a cuff along its length that can be placed within the tissues of person's body 2502 near the exit of tube 2522 from person's body 2502. Such a cuff may, for example, be constructed from fibers made of a material that allows tissue ingrowth into the fibers of the cuff, forms a barrier to bacterial entry, and helps secure tube 2522 in place over time. For instance, such a cuff may be constructed from a material such as polyethylene terephthalate, among other possibilities. Further, in some examples, tube 2522 may have a feature along its length configured to allow securing of the tube using a suture material to person's body 2502.

Cavity 2524 may be a cavity in person's body 2502 that may build up fluid for which there is a desire or need to selectively drain out of the body. In the example of FIG. 25A-D, cavity 2524 is a pleural cavity of person's body 2502. However, other body cavities are possible, such as a peritoneal cavity, a cerebrospinal cavity, a pericardial cavity, a breast cavity, or a cavity of a cystic lesion, among other possibilities.

Each of first one-way valve 2512 and second one-way valve 2516 is configured to open and close based on compression and decompression of pumping chamber 2510. Compression and decompression of pumping chamber 2510 is similar to the compression and decompression of pumping chamber 2110 as described with respect to FIGS. 22A-D, and thus is not described in as great of detail. It should be understood, however, that any of the possibilities and permutations described with respect to the compression and decompression of pumping chamber 2110 are also possible with respect to the compression and decompression of pumping chamber 2510. Similarly, the cracking pressure and resealing pressure of each of first one-way valve 2512 and second one-way valve 2516 may be the same as or similar to the cracking pressure and resealing pressure of the cracking pressure and resealing pressure of inlet one-way valve 2112 and outlet one-way valve 2116, and thus is not described in as great of detail. It should be understood, however, that any of the possibilities and permutations described with respect to the cracking pressure and resealing pressure of inlet one-way valve 2112 and outlet one-way valve 2116 are also possible with respect to the cracking pressure and resealing pressure of each of first one-way valve 2512 and second one-way valve 2516.

In an example, adjustable inlet lock 2520 is positioned upstream (in the direction of arrow 2550) of first one-way valve 2512 and adjustable outlet lock 2530 is positioned downstream (in the direction of arrow 2552) of second one-way valve 2516. For instance, with reference to FIG. 25B, first one-way valve 2512 may be positioned within pumping chamber 2510 at position 2532, and adjustable inlet lock 2520 is upstream of the first-one way valve 2512 at position 2534. Further, second one-way valve 2516 may be positioned within pumping chamber 2510 at position 2536, and adjustable outlet lock 2530 is downstream of the second one-way valve 2516 at position 2538.

In some examples, valve assembly 2504 is non-removably attached to tube 2522. Further, in some examples, adjustable inlet lock 2520 of valve assembly 2504 is non-removably attached to valve assembly 2504, and adjustable outlet lock 2530 is non-removably attached to valve assembly 2504.

Operation of the fluid-management system 2500 is described with reference to FIGS. 26A-E. In order to initiate the draining process, a person may first select an external reservoir 2600 (see FIG. 26C) in which to drain the fluid from cavity 2524. In general, the person may drain the fluid into any appropriate reservoir such as a sink, a commode, and/or a container provided by the person, among other possibilities. Further, prior to initiating drainage, the valve assembly area may be cleaned with soap and water and/or decontaminated with alcohol, betadine, or chlorhexidine, among other possibilities. In some examples, when the valve assembly is closed (and/or when open as well), there is clearance so that if alcohol or soap and water were poured over the locking portion and/or the outlet portion of the fluid management system (or if this portion were dunked into such fluid), the alcohol or soap and water can easily flow between the locking mechanism(s) and outlet tubing to provide a more thorough decontamination. Next, to initiate the draining process, the person may point the outlet 2508 upward, switch adjustable inlet lock 2520 to the unlocked position, and switch adjustable outlet lock 2530 to the unlocked position (see FIG. 26A).

Figure 26A:
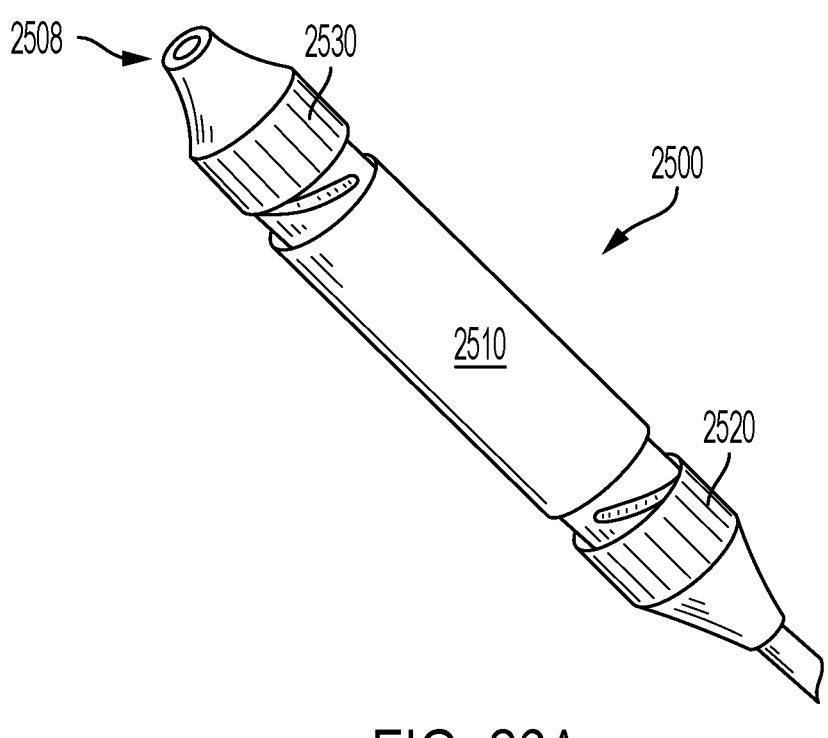
FIGS. 26A-E illustrate various stages of operation of the example fluid-management system of FIG. 25A, according to an example of the present disclosure.
Figure 26B:
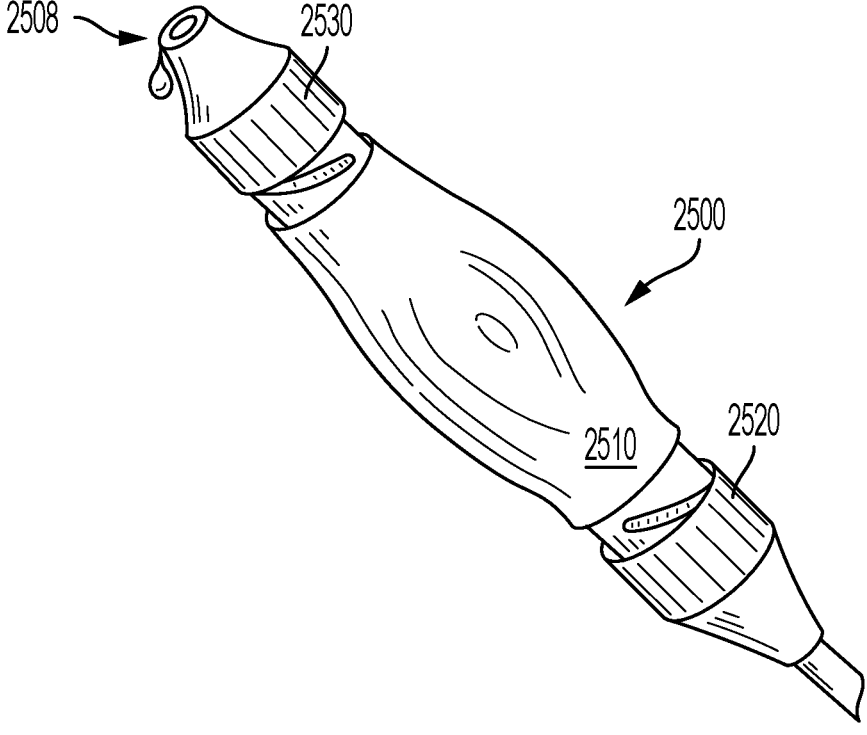
Figure 26C:
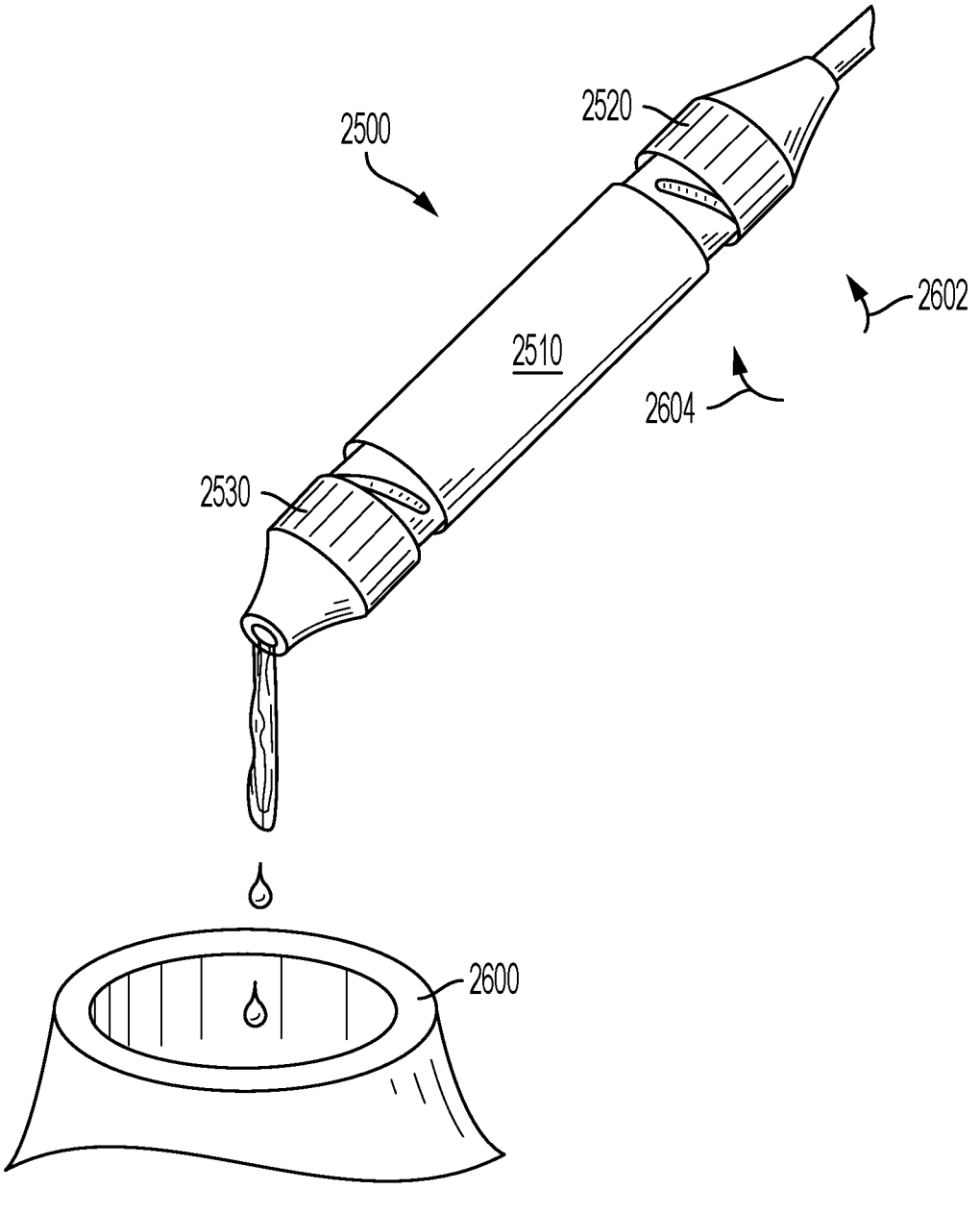

With outlet 2508 pointed upward, adjustable inlet lock 2520 in the unlocked position, and adjustable outlet lock 2530 in the unlocked position, the person may alternately compress and decompress pumping chamber 2510 until pumping chamber 2510 is full or substantially full of fluid (see FIG. 26B compared to FIG. 26A). When pumping chamber 2510 is full or substantially full of fluid, the person may then point outlet 2508 downward and move outlet 2508 below the level of insertion (see FIG. 26C) and/or to a position that is sufficiently low so as to allow a siphoning action to be initiated and fluid to begin to flow. At this level, siphoning flow begins and fluid may be drained into reservoir 2600 (see FIG. 26C). The flow rate may be controlled by adjusting the height of the outlet relative to insertion site and flow may be augmented by manually compressing the pump chamber. Once drainage has stopped, the person may once again alternately compress and decompress pumping chamber 2510 to drain additional fluid from body cavity 2524, if desired. In an example, the length of tube 2522 (and, more particularly, the length of the portion of tube 2522 that is external to the body) may be set to control a vacuum level and/or a maximum vacuum that the siphon produces and/or may produce.

Further, in some examples, the one-way valves, tubing diameter, and/or tubing length can be selected so as to ensure a desired minimum flow rate, such as 25 milliliters per minute (ml/min) or greater, 50 ml/min or greater, 75 ml/min or greater, 100 ml/min, 125 ml/min or greater, 150 ml/min or greater, 175 ml/min or greater, among other possibilities.

As a particular illustrative experimental example, for a valve assembly having a first set of one-way valves and a tube with a 15 mm outer diameter and a 52 mm length, five experimental runs to measure peak pressure and flow rate during syphoning with a given column height (30 cm) were conducted. The peak pressure corresponds to the maximum vacuum that is generated when the pump chamber is maximally compressed and then released. Further, the column height (which was 30 cm in this experiment) is the difference between the fluid level in the chamber and the outlet. A first experimental run resulted in a peak pressure (cm $H_2O$) of −98.8 cm $H_2O$ and a flow rate (ml/min) of 66 ml/min. Further, a second experimental run resulted in a peak pressure of −106.5 and a flow rate of 67 ml/min. Still further, a third experimental run resulted in a peak pressure of −102.7 cm $H_2O$ and a flow rate of 65 ml/min. Yet still further, a fourth experimental run resulted in a peak pressure of −114.1 cm $H_2O$ and a flow rate of 68 ml/min. And yet still further, a fifth experimental run resulted in a peak pressure of −98.7 cm $H_2O$ and a flow rate of 67 ml/min. For this particular illustrative experimental example, the experimental results had a mean of a peak pressure of −104.2 cm $H_2O$ (with a standard deviation of +/−6.4) and a mean flow rate (ml/min) of 66.6 ml/min (with a standard deviation of +/−1.1).

As an additional particular illustrative experimental example, for a valve assembly having a second set of one-way valves (different from the aforementioned first set) and a tube with a 15 mm outer diameter and a 55 mm length, five experimental runs to measure peak pressure and flow rate during syphoning with a given column height (30 cm) were conducted. A first experimental run resulted in a peak pressure of −132.6 cm $H_2O$ and a flow rate (ml/min) of 157.5 ml/min. Further, a second experimental run resulted in a peak pressure of −129.6 and a flow rate of 156.3 ml/min. Still further, a third experimental run resulted in a peak pressure of −133.2 cm $H_2O$ and a flow rate of 155.0 ml/min. Yet still further, a fourth experimental run resulted in a peak pressure of −141.5 cm $H_2O$ and a flow rate of 155.0 ml/min. And yet still further, a fifth experimental run resulted in a peak pressure of −140.8 cm $H_2O$ and a flow rate of 157.5 ml/min. For this additional particular illustrative experimental example, the experimental results had a mean of a peak pressure of −133.5 cm $H_2O$ (with a standard deviation of +/−5.3) and a mean flow rate (ml/min) of 156.3 ml/min (with a standard deviation of +/−1.25).

Other example peak pressures and flow rate are possible as well.

Figure 26D:
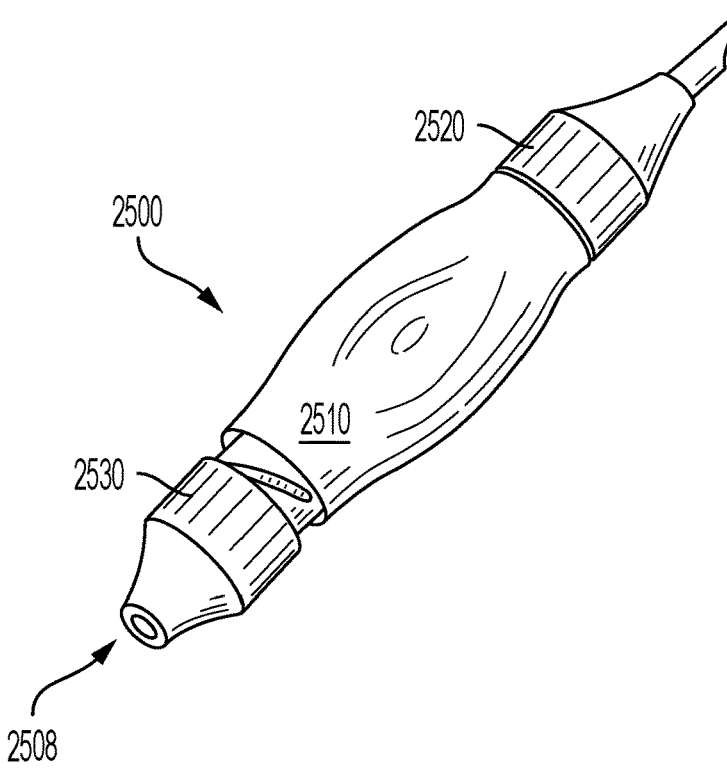

Once desired drainage is complete, the person may move adjustable inlet lock 2520 to the locked position, thereby isolating tube 2522 and body cavity 2524 (see FIG. 26D). Pumping chamber 2510 may then be compressed, thereby emptying the pumping chamber 2510 and placing it under vacuum as the resilient pumping chamber 2510 attempts to recoil and outlet one-way valve 2516 closes. Finally, the person may clean or decontaminate outlet 2508 (clean with soap and water and/or decontaminate with alcohol, betadine, or chlorhexidine, among other possibilities).

Figure 26E:
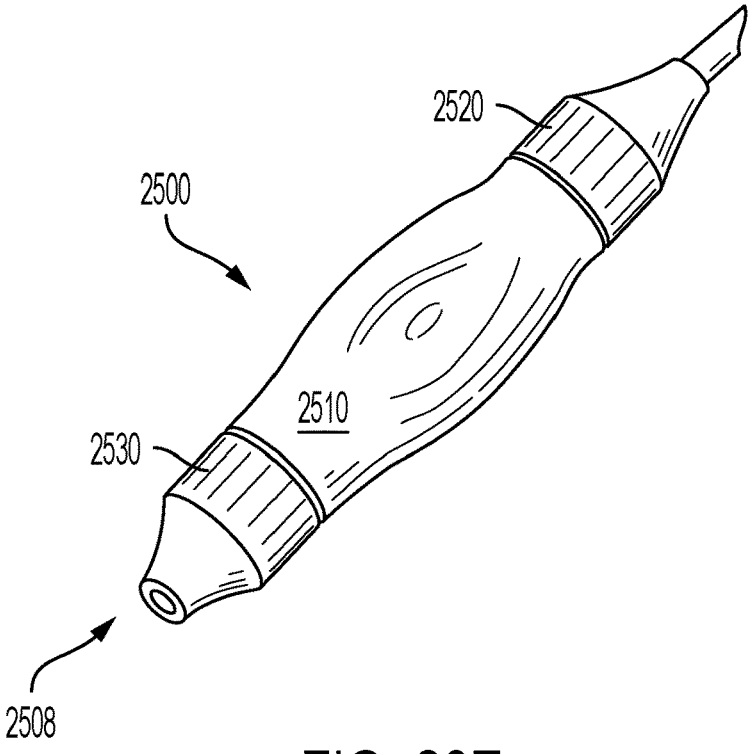

Once outlet 2508 has been cleaned or decontaminated, the person may move adjustable outlet lock 2530 to the locked position (see FIG. 26E). In this configuration, not only is pumping chamber 2510 protected against backflow from the exterior by outlet one-way valve 2516, but also by the bidirectional blockade provided the locked adjustable outlet lock 2530. Similarly, not only is tube 2522 in fluid communication with body cavity 2524 protected against backflow by first one-way valve 2512, but tube 2522 is also protected against backflow the bidirectional blockade provided by the locked adjustable inlet lock 2520. Additionally, the closed adjustable inlet lock 2520 and the closed adjustable outlet lock 2530 isolate the interior of pumping chamber 2510 from the exterior and body cavity 2524, provide bidirectional barriers between the exterior and body cavity 2524, and lastly provide redundant backflow prevention.

In the example of FIGS. 25A-D, adjustable inlet lock 2520 is illustrated as a twist lock configured to pinch tube 2522 and/or inlet 2506. For instance, FIGS. 25A-B illustrate adjustable inlet lock 2520 in the closed positioned (e.g., in which the twist lock pinches tube 2522 positioned at inlet 2506), and FIGS. 21C and 26A-C illustrate adjustable inlet lock 2520 after it has been rotated in direction 2602 to be in the open position (e.g., in which the twist cap no longer pinches tube 2522 at inlet 2506). The rotation may cause the twist lock to move from the closed position to the open position. Further, rotation in the opposite direction 2604 moves adjustable inlet lock 2520 from the open position to the closed position. The twist lock/adjustable inlet lock 2520 of FIGS. 25A-D functions in a manner similar to the twist cap described with reference to FIGS. 8A-D (e.g., twist lock configured to activate pinch arms to pinch tube 2522 at inlet 2506) and thus is not described in as great of detail.

Although in the example of FIGS. 25A-D, adjustable inlet lock 2520 takes the form of a twist lock, various adjustable inlet locks 2520 are possible. For instance, adjustable inlet lock 2520 may take the form of a twist pinch, a pinch level, and an offset device (e.g., forms similar to the forms of the outlet locks illustrated in FIGS. 6A-B, 7A-B, 9A-C, and 10A-B), among other possibilities.

Similarly, in the example of FIGS. 25A-D, adjustable outlet lock 2530 is illustrated as a twist lock configured to pinch outlet 2508 and/or a tube in fluid communication with outlet 2508. For instance, FIGS. 25A-B illustrate adjustable outlet lock 2530 in the closed positioned (e.g., in which the twist lock pinches a tube in fluid communication with outlet 2508, and FIGS. 25C and 26A-D illustrate adjustable outlet lock 2530 after it has been rotated in direction 2602 to be in the open position (e.g., in which the twist lock no longer pinches the tube in fluid communication with outlet 2508). The rotation may cause the twist lock to move from the closed position to the open position. Further, rotation in the opposite direction 2604 moves the twist lock from the open position to the closed position. The twist lock/adjustable outlet lock 2530 of FIGS. 25A-D functions in a manner similar to the twist cap described with reference to FIGS. 8A-D (e.g., twist lock configured to activate pinch arms to pinch outlet 2508 and/or a tube in fluid communication with outlet 2508) and thus is not described in as great of detail.

Although in the example of FIGS. 25A-D, adjustable outlet lock 2530 takes the form of a twist lock, various adjustable outlet locks 2530 are possible. For instance, adjustable outlet lock 2530 may take the form of a twist pinch, a pinch level, and an offset device (e.g., forms similar to the forms of the outlet locks illustrated in FIGS. 6A-B, 7A-B, 9A-C, and 10A-B), among other possibilities.

In some examples, adjustable inlet lock 2520 and adjustable outlet lock 2530 are configured such that each may be grabbed by a user and twisted at the same time, so that both adjustable locks may be opened in a single phase. For instance, adjustable inlet lock 2520 and adjustable outlet lock 2530 may have the same right-hand thread or same left-hand thread such that both may be twisted open at the same time in a single phase, rather than requiring a user to open the locks sequentially in two different phases. Such a single-phase opening process may be useful, for instance, for users that suffer from dexterity issues.

As mentioned above, each of first one-way valve 2512 and second one-way valve 2516 is configured to open and close based on compression and decompression of pumping chamber 2510. In some examples, each of first one-way valve 2512 and second one-way valve 2516 is further configured to open and close based on fluctuations in pressure between the person's body cavity 2524 and the one-way valve that occur based on respiratory action of a breathing cycle of the person. For instance, in some examples, first one-way valve 2512 and second one-way valve 2516 are configured in the manner described above with respect to one-way valves 110, 110' and 110". It should be understood that any of the possibilities and permutations described with respect to one-way valves 110, 110' and 110" are also possible with respect to first one-way valve 2512 and second one-way valve 2516.

In some examples, the pumping chamber 2110 of fluid-management system 2100, the pumping chamber 2510 of fluid-management system 2500, and/or the pumping chamber 402 of fluid-management system 100' are each configured to provide the ability to recoil at a given pressure. In this regard, the thickness of the body of the pumping chamber may affect the recoil pressure provided by the pumping chamber. For instance, as an illustrative example, a pumping chamber formed of silicon and having a half inch internal diameter and a ⅝-inch external diameter may provide a recoil pressure of approximately −100 cmH₂O. However, in another example, a pumping chamber formed of silicon and having thicker walls may provide a greater recoil pressure. For instance, in an example, a pumping chamber formed of silicon and having a half inch internal diameter and a $\frac{7}{8}$-inch external diameter will provide a greater recoil pressure than the recoil pressure provided by the pumping chamber formed of silicon and having a half inch diameter and a $\frac{5}{8}$-inch external diameter. Further, the shape of the pumping chamber may also affect the recoil pressure provided by the pumping chamber. For instance, in an example, a pumping chamber with first shape (e.g., oval) and a given wall thickness will recoil with a different pressure than a pumping chamber with a second, different shape (e.g., tubular) and the same given wall thickness. Other examples are possible as well.

In an example, the pumping chamber of the disclosed fluid-management system is configured to have a given maximum recoil pressure. Various maximum recoil pressures are possible. For instance, in an example, the maximum recoil pressure can range anywhere from about $-300$ $cmH_2O$ to about $-50$ cm $cmH_2O$, and as specific examples, the maximum recoil pressure could be about $-300$ $cmH_2O$, $-275$ $cmH_2O$, $-250$ $cmH_2O$, $-225$ $cmH_2O$, $-200$ $cmH_2O$, about $-175$ $cmH_2O$, about $-150$ $cmH_2O$, about $-125$ $cmH_2O$, about $-100$ $cmH_2O$, about $-75$ $cmH_2O$, or about $-50$ $cmH_2O$, among other possibilities.

Within examples, the maximum recoil pressure for a pumping chamber may be tuned based on the shape and/or thickness of the pumping chamber. More particularly, the shape and/or thickness of the pumping chamber may be selected based on a desired maximum recoil pressure for the pumping chamber.

In an example, the valve assembly may include a compression limiter configured to limit the amount of compression that is possible. In such a case, if the pumping chamber is compressed completely to the compression limiter, then it can recoil fully and generate a maximum suction. For instance, the pumping chamber may comprise sections of localized thickening of the pumping chamber wall that are positioned opposite one another, such that when the pumping chamber is compressed, these thickened areas come together to meet, prevent further compression, and limit the amount of pump chamber volume change that occurs with compression. In another example, the compression limiter include one or more ridges and/or one or more protrusions attached to the pumping chamber wall(s) that limit compression. Other compression limiters are possible as well.

Providing a given maximum recoil pressure may be beneficial for a variety of reasons. As one example, having given maximum recoil pressure may be desirable so as to maintain comfort for users that use the fluid-management system. In practice, a recoil pressure that is too high may be uncomfortable for users, so a given maximum recoil pressure may be selected so as to maintain and/or ensure a comfortable operation for the user. As another example, having given maximum recoil pressure may be desirable so as to provide the ability to provide a large enough recoil pressure that is effective to re-expand a user's lung in the event that a user has a trapped lung. Trapped lung syndrome refers to a condition in which the lung does not fully expand during pleural drainage to oppose the chest wall. Typically, for lungs in which there is fluid in the chest and the fluid is drained, a normal, healthy lung will expand and fill that space. Further, even the majority of distressed lungs will expand and fill that space back up after draining. However, some lungs may have a thickened surface and/or have been collapsed and/or altered long enough that, when the fluid is drained from that space, the lung does not expand fill that space back up after draining. Therefore, the maximum recoil pressure may be selected so as to provide a large enough recoil pressure that is effective to help re-expand a user's lung in the event that a user has a trapped lung (e.g., a selected maximum recoil pressure between $-1000$ and $-200$ $cmH_2O$, among other possibilities). As yet another example, having given maximum recoil pressure may help to overcome catheter occlusion. A given maximum recoil pressure may be beneficial for other reasons as well.

Figure 27:
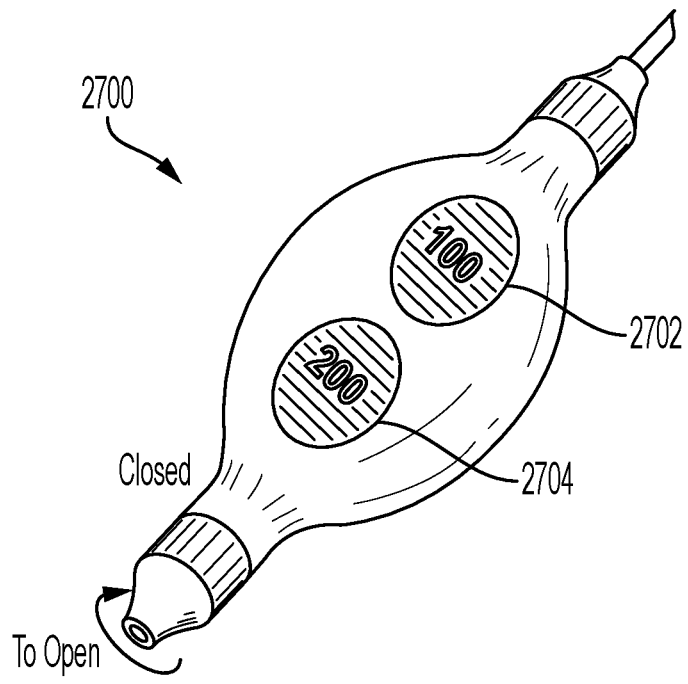
FIG. 27 illustrates an example pumping chamber, according to an example of the present disclosure.

Further, in some examples, the pumping chamber 2110 of fluid-management system 2100, the pumping chamber 2510 of fluid-management system 2500, and/or the pumping chamber 402 of fluid-management system 100' are each configured to provide the ability to recoil at a plurality of different pressures. For instance, the body of the pumping chamber may be shaped and/or sized to recoil at a plurality of different pressures. In this regard, as an illustrative example, FIG. 27 illustrates a pumping chamber 2700 configured to provide the ability to recoil at two different pressures. In particular, pumping chamber 2700 includes a first portion 2702 configured to be compressed and to recoil with a first pressure (illustrated as $-200$ $cmH_2O$ in this example) and a second portion 2704 configured to be compressed and to recoil with a second pressure (illustrated as $-100$ $cmH_2O$ in this example). In order to provide the ability to recoil at different pressures, the thickness of first portion 2702 may be different than the thickness of second portion 2704.

Figures 28A, 28B:
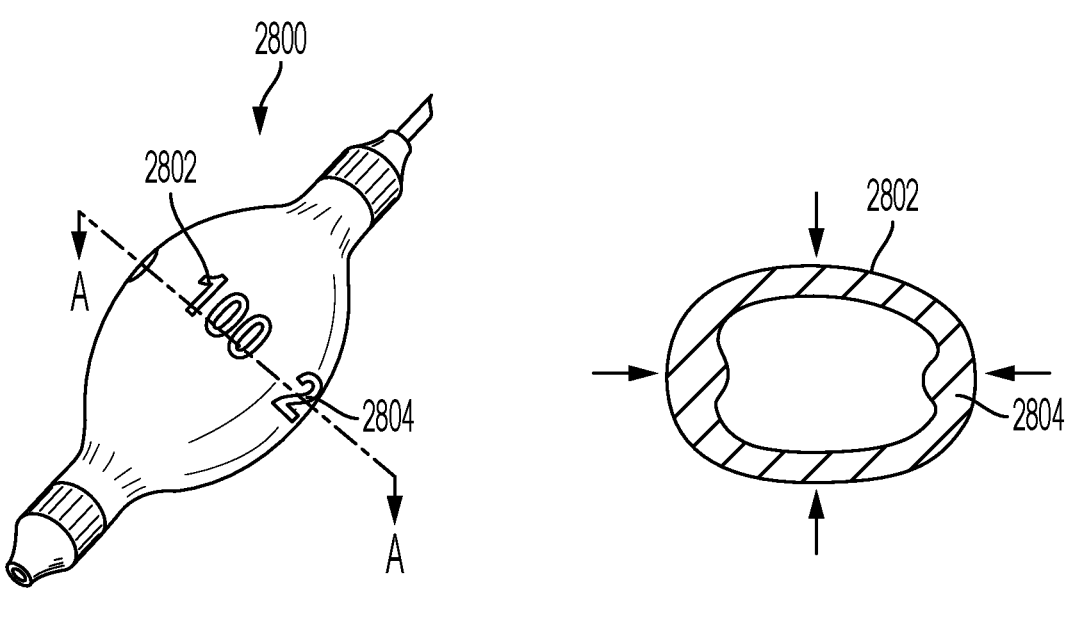
FIG. 28A illustrates an example pumping chamber, according to an example of the present disclosure.
FIG. 28B illustrates a cross-sectional view of the example pumping chamber of FIG. 28A taken along line A-A, according to an example of the present disclosure.

As another illustrative example, FIG. 28a illustrates a pumping chamber 2800 configured to provide the ability to recoil at two different pressures. In particular, pumping chamber 2800 includes a first portion 2802 configured to be compressed and to recoil with a first pressure (illustrated as $-20$ $cmH_2O$ in this example) and a second portion 2804 configured to be compressed and to recoil with a second pressure (illustrated as $-30$ $cmH_2O$ in this example). In this example, the first portion 2802 is a first set of walls of pumping chamber 2800 (e.g., the walls positioned at 0 degrees and 180 degrees relative to an axis of the pumping chamber), whereas second portion 2804 is a second set of walls of pumping chamber 2800 (e.g., the walls positioned at 90 degrees and 270 degrees relative to the axis of the pumping chamber). A user may, for example, use their fingers to compress pumping chamber 2800 at the set of walls that correspond to the desired recoil pressure for the user. In order to provide the ability to recoil at different pressures, the thickness of first portion 2802 may be different than the thickness of second portion 2804. For instance, with reference to FIG. 28B (which is a cross-section of the body of the pumping chamber taken along line A-A of FIG. 28A), the body of pumping chamber 2800 is configured such that the thickness of second portion 2804 is greater than the thickness of first portion 2802. Other examples are possible as well.

Within examples, the plurality of different recoil pressures for a pumping chamber may be tuned based on the shape and/or thickness of the pumping chamber. More particularly, the shape and/or thickness of the pumping chamber may be selected based on the desired plurality of different recoil pressures for the pumping chamber.

Additionally or alternatively, within examples, the plurality of different recoil pressures for a pumping chamber may be provided by a plurality of compression limiters. For instance, the valve assembly may include (i) a first compression limiter for a first portion of the pumping chamber such that the valve assembly is configured to, after compression of the first portion, generate a first suction pressure and (ii) a second compression limiter for a second portion of the pumping chamber such that the valve assembly is configured to, after compression of the second portion, generate a second suction pressure. In such a case, (i) if the pumping chamber is compressed at a first portion of the pumping chamber to the first compression limiter, then it can recoil and generate a first suction, and (ii) if the pumping chamber is compressed at the second portion to the second compression limiter, then it can recoil and generate a second, different suction.

Figure 45A:
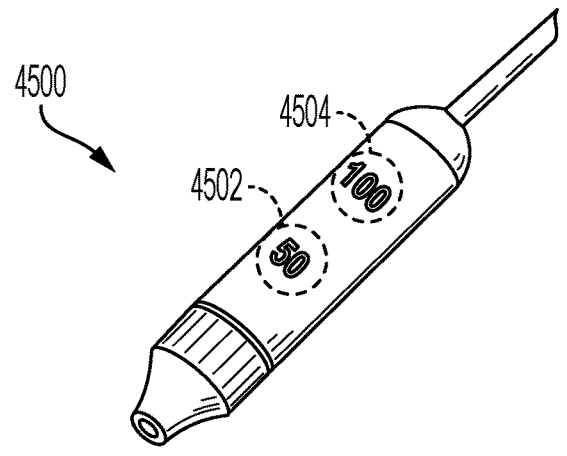
FIG. 45A illustrates an example pumping chamber, according to an example of the present disclosure.
Figure 45B:
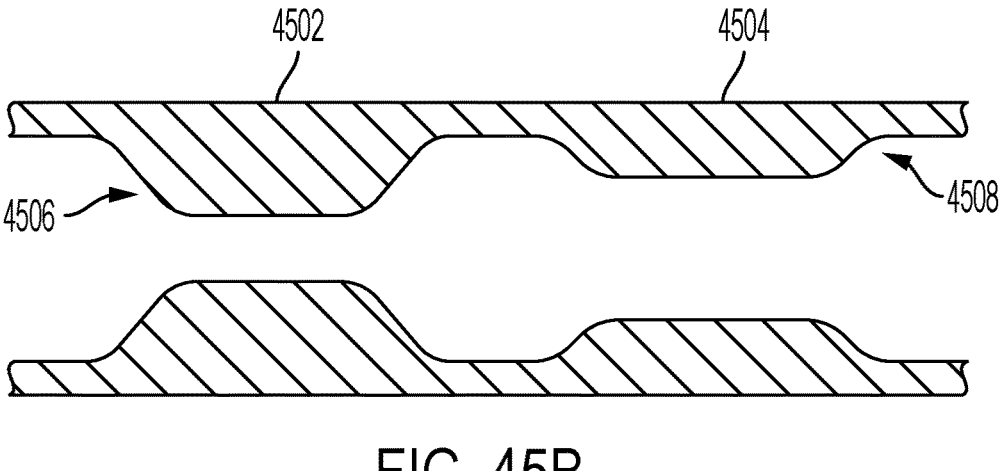
FIG. 45B illustrates a cross-sectional view of a portion of the example pumping chamber of FIG. 45A, according to an example of the present disclosure.
Figure 45C:
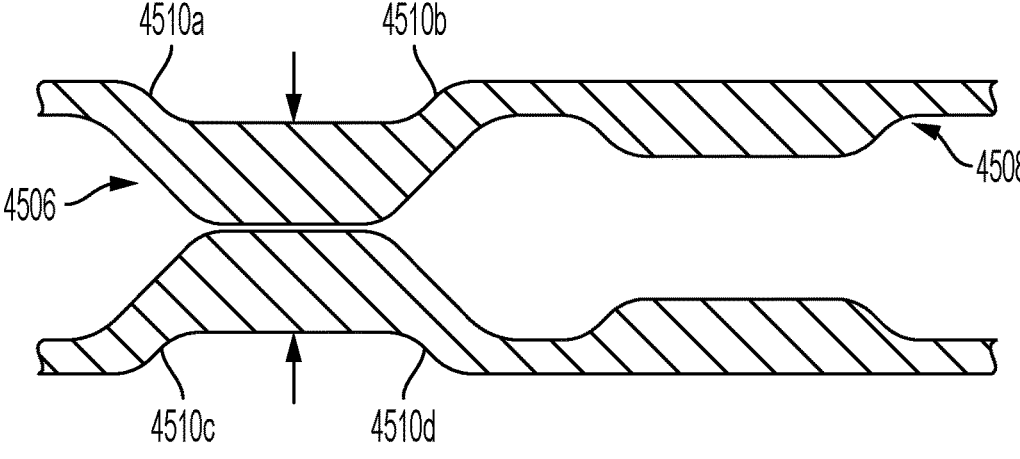
FIG. 45C illustrates a cross-sectional view of a portion of the example pumping chamber of FIG. 45A when a portion of the pumping chamber is compressed, according to an example of the present disclosure.

As an illustrative example, FIG. 45a illustrates a pumping chamber 4500 configured to provide the ability to recoil at two different pressures. In particular, pumping chamber 4500 includes a first portion 4502 configured to be compressed and to recoil with a first pressure (illustrated as −50 cmH₂O in this example) and a second portion 4504 configured to be compressed and to recoil with a second pressure (illustrated as −100 cmH₂O in this example). In this example, with reference to FIG. 45b, the pumping chamber 4500 includes a first compression limiter 4506 for the first portion 4502 and a second compression limiter 4508 for the second portion 4504. First compression limiter 4506 comprises thickened wall sections of a first thickness, and second compression limiter 4508 includes thickened wall sections of a second thickness. With reference to FIG. 45c, when first portion 4502 is compressed, the thickened wall sections of compression limiter 4506 come together to meet and prevent further compression. When portion 4502 is released, pumping chamber wall portions 4510a-d provide recoil force. On the other hand, if second portion 4504 were compressed rather than first portion 4502, the compression limiter 4508 would allow for more deformation than compression limiter 4506. Therefore, if second portion 4506 is compressed, the recoil sections would be more deformed and recoil more, thereby providing a higher recoil pressure.

Providing a plurality of different recoil pressures may be beneficial for a variety of reasons. As one example, it may be desirable to have a plurality of different recoil pressures to account for user preference (e.g., user preferences related to preferred pump speed and/or different comfort levels or pain-tolerance levels of the user of the fluid-management system). For instance, providing a plurality of different recoil pressures from which the user can select a given recoil pressure during operation of the fluid-management system may allow the user to select a recoil pressure based on desired pump speed for the user and/or comfort level or pain-tolerance level of the user.

As another example, plurality of recoil pressures may be useful for a situation in which a user may have a trapped lung. For instance, in an example, the pumping chamber may provide three levels of vacuum, which in this example may be a low vacuum (e.g., a recoil pressure in a range of −20 to −50 cm cmH₂O), medium vacuum (e.g., a recoil pressure in a range of −75 to −200 cm cmH₂O), and a high vacuum (e.g., a recoil pressure in a range of −200 to −250 cm cmH₂O). As mentioned above, a higher vacuum pressure may cause more discomfort to a user compared to a lower vacuum pressure. Therefore, a user may initially select the low vacuum for comfort level or pain-tolerance level of the user. However, if the low vacuum is insufficient to cause or help the trapped lung to re-expand, a user may pump the pumping chamber to generate the medium vacuum, so as to attempt to re-expand the trapped lung. Further, if the medium vacuum is insufficient to cause or help the trapped lung to re-expand, a user may pump the pumping chamber to generate the high vacuum, so as to attempt to re-expand the trapped lung. A plurality of recoil pressures may be beneficial for other reasons as well.

Figure 29B:
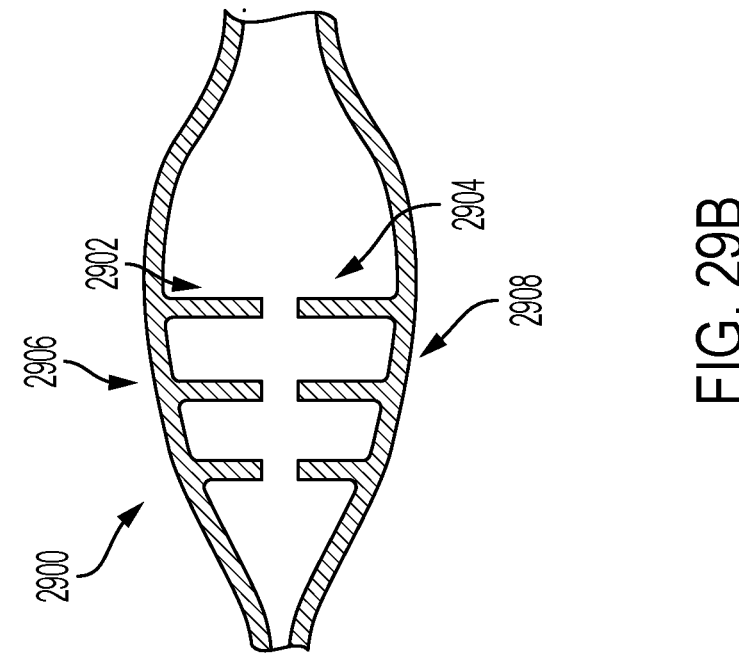
FIG. 29B illustrates a cross-sectional view of the example pumping chamber of FIG. 29A taken along line B-B, according to an example of the present disclosure.
Figure 29A:
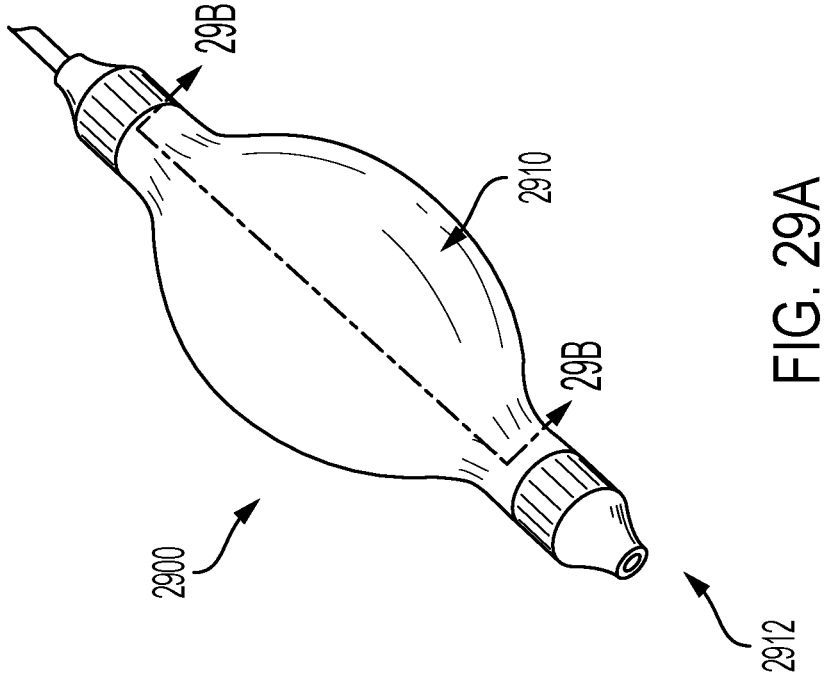
FIG. 29A illustrates an example pumping chamber, according to an example of the present disclosure.

In some examples, the pumping chamber 2110 of fluid-management system 2100, the pumping chamber 2510 of fluid-management system 2500, and/or the pumping chamber 402 of fluid-management system 100' are each configured to provide the ability to cut or break-up fibrous strands during compression of the pumping chamber. In this regard, FIGS. 29A-B illustrate a pumping chamber 2900 that includes a plurality of first protrusions 2902 and a plurality of second protrusions 2904. FIG. 29B illustrates a partial cross-sectional view of pumping chamber 2900 taken along line B-B. The first protrusions 2902 are disposed on a first portion 2906 (e.g., a first inner wall) of a body 2910 of the pumping chamber 2900 that is opposite a second portion 2908 (e.g., a second inner wall) of body 2910 on which the second protrusions 2904 are disposed. The plurality of first protrusions 2902 is configured to interweave with the plurality of second protrusions during compression of the pumping chamber. By interweaving with one another during compression, the pluralities of protrusions may cut or break-up fibrous strands during compression of the pumping chamber 2900, potentially allowing them to pass more readily through the fluid-management system (and, more particularly, through pumping chamber 2900 and out outlet 2912).

In some examples, fluid-management system 2100, fluid-management system 2500, and/or fluid-management system 100' are each configured to provide access to the pumping chamber, the inlet of the valve assembly, and/or the tube of the fluid-management system. Further, in some examples, fluid-management system 100 may be configured to provide access to the inlet of the valve assembly and/or the tube of the fluid-management system.

Access to the pumping chamber, the inlet of the valve assembly, and/or the tube of the fluid-management system may be beneficial for a variety of reasons. For instance, with respect to the pumping chamber, access to the pumping chamber may be desirable to access the pumping chamber and/or the one-way valves within the pumping chamber. In an example, access to the pumping chamber may be useful for flushing out a clot. As another example, access to the pumping chamber may be useful for obtaining a sample of the material (e.g., obtaining a sample of material if material within the pumping chamber were to clot). Further, with respect to the inlet of the valve assembly and/or the tube of the fluid-management system, access to the inlet of the valve assembly and/or the tube of the fluid-management system may be desirable to deliver therapy through the tube. For instance, access to the inlet and/or tube may be useful for delivering a drug (e.g., a medicine, an antibiotic, a chemotherapy agent, among other possibilities) to the body cavity that is in fluid communication with the tube (e.g., the pleural cavity). As another example, access to the inlet and/or tube may be useful in the event of a clot in one or more of the one way valves (e.g., to inject fluid to flush out the clot). As another example, access to the tube may be useful for obtaining a sample of the material (e.g., obtaining a sample of material if material within the inlet and/or tube were to clot).

To facilitate access to access to the pumping chamber, the inlet of the valve assembly, and/or the tube of the fluid-management system, fluid-management system 2100, fluid-management system 2500, and/or fluid-management system 100' may each be configured to provide access to the pumping chamber, the inlet of the valve assembly, and/or the tube of the fluid-management system. For instance, valve assembly 2104, valve assembly 2504, and/or valve assembly 104' may include one or more of a pumping chamber access port and an inlet access port. Further, fluid-management system 100 may be configured to provide access to the inlet of the valve assembly and/or the tube of the fluid-management system. For instance, valve assembly 104 may include an inlet access port.

In this regard, as an illustrative example of a pumping chamber access port and an inlet access port, FIG. 30 illustrates a valve assembly 3000 that includes a pumping chamber access port 3002 for pumping chamber 3004 and an inlet access port 3006. In some examples, pumping chamber access port 3002 may be configured to provide access to a needle. In other examples, pumping chamber access port 3002 may take the form of a needless access hub or port. Various needless access hubs are possible. As one possibility, the needless access hub may be a needless access port valve that includes a grommet or plug that may be pushed out of the way, so as provide access to the pumping chamber. Other needless access hubs are possible as well.

Similarly, in some examples, inlet access port 3006 may be configured to provide access to a needle. In other examples, inlet access port 3006 may take the form of a needless access hub or port. Various needless access hubs are possible. As one possibility, the needless access hub may be a needless access port valve that includes a grommet or plug that may be pushed out of the way, so as provide access to the tube. Other needless access hubs are possible as well.

In an example, pumping chamber access port 3002 includes a thickened area in a wall of the pumping chamber. The thickened area may be configured to be penetrable by a needle so as to allow access by the needle and to reseal when the needle is removed from the thickened material. In such an example, the pumping chamber access port 3002 may further include a puncture-resistant material in an area in the wall located across from the pumping chamber access port. For instance, with reference to FIG. 31A, pumping chamber access port 3002 includes a thickened area 3102 in a wall 3104 of the pumping chamber 3004, and pumping chamber 3004 further includes a puncture-resistant material 3106 in an area 3108 in wall 3110 located across from pumping chamber access port 3002. Various puncture-resistant materials are possible. For instance, in some examples, the puncture-resistant material may be a hard plastic(s) such as nylon, Teflon, polyethylene terephthalate (PET), and/or polyamide, among other possibilities. In some examples, the puncture-resistant material may be a metal such as nitinol or stainless steel, among other possibilities. Other puncture-resistant materials are possible as well.

In an example, the area in the wall located across from the pumping chamber access port is beneath the pumping chamber access port 3002. The puncture-resistant material may prevent or limit potential damage to the body of the pumping chamber 3004 by a needle or other device that may be inserted into pumping chamber access port 3002. Further, in an example, pumping chamber access port 3002 is positioned a threshold distance away from the inlet one-way valve within pumping chamber 3004 (e.g., 2 mm or more), as well as a threshold distance (e.g., 2 mm or more) away from the outlet one-way valve within pumping chamber 3004. In some examples, the threshold distance away from the inlet one-way valve within pumping chamber 3004 is 2 mm or more, 5 mm or more, or 7 mm or more, among other possibilities. In some examples, the threshold distance away from the outlet one-way valve within pumping chamber 3004 is 2 mm or more, 5 mm or more, or 7 mm or more, among other possibilities. Positioning pumping chamber access port 3002 in this way may help may prevent or limit potential damage to the one-way valves by a needle or other device that may be inserted into pumping chamber access port 3002.

Turning next to inlet access port 3006, in an example, the inlet access port includes a thickened area in a wall of the valve assembly. The thickened area may be configured to be penetrable by a needle so as to allow access by the needle and to reseal when the needle is removed from the thickened material. Further, in such an example, the valve assembly may further include a puncture-resistant material in an area in the wall located across from the inlet access port. For instance, with reference to FIG. 31B, inlet access port 3006 includes a thickened area 3112 in a wall 3114 of valve assembly 3000, and valve assembly 3000 further includes a puncture-resistant material 3116 in an area 3118 in the wall 3120 located across from the inlet access port 3006.

In an example, the area 3118 in the wall 3120 located across from the inlet access port 3006 is beneath the inlet access port 3006. The puncture-resistant material may prevent or limit potential damage to the body of the valve assembly by a needle or other device that may be inserted into the inlet access port. Further, in an example, the inlet access port is positioned a threshold distance away from the inlet one-way valve and/or the inlet lock (e.g. 2 mm or more. In some examples, the threshold distance away from the inlet one-way valve and/or the inlet lock is 2 mm or more, 5 mm or more, or 7 mm or more, among other possibilities. Positioning the inlet access port the threshold distance away from the inlet one-way valve and/or the inlet lock may help may prevent or limit potential damage to the one-way valve and/or the inlet lock by a needle or other device that may be inserted into the inlet access port.

Figure 32A:
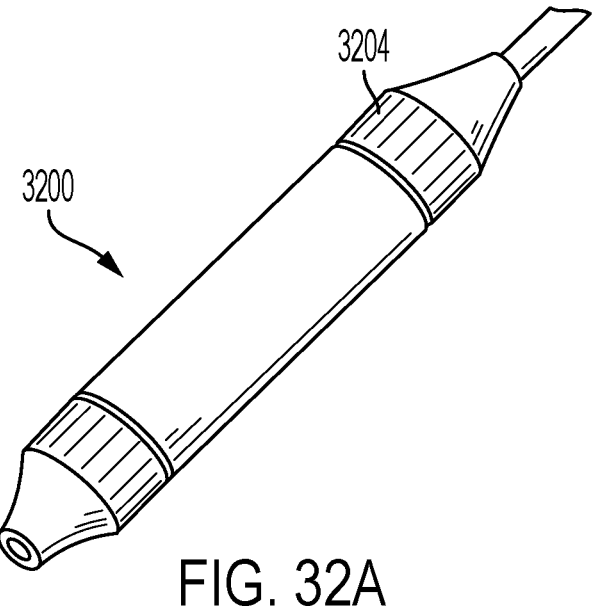
FIG. 32A illustrate an example valve assembly having an inlet access port that is inaccessible and hidden from view when an adjustable inlet lock is in the locked position, according to an example of the present disclosure.
Figure 32B:
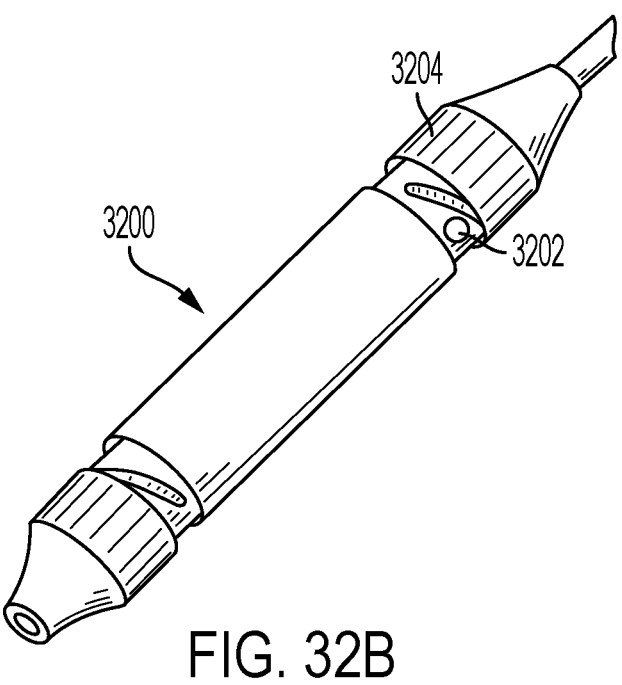
FIG. 32B illustrates the example valve assembly when the adjustable inlet lock is in the unlocked position and the inlet access port is accessible, according to an example of the present disclosure.

In an example, the inlet access port may be configured to be inaccessible and/or hidden from view when the inlet lock is in the locked position. For instance, with respect to FIG. 32A-B, valve assembly 3200 includes an inlet access port 3202 (see FIG. 32B) that is (i) inaccessible and hidden from view when adjustable inlet lock 3204 is in the locked position (see FIG. 32A) and (ii) accessible and visible when adjustable inlet lock 3204 is in the unlocked position (see FIG. 32B). In addition to providing aesthetic advantages, having an inlet access port configured to be inaccessible and/or hidden from view when the inlet lock is in the locked position beneficially provides an additional layer of protection, as the inlet access port is only accessible when the adjustable inlet lock is in the unlocked position.

Figures 40, 41:
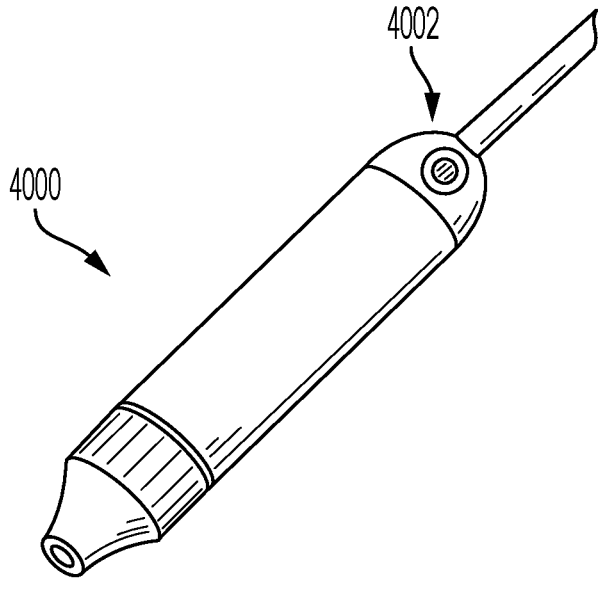
FIG. 40 illustrates an example valve assembly, according to an example of the present disclosure.
FIG. 41 illustrates an example adjustable tube lock, according to an example of the present disclosure.

As mentioned above, valve assembly 2104, valve assembly 2504, and/or valve assembly 104' may include one or more of a pumping chamber access port and an inlet access port. Thus, in some examples, valve assembly 2104, valve assembly 2504, and/or valve assembly 104' may include a pumping chamber access port and not an inlet access port. In other examples, valve assembly 2104, valve assembly 2504, and/or valve assembly 104' may include an inlet access port and not a pumping chamber access port. In this regard, as an illustrative example of a valve assembly with an inlet access port and not a pumping chamber access port, FIG. 40 illustrates a valve assembly 4000 that includes an inlet access port 4002 but not a pumping chamber access port.

In some examples, fluid-management system 2100, fluid-management system 2500, fluid-management system 100', and fluid-management system 100 may each further include a tube lock that is configured to lock the tube at a point that is external to the person's body and upstream of the valve assembly. As mentioned above, the fluid-management systems may include a pumping chamber access port and/or an inlet access port that allow access for, e.g., flushing out one or more components of the fluid-management system. Such a tube lock may be configured to lock or clamp off the tube, which may be beneficial during flushing of the pumping chamber and/or the one-way valve(s). For instance, with reference to FIG. 30, valve assembly 3000 may further include an adjustable tube lock 3022. Adjustable tube lock 3022 may be activated in various ways so as to pinch tube 3024, thereby clamping the tube.

Various adjustable tube locks are possible. In this regard, the adjustable tube lock 3022 of FIG. 30 functions in a manner similar to the twist pinch described with reference to FIGS. 7A-B and thus is not described in as great of detail. However, adjustable tube lock 3022 may take various other forms. For instance, adjustable tube lock 3022 may take the form of a twist pinch, a pinch level, and an offset device (e.g., forms similar to the forms of the outlet locks illustrated in FIGS. 6A-B, 7A-B, 9A-C, and 10A-B), among other possibilities. Further, in some examples, adjustable tube lock 3022 is non-removably attached to tube 3024.

Still further, in some examples, adjustable tube lock 3022 is removable. In this regard, as an illustrative example of an adjustable tube lock that is removable, FIG. 41 illustrates an adjustable tube lock 4100 that takes the form of a clamp that can be placed on the tube and removed from the tube as desired. For a valve assembly with an outlet lock and not an inlet lock (e.g., valve assembly 4000 shown in FIG. 40), adjustable tube lock 4100 could be placed on the tube between the pumping chamber and the person's body. When the adjustable tube lock 4100 is not placed on the tube, the access port may communicate with the body cavity (e.g., pleural space). On the other hand, when the adjustable tube lock 4100 on the tube and clamps the tube at a point between the pumping chamber and the person's body, the body cavity is isolated from the access port and pumping chamber. Further, the access port may be in fluid communication with the inlet valve. If there is an occlusion in the pump chamber or one-way valves, pressure could be applied (e.g., with a syringe) to clear the debris or blockage. The access port may be a luer lock with a removable cup or a self-sealing needless access port.

As mentioned above, adjustable tube lock 3022 may ensure that fluid is not forced back into the body when pump chamber 3004 is flushed out via inlet access port 3006. Rather, adjustable tube lock 3022 will block fluid from flowing upstream in tube 3024 beyond the adjustable tube lock 3022, and instead fluid being used to flush out valve assembly 3000 will flow through the valves and out of the outlet of the fluid-management system.

In some examples, the pumping chamber 2110 of fluid-management system 2100, the pumping chamber 2510 of fluid-management system 2500, and/or the pumping chamber 402 of fluid-management system 100' are each configured such that the distal end of the valve assembly is configured to fit into a variety of different bottles, such as bottles that have openings of different sizes. In an example, the distal end of the valve assembly is tapered such that the distal end of the valve assembly may fit into a plurality of bottle openings of different sizes. Further, in an example, the distal is tapered such that a tip of the valve assembly stays off the walls of the bottle. In this regard, the taper may be symmetrical about an axis of the valve assembly.

As an illustrative example, with reference to FIGS. 33A-B, valve assembly 3300 is configured such that distal end 3302 is able to fit into bottle 3304. Distal end 3302 may be tapered such that a tip of valve assembly 3300 stays off the walls of bottle 3304 when it is inserted into the opening of the bottle. The taper be symmetrical about an axis 3306 of valve assembly.

In an example, bottle 3304 may have an externally-threaded opening configured to attached to a screw cap with an internal thread. Such an externally-threaded opening configured to attached to a screw cap are common throughout various industries, including, for instance, the medical and food industry. As one example, soda bottles are commonly provided with such externally-threaded openings.

Furthermore, in an example, when the distal end of the valve assembly is inserted in the bottle, it may be beneficial to have a vent that allows air to flow between the bottle and the valve assembly. In this regard, the pumping chamber may be configured to provide a vent when the valve assembly is positioned to drain into a bottle. The vent may take various forms. As one possibility, the body of the pumping chamber may include a depression, so that when the pump chamber is positioned against the bottle opening, there is an air gap that allows are the flow between the inside of the bottle and the external environment. For instance, with reference to FIGS. 34A-B, pumping chamber 3400 includes a depression 3402 in body 3404. FIG. 34B illustrates a cross sectional view of body 3404 of pumping chamber 3400 taken along line C-C. When pumping chamber 3400 is positioned against a bottle opening, depression 3402 provides an airgap that will allow flow between the inside of the bottle and pumping chamber 3400 to the external environment. Other example vents are possible as well.

Figures 35A, 35B:
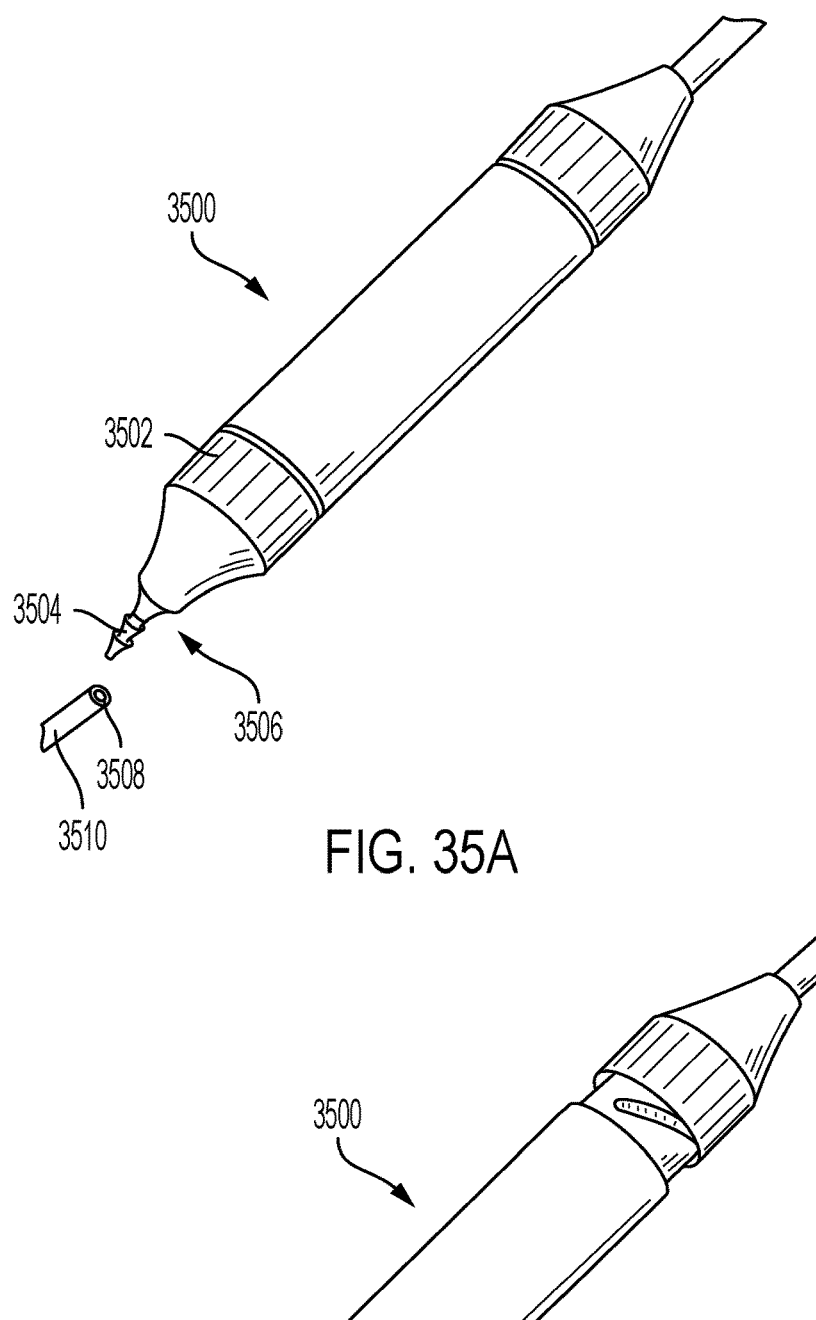
FIG. 35A illustrates an example valve assembly configured to attach to an external tube, according to an example of the present disclosure.
FIG. 35B illustrates the example valve assembly of FIG. 35A attached to an external tube, according to an example of the present disclosure.

In another example, in addition to or alternative to the distal end being configured to fit a bottle, the distal end may be configured to plug into other tubes. As mentioned above with respect to FIG. 17, valve assembly 104' may be configured to connect to an indwelling catheter 1702. Similarly, valve assembly 2104 and valve assembly 2504 may also be configured to connect to another tube such as an external tube. For instance, in an example, the distal end of fluid-management system 2100, the distal end of fluid-management system 2500, the distal end of fluid management system 100, and/or distal end of fluid-management system 100' are each configured to attach to a tube. In this regard, as an illustrative example, FIG. 35 illustrates a valve assembly 3500 that includes (i) an adjustable outlet lock 3502 of the valve assembly 3500 and (ii) an attachment system 3504 on a distal end 3506 of the valve assembly 3500. The attachment system 3504 is configured to attach to a proximal end 3508 of tube 3510. Any suitable attachment system for connecting to proximal end 3508 of tube 3510 is possible. In an example, attachment system 3504 may be configured to provide an interference fit with proximal end 3508 of tube 3510. However, other attachment systems are possible as well. After connecting valve assembly 3500 to tube 3510, a user may control adjustable outlet lock 3502 (e.g., open and close adjustable outlet lock 112) to drain fluid from the body cavity and out a distal end (not shown) of tube 3510 as desired. In an example, by being able to connect to an external tube such as tube 3510, a user (e.g., the patient or an individual assisting the patient) may use the tube to drain into a reservoir that is not directly proximate to valve assembly 3500. In other words, the ability to connect to an external tube may extend the reach of the fluid management system, if desired. In an example, this ability to connect to an external tube could allow the fluid management system to perform as a continuous drain thoracostomy tube should the need arise for continuous drainage (e.g., such as when the patient may be admitted to a hospital and/or intensive care unit (ICU)).

Figure 42A:
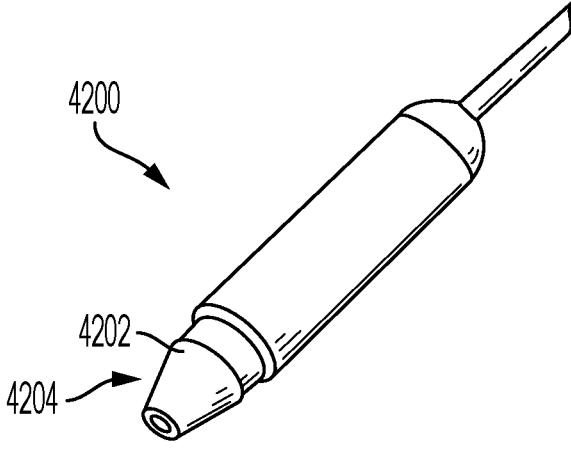
FIG. 42A illustrates an example valve assembly having an adjustable outlet lock in a closed position, according to an example of the present disclosure.
Figure 42B:
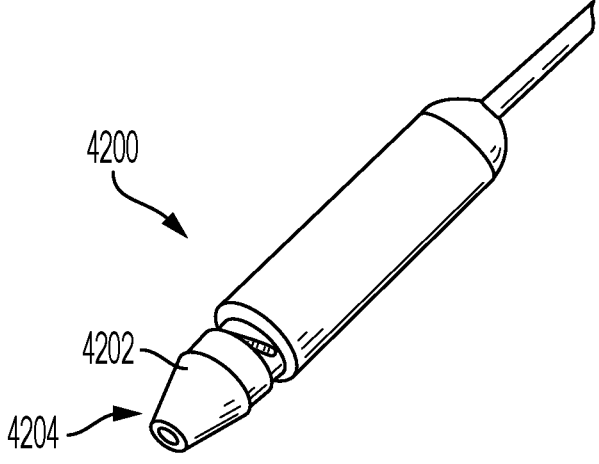
FIG. 42B illustrates the example valve assembly of FIG. 42A with the adjustable outlet lock in an open position, according to an example of the present disclosure.

Other attachment systems for attaching to a tube are possible as well. As another illustrative example, FIGS. 42A-B illustrate a valve assembly 4200 that includes an adjustable outlet lock 4202 of the valve assembly 4200. FIG. 42A illustrates adjustable outlet lock 4202 in the closed position, and FIG. 42B illustrates adjustable outlet lock 4202 in the open position. Adjustable outlet lock 4202 has a taper 4204 that could plug into a chest tube drain or suction tubing.

Figure 43A:
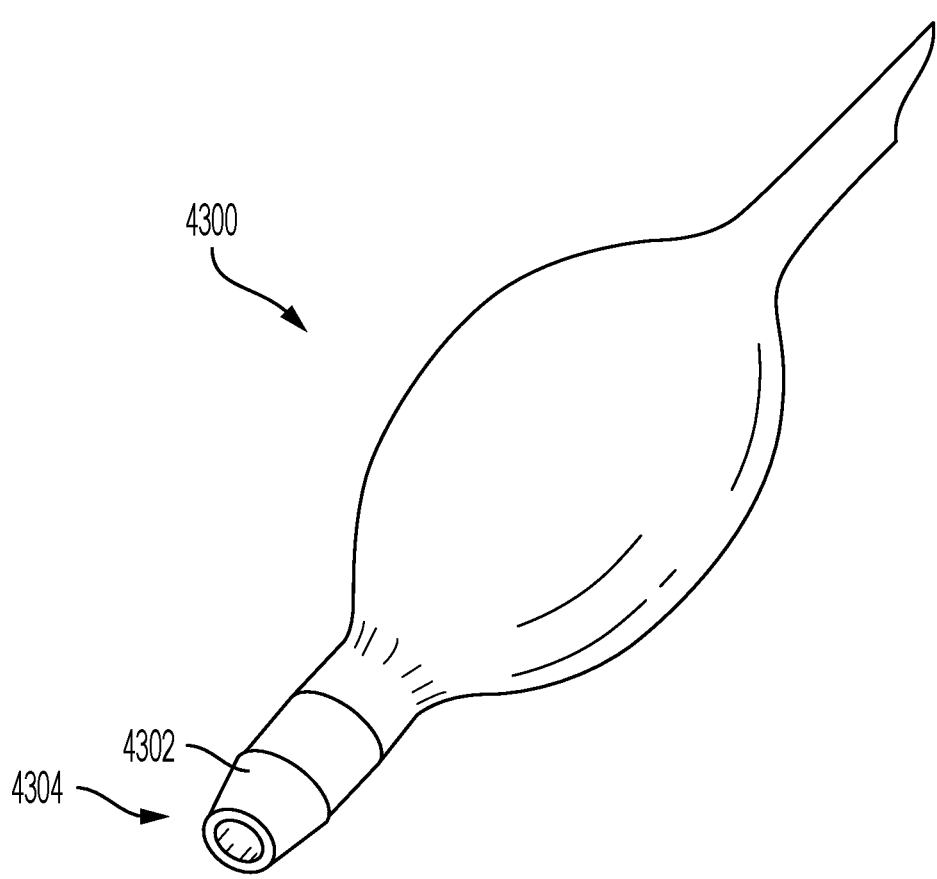
FIG. 43A illustrates an example valve assembly having an adjustable outlet lock in a closed position, according to an example of the present disclosure.
Figure 43B:
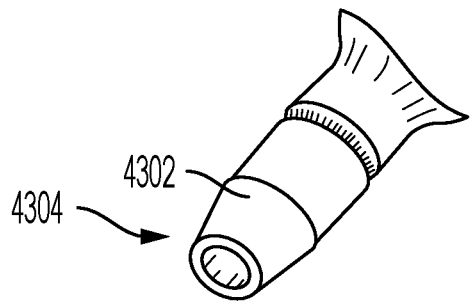
FIG. 43B illustrates the example adjustable outlet lock of FIG. 43A in an open position, according to an example of the present disclosure.

As yet another illustrative example, FIGS. 43A-B illustrate a valve assembly 4300 that includes an adjustable outlet lock 4302 of the valve assembly 4300. FIG. 43A illustrates adjustable outlet lock 4302 in the closed position, and FIG. 43B illustrates adjustable outlet lock 4302 in the open position. Adjustable outlet lock 4302 has a taper 4304 that could plug into a chest tube drain or suction tubing. Further, compared to adjustable outlet lock 4202 of FIGS. 42A-B, adjustable outlet lock 4302 has a flat area that could provide additional space for gripping the adjustable outlet lock in order to rotate and unlock the outlet lock.

Figure 44:
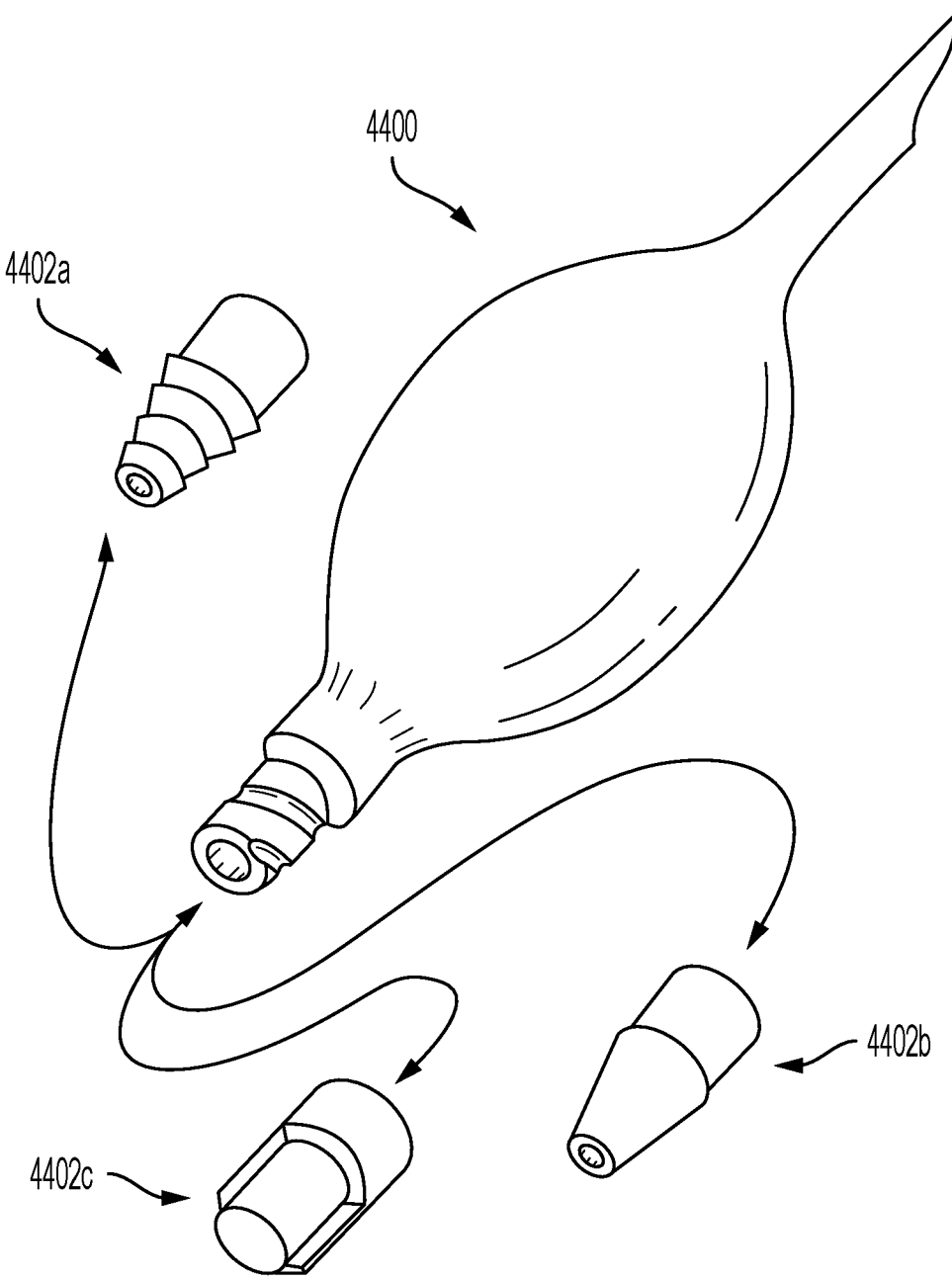
FIG. 44 illustrates an example valve assembly configured to attach to a plurality of adapters, according to an example of the present disclosure.

Further, in some examples, the valve assembly may be configured to attach to a plurality of different adapters and/or caps. For instance, as an illustrative example, FIG. 44 illustrate a valve assembly 4400 that is configured to attach to a plurality of different adapters 4402a and 4402b. Adapter 4402a is an adapter that includes a wide base onto which is mounted a cylinder with progressively smaller external threading (and is commonly referred to as a "Christmas tree adapter") and adapter 4402b is a tapered adapter. In turn, the different adapters may serve a different function such as, for instance, connecting to a different type of tubing. In addition, valve assembly 4400 may also be configured to attach to one or more caps, such as cap 4402c.

As mentioned above, in an example, one-way valve 110 may include a plurality of lips that define a slit that can move from a closed position to an open position. For instance, with reference to FIGS. 2A-B, one-way valve 110 may include first lip 202 and second lip 204 that define slit 206. The lips 202 and 204 may be configured such that, when the lips are in the closed position, the surface area of interaction between the lips is relatively small. For instance, in an example, the surface area of interaction is below 60 mm² and preferably in a range 0.6 mm² to 6 mm².

Figure 36A:
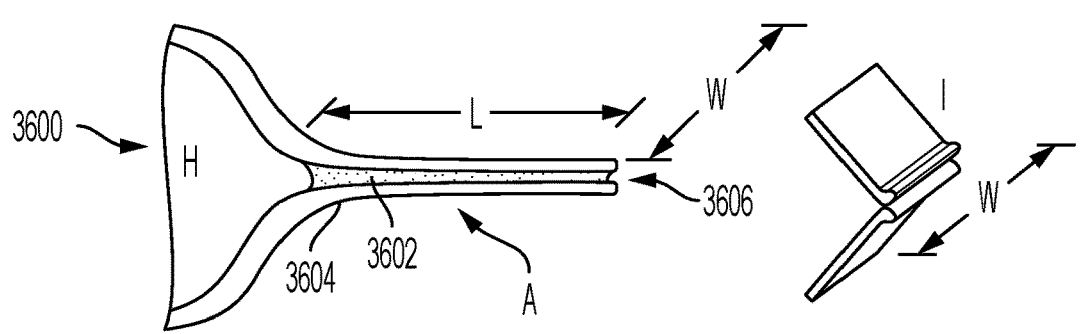
FIG. 36A illustrates an example one-way valve, according to an example of the present disclosure.

Similarly, in some examples, the one-way valves 2112 and 2116 of fluid-management system 2100 and the one-way valves 2512 and 2516 of fluid-management system 2500 each include a plurality of lips that define a slit that can move from a closed position to an open position. For instance, with reference to FIG. 36A, one-way valve 3600 may include first lip 3602 and second lip 3604 that define slit 3606. The lips 3602 and 3604 may be configured such that, when the lips are in the closed position, the surface area of interaction between the lips is relatively small. The surface area of interaction may be the length×width of the lips, as shown in FIG. 36A. Various surface areas of interaction are possible. For instance, in an example, the surface area of interaction may be less than 60 mm², and as specific examples, less than 55 mm², less than 50 mm², less than 45 mm², less than 40 mm², less than 35 mm², less than 30 mm², less than 25 mm², less than 20 mm², less than 15 mm², less than 10 mm², less than 9 mm², less than 8 mm², less than 7 mm², less than 6 mm², less than 5 mm², less than 4 mm², less than 3 mm², less than 2 mm², or less than 1 mm², among other possibilities. Such a surface area of interaction may help ensure that the one-way valve works well both when wet and dry.

Further, in some examples, the surface area of interaction may be greater than 0.6 mm². In some examples, the surface area of interaction may be in a range between 0.6 mm² to 60 mm², in a range between 0.6 mm² to 55 mm², in a range between 0.6 mm² to 50 mm², in a range between 0.6 mm² to 45 mm², in a range between 0.6 mm² to 40 mm², in a range between 0.6 mm² to 35 mm², in a range between 0.6 mm² to 30 mm², in a range between 0.6 mm² to 25 mm², in a range between 0.6 mm² to 20 mm², in a range between 0.6 mm² to 15 mm², in a range between 0.6 mm² to 10 mm², in a range between 0.6 mm² to 9 mm², in a range between 0.6 mm² to 8 mm², in a range between 0.6 mm² to 7 mm², in a range between 0.6 mm² to 6 mm², in a range between 0.6 mm² to 5 mm², in a range between 0.6 mm² to 4 mm², in a range between 0.6 mm² to 3 mm², in a range between 0.6 mm² to 2 mm², or in a range between 0.6 mm² to 1 mm², among other possibilities. Such a surface area of interaction may help ensure that the one-way valve works well both when wet and dry.

Figure 36B:
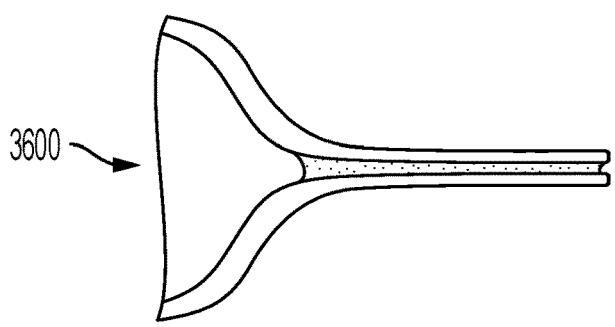
FIG. 36B illustrates the example one-way valve of FIG. 36A in a dry or substantially dry condition, according to an example of the present disclosure.
Figure 36C:
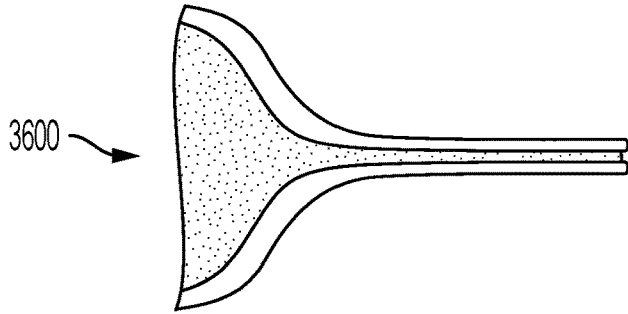
FIG. 36C illustrates the example one-way valve of FIG. 36A in a wet or partially wet condition, according to an example of the present disclosure.
Figure 36D:
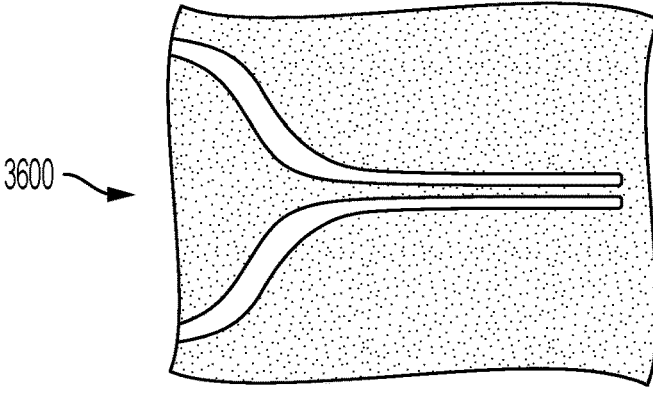
FIG. 36D illustrates the example one-way valve of FIG. 36A in a fully wetted condition, according to an example of the present disclosure.

FIGS. 36B-D illustrate one-way valve 3600 in different conditions. In particular, FIG. 36B illustrates one-way valve 3600 in a dry or substantially dry condition, FIG. 36C illustrates one-way valve 3600 in a wet or partially wet condition, and FIG. 36D illustrates one-way valve 3600 in a fully wetted condition. Such a surface area of interaction may help ensure that the one-way valve works well in these various conditions illustrated in FIGS. 36B-D.

In some examples, in order to prevent blocking or clogging of the disclosed fluid-management systems 2100 and 2500, one or more components of the fluid-management systems may be coated in anticoagulation factors or fibrinolytic factors. For example, the components or surfaces (e.g., internal and/or external surfaces) of valve assemblies 2104, 2504 and/or implanted tube 2122, 2522 may be coated at least in part with anticoagulation factors or fibrinolytic factors. For instance, with reference to FIGS. 21A-D, internal portions and/or external portions of the body of pumping chamber 2110, one-way valves 2112, 2116, and/or internal portions of tube 2122 may be coated in anticoagulation factors or fibrinolytic factors. Further, with reference to FIGS. 25A-D, internal and/or external portions of pumping chamber 2510, one-way valves 2512, 2516, and/or internal portions of tube 2522 may be coated in anticoagulation factors or fibrinolytic factors. Other components may be coated with anticoagulation factors or fibrinolytic factors as well.

As mentioned above, the presence of the anticoagulation factors may reduce the amount of clotting that would otherwise occur if they were not present. Further, examples of anticoagulation factors include heparin, low molecular weight heparin, fondaparinux, idraparinux, idrabiotaparinux, diabigatran, rivaroxaban, apixan, betrixaban, edoxaban, darexaban, letaxaban, eribaxaban, hirudin, lepirudin, bivalirudin, argatroban, dabigatran, ximelagatran, hementin, vitamin E, coumarin, warfarin, acenocoumarol, phenprocoumon, atromentin, phenindione, brodifacoum, and difenacoum. Examples of fibrinolytic factors include plasmin, tissue plasminogen activator, urokinase, streptokinase, plasminogen activator inhibitor-1 inhibitor, and plasminogen activator inhibitor-2 inhibitor. Other examples of anticoagulation factors or fibrinolytics may be used.

Example methods for facilitating draining of fluid from a body cavity and for draining fluid from a body cavity are also provided. Such methods could, for example, be carried out by fluid-management systems 2100, and/or 2500 as described with reference to FIGS. 21A-36 and/or utilizing fluid-management systems 2100 or 2500.

FIG. 37 shows a flowchart of an example method 3700 of fluid management. It should be understood that for this and other processes and methods disclosed herein, flowcharts show functionality and operation of one possible implementation of present embodiments. Alternative implementations are included within the scope of the example embodiments of the present disclosure in which functions may be executed out of order from that shown or discussed, including substantially concurrent or in reverse order, depending on the functionality involved, as would be understood by those reasonably skilled in the art.

At block 3702, method 3700 involves providing a fluid-management system for selectively draining fluid from a body cavity. The fluid-management system comprises a valve assembly and a tube for carrying fluid from a body cavity of a person to the valve assembly, wherein the valve assembly is positioned external to the person's body and comprises (i) an inlet, (ii) an outlet, (iii) a pumping chamber between the inlet and outlet and configured to be compressed and decompressed to pump fluid, (iv) a first one-way valve positioned on a first side of the pumping chamber, (v) a second one-way valve positioned on a second side of the pumping chamber, and (vi) an adjustable inlet lock configured to selectively prevent fluid movement through the inlet, and wherein the tube is configured to extend from the inlet of the valve assembly to the person's body cavity. In some examples, the fluid-management system further includes an adjustable outlet lock configured to selectively prevent fluid movement through the outlet, wherein the adjustable outlet lock is positioned downstream of the second one-way valve.

At block 3704, method 3700 involves implanting a portion of the fluid-management system into the person's body, such that a proximal end of the tube is in fluid communication with the cavity and the valve assembly is positioned external to the person's body. At block 3706, after the fluid-management system is implanted into the person's body, the person may selectively drain fluid from the body cavity using the fluid-management system, as described above.

FIG. 38 shows a flowchart of an example method 3800 of draining fluid from a body cavity of a person to a reservoir external to the person's body. In particular, method 3800 is a method of operation of a fluid-management system comprising a valve assembly and a tube for carrying fluid from a body cavity of a person to the valve assembly, wherein the valve assembly is positioned external to the person's body and comprises (i) an inlet, (ii) an outlet, (iii) a pumping chamber between the inlet and outlet and configured to be compressed and decompressed to pump fluid, (iv) a first one-way valve positioned on a first side of the pumping chamber, (v) a second one-way valve positioned on a second side of the pumping chamber, and (vi) an adjustable inlet lock configured to selectively prevent fluid movement through the inlet, and wherein the tube is configured to extend from the inlet of the valve assembly to the person's body cavity. In some examples, the fluid-management system further includes an adjustable outlet lock configured to selectively prevent fluid movement through the outlet, wherein the adjustable outlet lock is positioned downstream of the second one-way valve.

At block 3802, method 3800 involves while the adjustable inlet lock is in a locked position, the adjustable inlet lock preventing fluid movement through the inlet and the outlet. At block 3804, method 3800 involves while the adjustable inlet lock is in an unlocked position, each of the one-way valves opening and closing based on compression and decompression of the pumping chamber, so as to provide a pumping action to move fluid from the body cavity through the tube, into the inlet, and out of the outlet to an exterior reservoir.

FIG. 39 shows a flowchart of an example method 3900 of draining fluid from a body cavity of a person to a reservoir external to the person's body. In particular, method 3900 is a method of operation of a fluid-management system comprising a valve assembly and a tube for carrying fluid from a body cavity of a person to the valve assembly, wherein the valve assembly is positioned external to the person's body and comprises (i) an inlet, (ii) an outlet, (iii) a pumping chamber between the inlet and outlet and configured to be compressed and decompressed to pump fluid, (iv) a first one-way valve positioned on a first side of the pumping chamber, (v) a second one-way valve positioned on a second side of the pumping chamber, and (vi) an adjustable inlet lock configured to selectively prevent fluid movement through the inlet, and wherein the tube is configured to extend from the inlet of the valve assembly to the person's body cavity. In some examples, the fluid-management system further includes an adjustable outlet lock configured to selectively prevent fluid movement through the outlet, wherein the adjustable outlet lock is positioned downstream of the second one-way valve.

At block 3902, method 3900 involves, while the adjustable inlet lock is in a locked position, an external portion of the fluid-management system attaching to a body of the person. The external portion of the fluid-management system may attach to a body of the person in various ways, such as the various ways discussed above with reference to FIGS. 13-15B. In an example, the fluid-management system attaches to a chest wall of the person. At block 3904, method 3900 involves, while the adjustable inlet lock is in an unlocked position, the pumping chamber compressing and decompressing, so as to provide a pumping action to prime the fluid-management system and get fluid moving through the fluid-management system. Further, at block 3906, method 3900 involves, while the adjustable inlet lock is in the unlocked position, after the fluid-management system is primed, the fluid-management system siphoning fluid from the body cavity through the fluid-management system. The fluid may be drained to a reservoir external to the person's body.

In an example, the fluid-management system siphons fluid from the body cavity through the fluid-management system after the fluid-management system is primed and while the pump chamber is positioned below a level of fluid in the body cavity. For instance, in an example, pump chambers 2110, 2510 are shown positioned below a level of fluid in the body cavity in FIGS. 21D and 25D, respectively. In some examples, the tube may be longer and pump chambers 2110, 2510 may be positioned further below the level of fluid in the body cavity than shown in in FIGS. 21D and 25D. In other examples, pump chambers 2110, 2510 may be positioned above the level of fluid in the body cavity.

In some examples, the position at which the pump chamber is placed relative to the level of fluid in the body to facilitate siphoning may vary depending on the body cavity being drained. For example, the position at which the pump chamber is placed relative to the level of fluid in the body to facilitate siphoning may be different for a first body cavity (e.g., a pleural cavity) than for a second body cavity (e.g., a cystic lesion in the abdomen). In this regard, for the pleural space, the chest wall tends to recoil outward and the lung tends to recoil inward. When the pleural fluid drains and the pleural space starts to become empty of fluid, this tends to create a negative pressure.

In some patients with significant pleural scarring, lung recoil can be exaggerated and lung recoil (and hence negative pressure) can be even worse. In such a case, the pump chamber outlet may need to be below the level of the fluid by at least the amount of vacuum as measured in cm H₂O (making the assumption that pleural fluid density is equal to or substantially equal to water density). On the other hand, for the abdomen, the pressures tend to be positive, so the pump chamber outlet may not need to get below the level of fluid to facilitate siphoning.

Thus, in some examples, the tip may be positioned at any level where the hydrostatic pressure column above the pump chamber outlet is sufficient to overcome any potential negative pressure (vacuum) in the body cavity. Therefore, in some examples, method 3900 involves the fluid-management system siphoning fluid from the body cavity through the fluid-management system after the fluid-management system is primed and while at least a portion of the pump chamber (e.g., the tip or distal end of the pump chamber) is positioned at a level where the hydrostatic pressure column above the pump chamber outlet is sufficient to overcome any potential negative pressure (vacuum) in the body cavity.

Example embodiments of the disclosed innovations have been described above. Those skilled in the art will understand, however, that changes and modifications may be made to the embodiments described without departing from the true scope and spirit of the present invention, which will be defined by the claims. Further, to the extent that examples described herein involve operations performed or initiated by actors, such as "persons" or other entities, this is for purposes of example and explanation only. The claims should not be construed as requiring action by such actors unless explicitly recited in the claim language.

The invention claimed is:

1. A valve assembly comprising:
an inlet;
an outlet;
a plurality of one-way valves positioned between the inlet and outlet; and
an adjustable outlet lock positioned downstream of the plurality of one-way valves and configured to selectively prevent fluid movement through the outlet, wherein the valve assembly is configured to (i) be positioned external to a body of a person and (ii) attach to a tube for carrying fluid from a body cavity of the person to the valve assembly.

2. The valve assembly of claim 1, wherein the inlet is configured to attach to the tube, and wherein the tube is configured to extend from the inlet to the person's body cavity.

3. The valve assembly of claim 1, wherein the valve assembly comprises a pumping chamber that houses the plurality of one-way valves, wherein the plurality of one-way valves comprise a first one-way valve positioned on a first side of the pumping chamber and a second one-way valve positioned on a second side of the pumping chamber, and wherein the pumping chamber is configured to be compressed and decompressed to pump fluid.

4. The valve assembly of claim 3, wherein each one-way valve of the plurality of one-way valves is configured to open and close based on compression and decompression of the pumping chamber.

5. The valve assembly of claim 4, wherein each one-way valve of the plurality of one-way valves is further configured to open and close based on fluctuations in pressure between the person's body cavity and the one-way valve that occur based on respiratory action of a breathing cycle of the person.

6. The valve assembly of claim 5, wherein each one-way valve of the plurality of one-way valves is configured to (i) open due to positive pressure between the person's body cavity and the one-way valve during an expiration phase of the breathing cycle and (ii) close due to negative pressure between the person's body cavity and the one-way valve during an inspiration phase of the breathing cycle.

7. The valve assembly of claim 1, wherein the adjustable outlet lock of the valve assembly is non-removably attached to the valve assembly.

8. The valve assembly of claim 1, wherein the adjustable outlet lock is positioned at the outlet.

9. The valve assembly of claim 1, wherein each one-way valve of the plurality of one-way valves is configured to open with a cracking pressure of less than about 25 cmH₂O.

10. The valve assembly of claim 9, wherein the cracking pressure is less than about 5 cmH₂O.

11. The valve assembly of claim 1, wherein each one-way valve of the plurality of one-way valves is configured to prevent retrograde flow.

12. The valve assembly of claim 11, wherein each one-way valve of the plurality of one-way valves is configured to reseal with a differential back pressure of less than about 15 cmH₂O.

13. The valve assembly of claim 12, wherein the differential back pressure is less than about 2 cmH₂O.

14. The valve assembly of claim 1, wherein each one-way valve of the plurality of one-way valves comprises a plurality of lips defining a slit that is movable from a closed position to an open position, and wherein the lips are configured to have a surface area of interaction of less than 6 millimeters² when the slit is in the closed position.

15. The valve assembly of claim 1, wherein the adjustable outlet lock is located at the outlet, and wherein the adjustable outlet lock is configured to move between a locked position in which the adjustable outlet lock seals the outlet and an unlocked position in which the adjustable outlet lock allows fluid movement through the outlet.

16. The valve assembly of claim 15, wherein the adjustable outlet lock comprises at least one of a cap, a pinch lever, a twist pinch, or an offset device.

17. The valve assembly of claim 1, wherein the valve assembly comprises a body that houses the plurality of one-way valves, and wherein the body is coated with at least one of anticoagulation factors or fibrinolytic factors.

18. The valve assembly of claim 1, wherein the body cavity comprises one of a pleural cavity, a peritoneal cavity, a cerebrospinal cavity, a pericardial cavity, a breast cavity, or a cavity of a cystic lesion.

19. A valve assembly comprising:
an inlet;
an outlet;
one or more one-way valves positioned between the inlet and outlet, wherein each of the one or more one-way valves is configured to allow fluid movement in one direction during a fluid draining process and prevent retrograde flow during the fluid draining process; and
an adjustable outlet lock positioned downstream of the one or more one-way valves and configured to selectively prevent fluid movement through the outlet, wherein the valve assembly is configured to (i) be positioned external to a body of a person and (ii) attach to a tube for carrying fluid from a body cavity of the person to the valve assembly.

20. The valve assembly of claim 19, wherein the valve assembly is non-removably attached to the tube for carrying fluid from the body cavity of the person to the valve assembly.

21. The valve assembly of claim 19, wherein the adjustable outlet lock of the valve assembly is non-removably attached to the valve assembly.

22. The valve assembly of claim 19, wherein the adjustable outlet lock of the valve assembly is removable.

23. The valve assembly of claim 19, wherein the inlet is configured to attach to the tube, and wherein the tube is configured to extend from the inlet to the person's body cavity.

24. A valve assembly comprising:

an inlet;

an outlet;

one or more one-way valves positioned between the inlet and outlet, wherein each of the one or more one-way valves is configured to allow fluid movement in one direction during a fluid draining process and prevent retrograde flow during the fluid draining process; and an adjustable outlet lock configured to selectively prevent fluid movement through the outlet, wherein the valve assembly is configured to be positioned external to a body of a person, wherein the valve assembly is non-removably attached to a tube for carrying fluid from a body cavity of the person to the valve assembly, and wherein the adjustable outlet lock of the valve assembly is non-removably attached to the valve assembly.

25. The valve assembly of claim 24, wherein the adjustable outlet lock is positioned downstream of the one or more one-way valves.

\* \* \* \* \*